United States Patent
Lafauci et al.

(10) Patent No.: US 11,433,032 B2
(45) Date of Patent: Sep. 6, 2022

(54) SYSTEMS AND METHODS FOR REMOVING A COVERING FROM A BODILY SURFACE

(71) Applicant: MIDAS Healthcare Solutions, Inc., Center Moriches, NY (US)

(72) Inventors: Michael A. Lafauci, Center Moriches, NY (US); Jeffrey R. Wahl, Beachwood, OH (US); Andrew M. Brown, Hackensack, NJ (US); Jonathan Pinsky, Bedford, NY (US)

(73) Assignee: MIDAS HEALTHCARE SOLUTIONS, INC., Center Moriches, NY (US)

( * ) Notice: Subject to any disclaimer, the term of this patent is extended or adjusted under 35 U.S.C. 154(b) by 0 days.

(21) Appl. No.: 17/152,040

(22) Filed: Jan. 19, 2021

(65) Prior Publication Data
US 2022/0125738 A1    Apr. 28, 2022

Related U.S. Application Data

(63) Continuation of application No. PCT/US2019/042059, filed on Jul. 16, 2019.
(Continued)

(51) Int. Cl.
*A61M 35/00* (2006.01)
*A61K 9/70* (2006.01)
*G16H 20/10* (2018.01)

(52) U.S. Cl.
CPC ............ *A61K 9/703* (2013.01); *A61M 35/00* (2013.01); *G16H 20/10* (2018.01);
(Continued)

(58) Field of Classification Search
CPC ...... A61M 37/0015; A61M 2037/0023; A61M 2037/0061; A61M 2205/50; A61M 35/00
See application file for complete search history.

(56) References Cited

U.S. PATENT DOCUMENTS 6,851,615 B2    2/2005  Jones
8,872,663 B2   10/2014  Forster
(Continued)

FOREIGN PATENT DOCUMENTS

WO    WO-2020018577 A1    1/2020

OTHER PUBLICATIONS

Koh, et al., A soft, wearable microfluidic device for the capture, storage, and colorimetric sensing of sweat. Sci Transl Med. Nov. 23, 2016; 8(366): 366ra165. doi: 10.1126/scitranslmed.aaf2593.
(Continued)

*Primary Examiner* — Deanna K Hall
(74) *Attorney, Agent, or Firm* — Wilson Sonsini Goodrich & Rosati

(57) ABSTRACT

The present disclosure provides a method of removing a cover from a bodily surface of a subject. The method may comprise applying a cover removal device to a portion of the cover that is disposed on the bodily surface of the subject, thereby generating a connection between the cover removal device and the portion of the cover. The method may comprise moving the cover removal device across the bodily surface of the subject in order to selectively remove the cover from the bodily surface and capture the cover onto the cover removal device, without the cover removal device substantially affecting or interfering with the bodily surface of the subject.

20 Claims, 26 Drawing Sheets

Related U.S. Application Data

(60) Provisional application No. 62/728,595, filed on Sep. 7, 2018, provisional application No. 62/711,872, filed on Jul. 30, 2018, provisional application No. 62/699,505, filed on Jul. 17, 2018.

(52) U.S. Cl.
CPC .............. *A61M 2205/273* (2013.01); *A61M 2205/6009* (2013.01); *A61M 2209/04* (2013.01)

(56) References Cited

U.S. PATENT DOCUMENTS

| | | | |
|---|---|---|---|
| 9,147,043 | B2 | 9/2015 | Melby et al. |
| 9,636,273 | B1 | 5/2017 | Harris |
| 10,004,887 | B2 | 6/2018 | Gross et al. |
| 10,039,911 | B2 | 8/2018 | Yamamoto et al. |
| 2006/0062734 | A1 | 3/2006 | Melker et al. |
| 2007/0260491 | A1 | 11/2007 | Palmer et al. |
| 2008/0059226 | A1 | 3/2008 | Melker et al. |
| 2009/0022767 | A1 | 1/2009 | Kauffman et al. |
| 2014/0149131 | A1 | 5/2014 | Bear et al. |
| 2014/0188272 | A1 | 7/2014 | Bear et al. |
| 2014/0297028 | A1 | 10/2014 | Bilotti |
| 2016/0283693 | A1 | 9/2016 | Levin |
| 2018/0036523 | A1 | 2/2018 | Gross et al. |

OTHER PUBLICATIONS

Lu, et al., Flexible and stretchable electronics paving the way for soft robotics. Soft Robotics vol. 1, No. 1, 2013. doi: 10.1089/soro.2013.0005.

PCT/US2019/042059 International Search Report and Written Opinion dated Oct. 25, 2019.

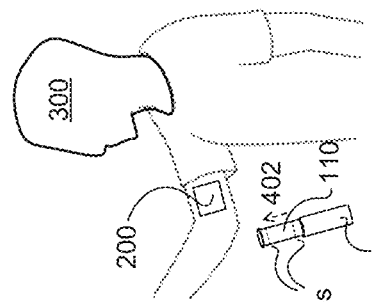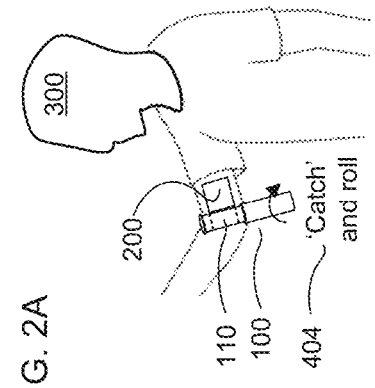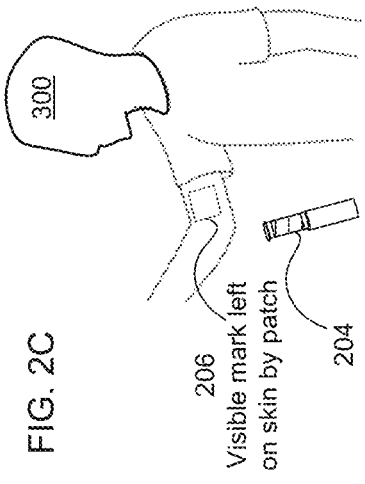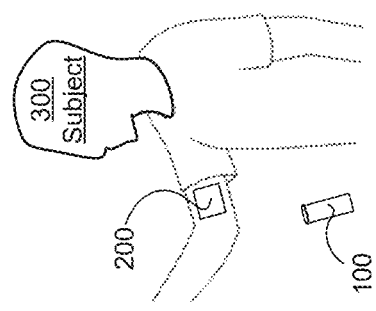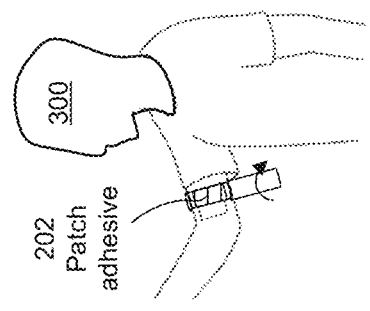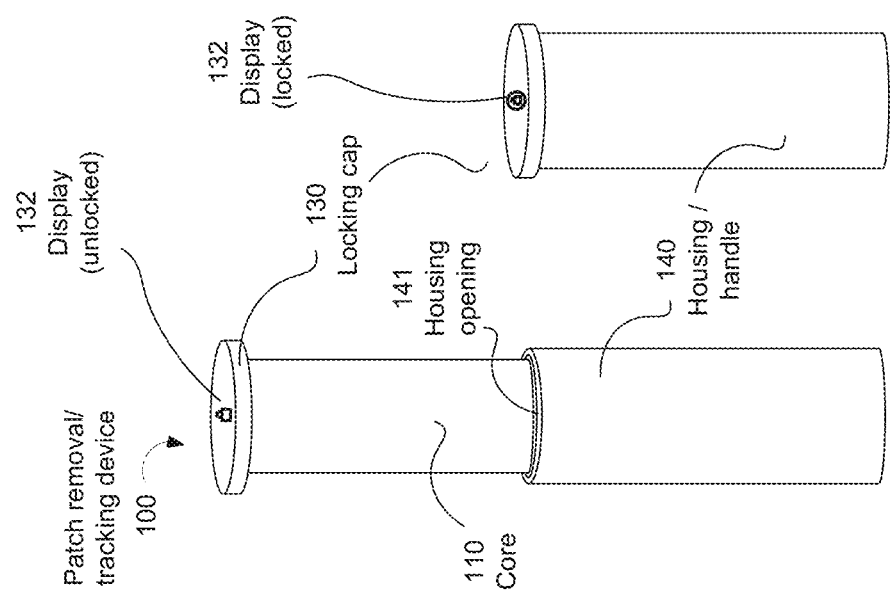

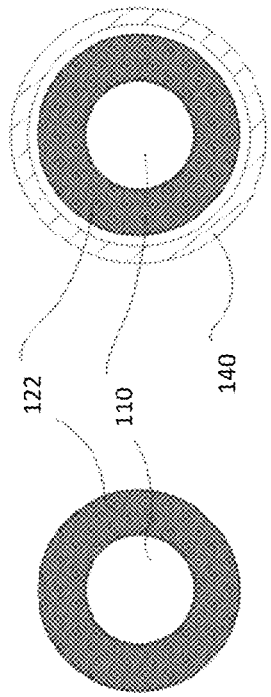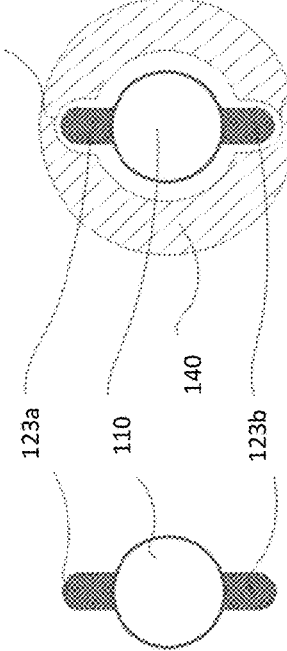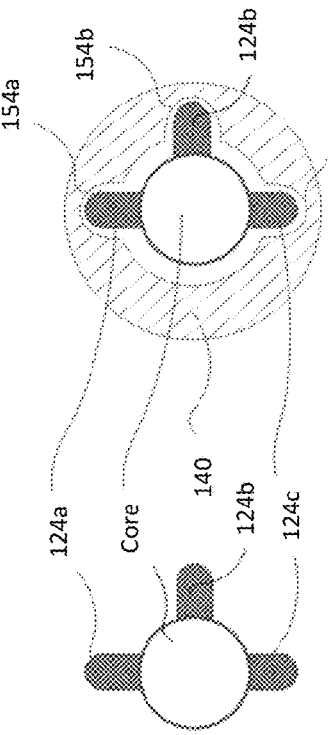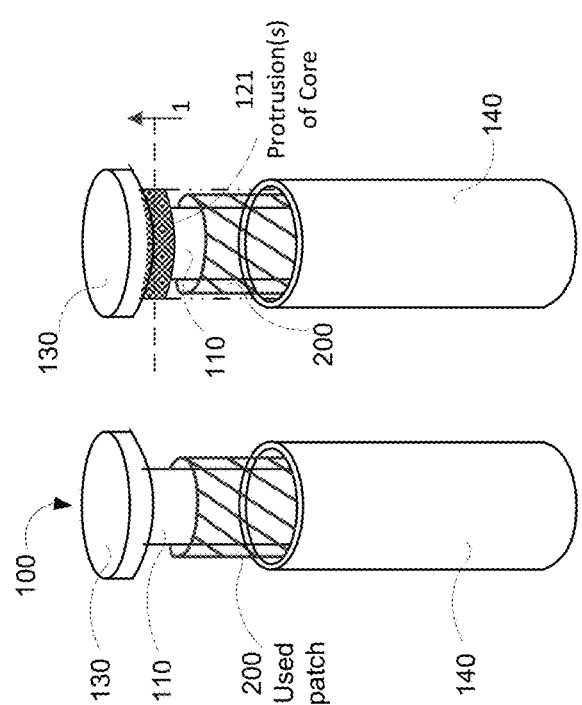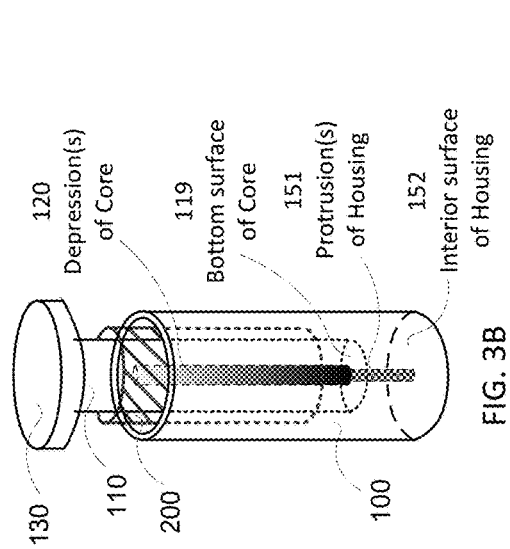

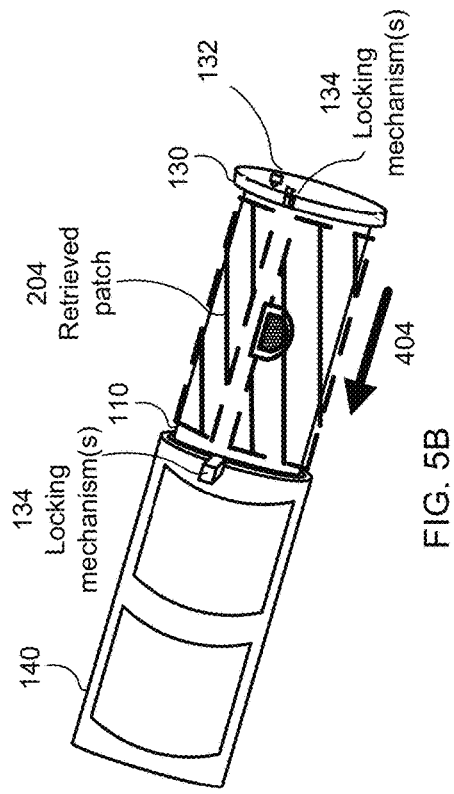
FIG. 5A
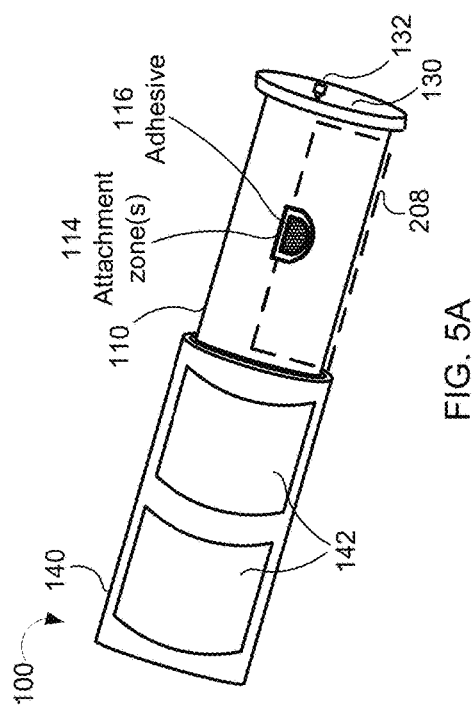
FIG. 5B
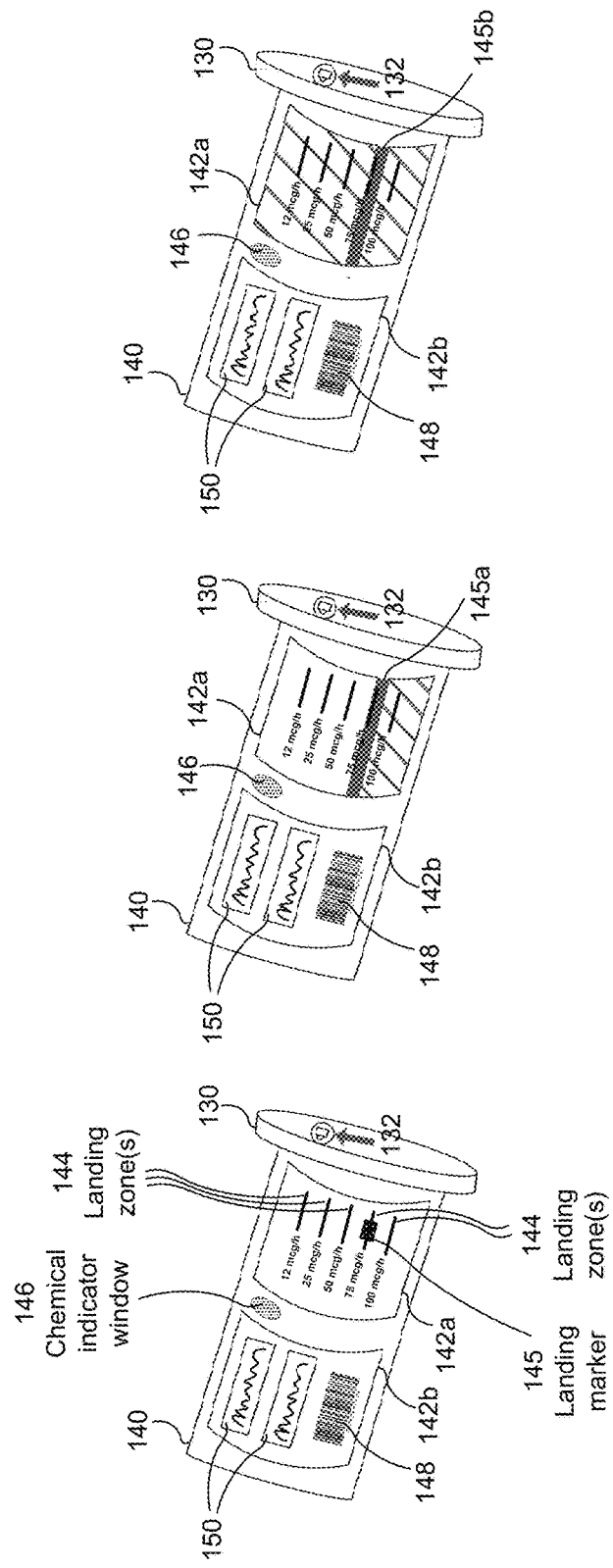
FIG. 5C
FIG. 5D
FIG. 5E

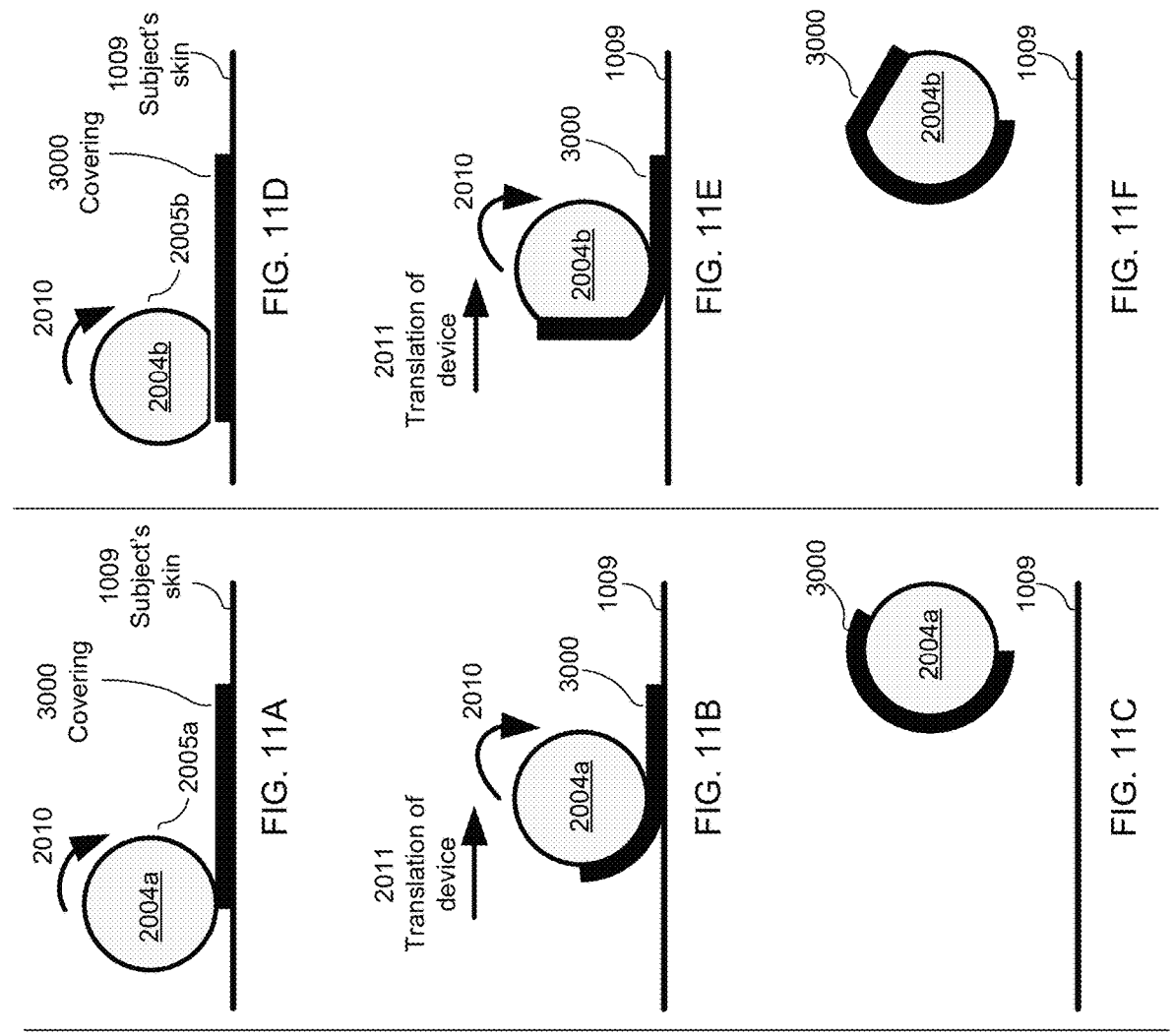
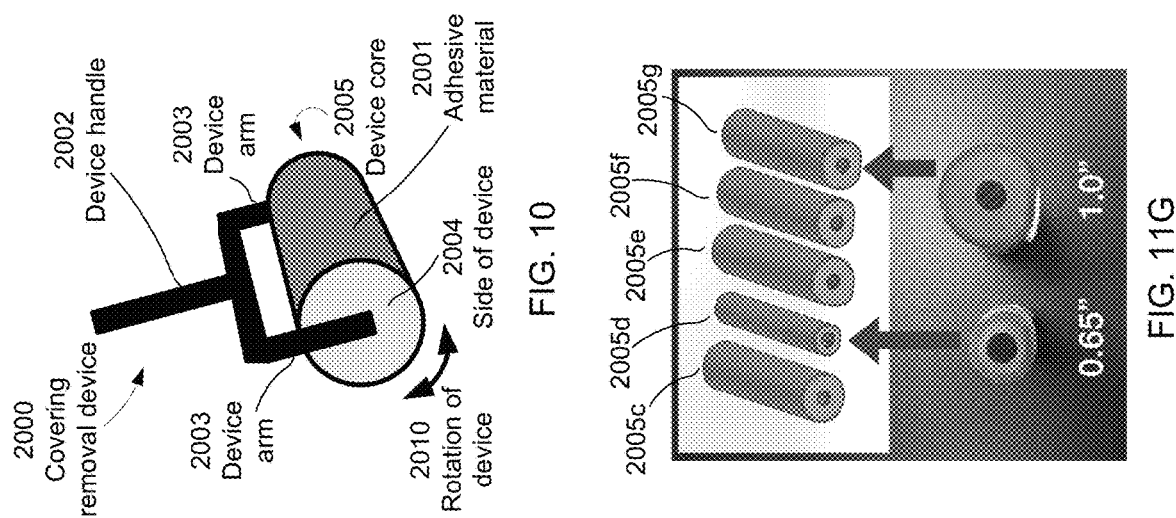

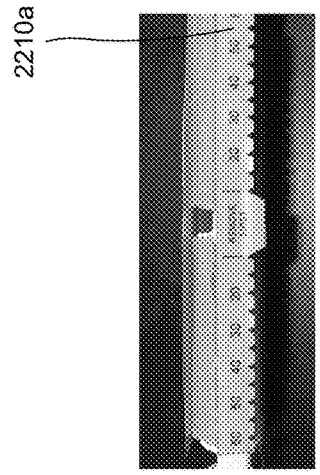
FIG. 13E
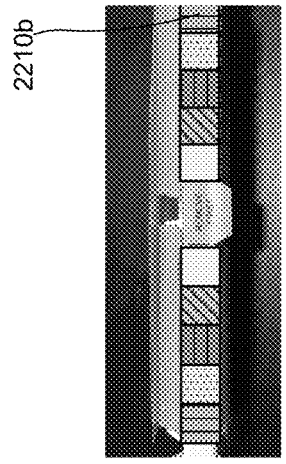
FIG. 13F
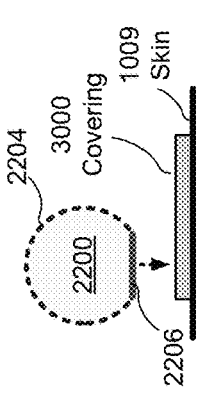
FIG. 13B
FIG. 13C
FIG. 13D
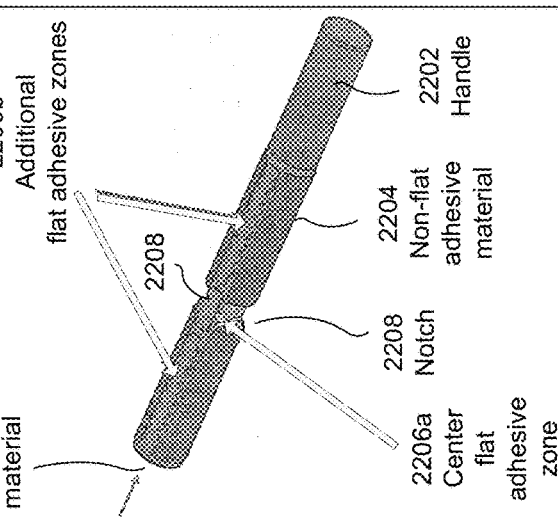
FIG. 13A

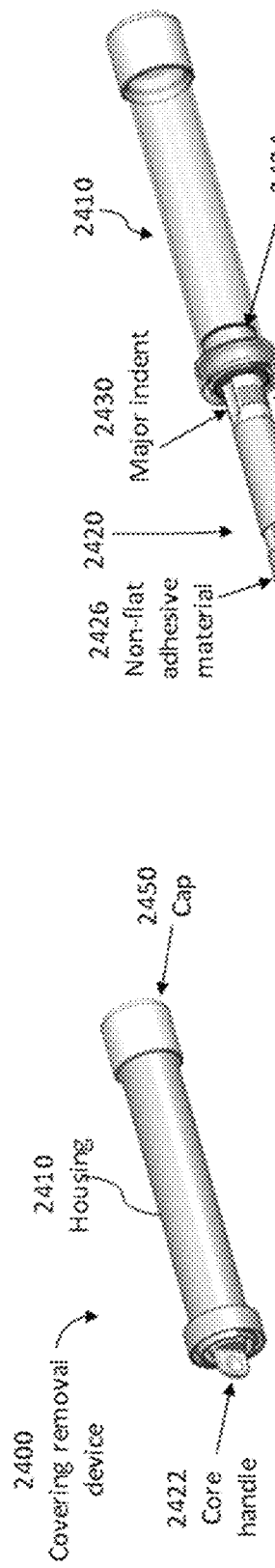
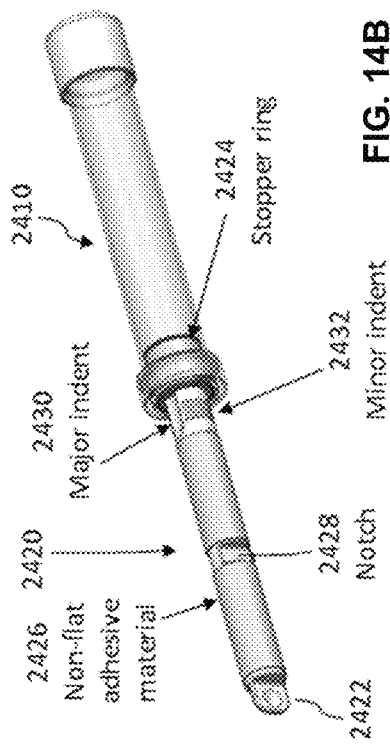
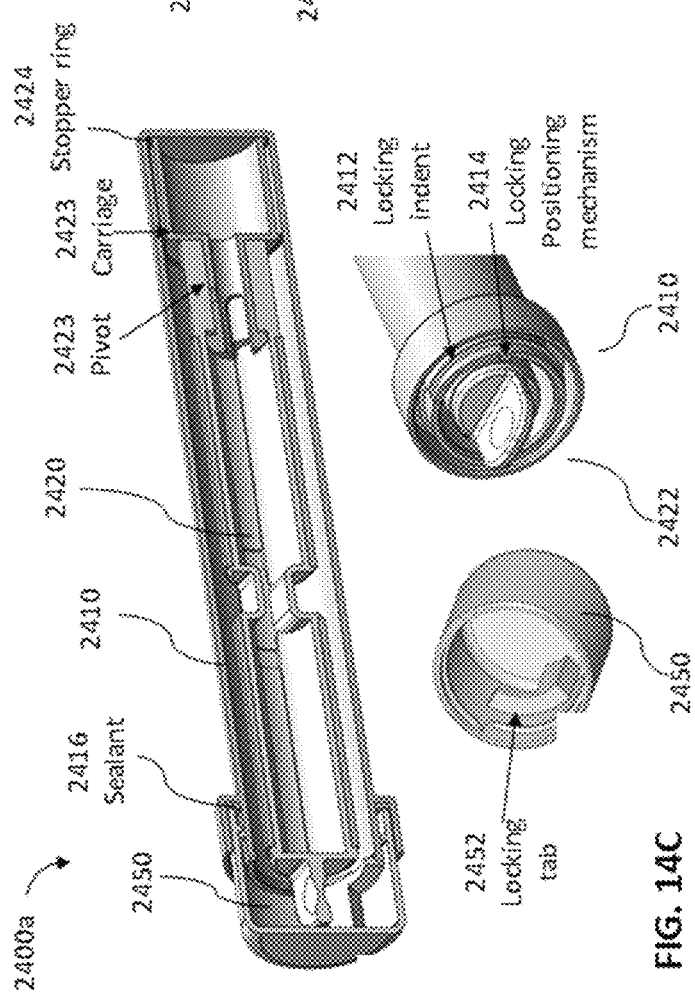
FIG. 14A
FIG. 14B
FIG. 14C
FIG. 14D

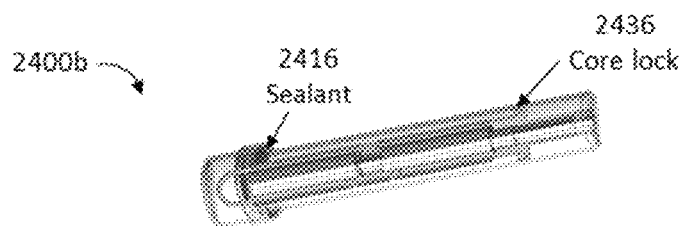
FIG. 14E
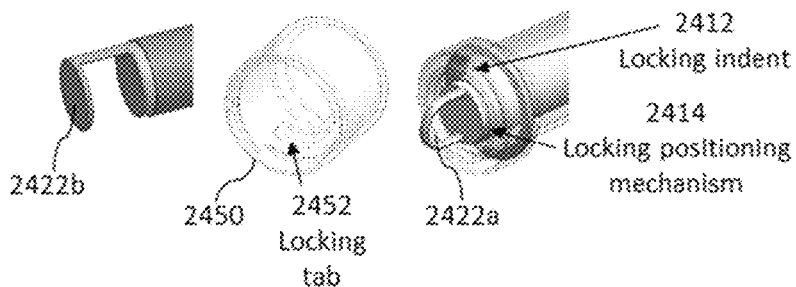
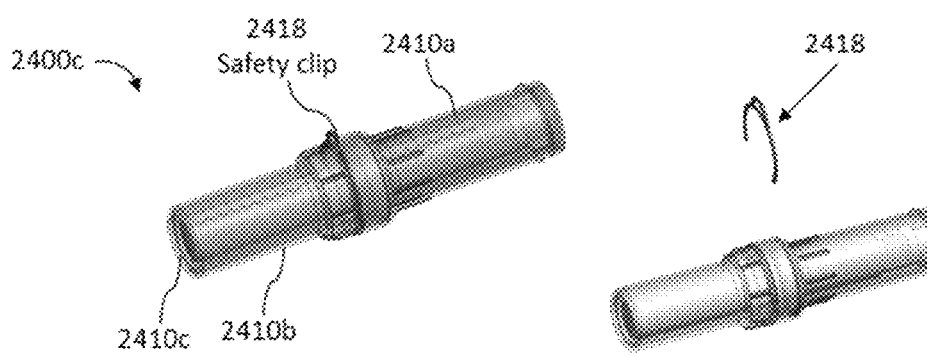
FIG. 14F
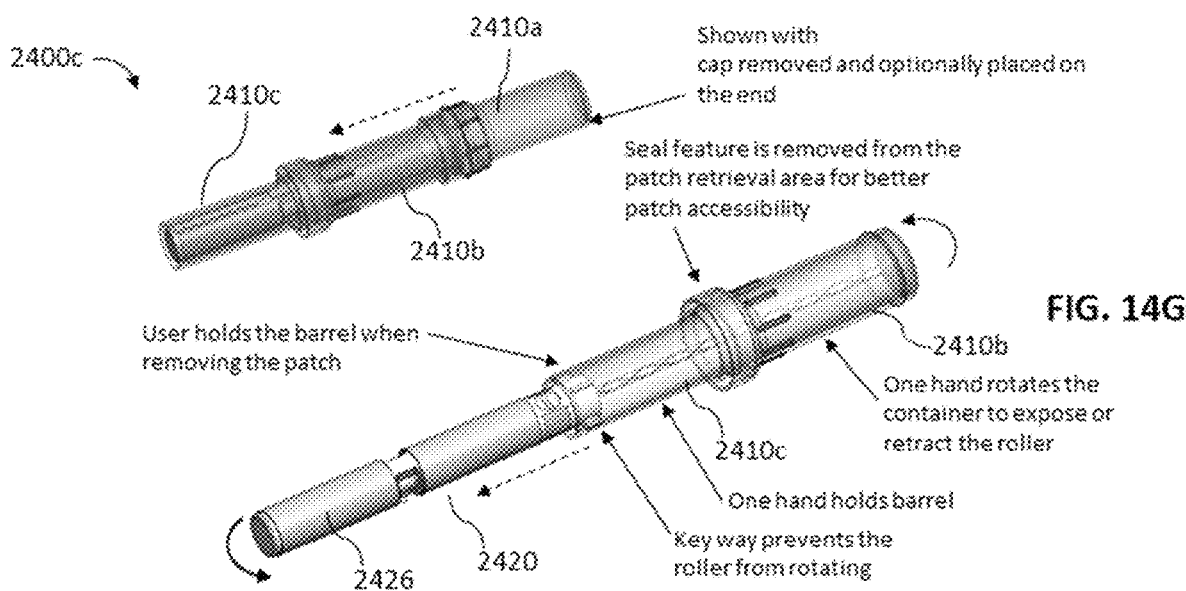
FIG. 14G

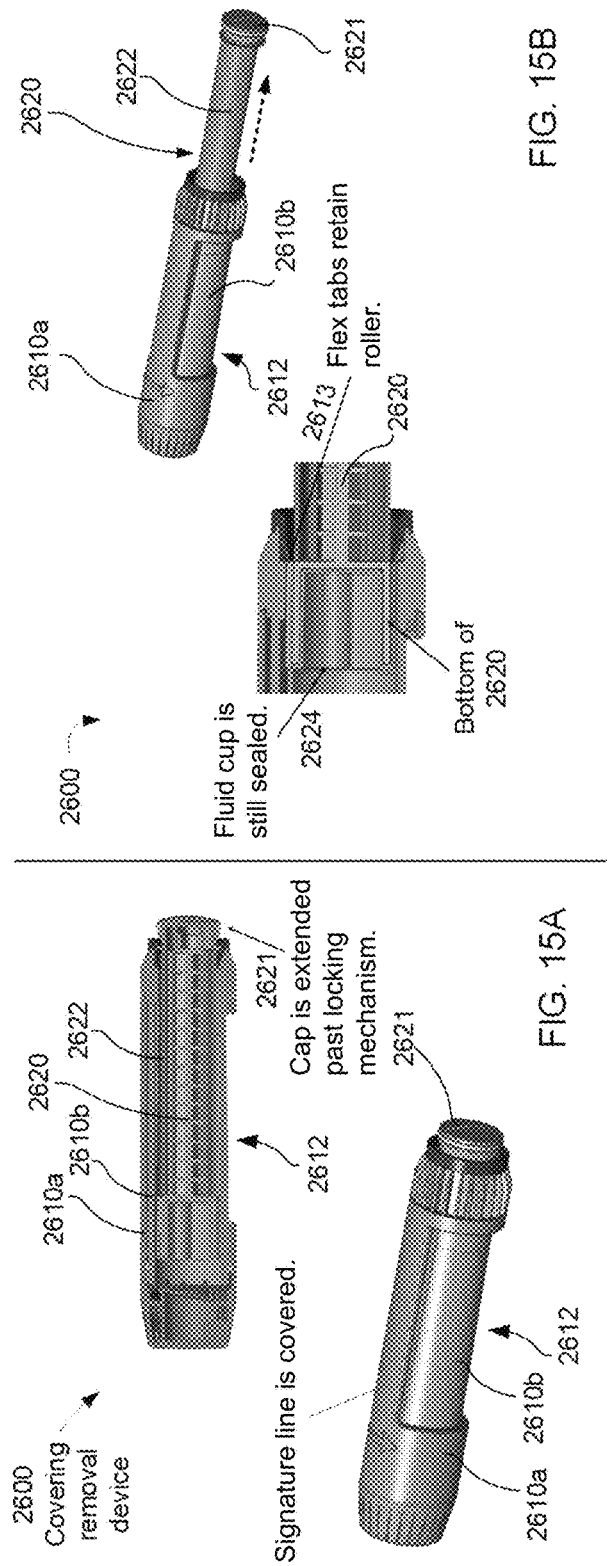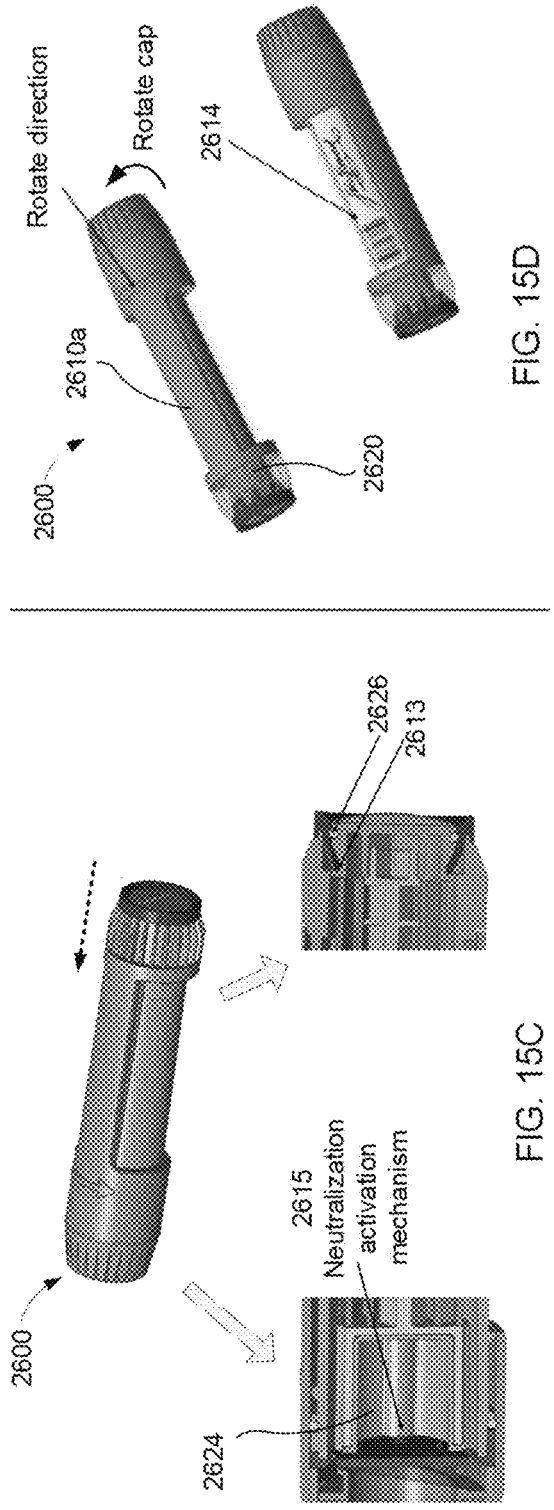
FIG. 15A
FIG. 15B
FIG. 15C
FIG. 15D

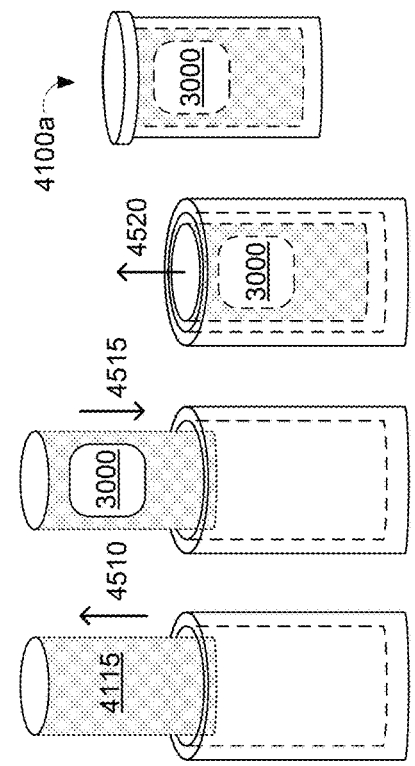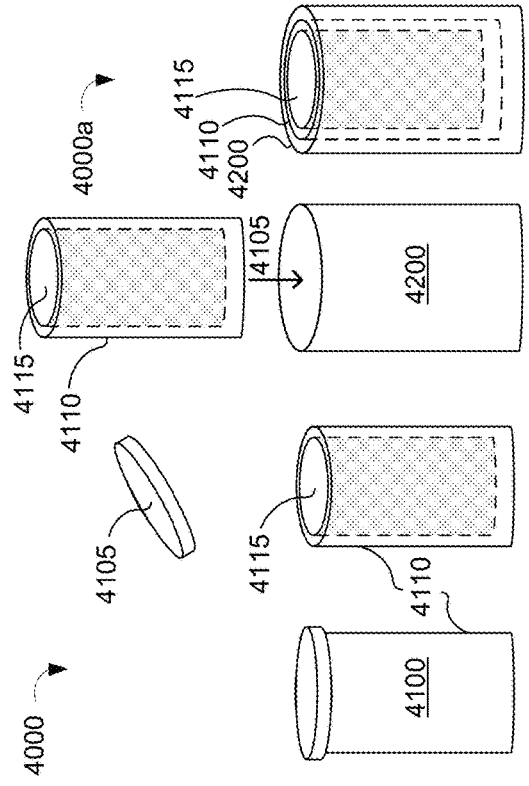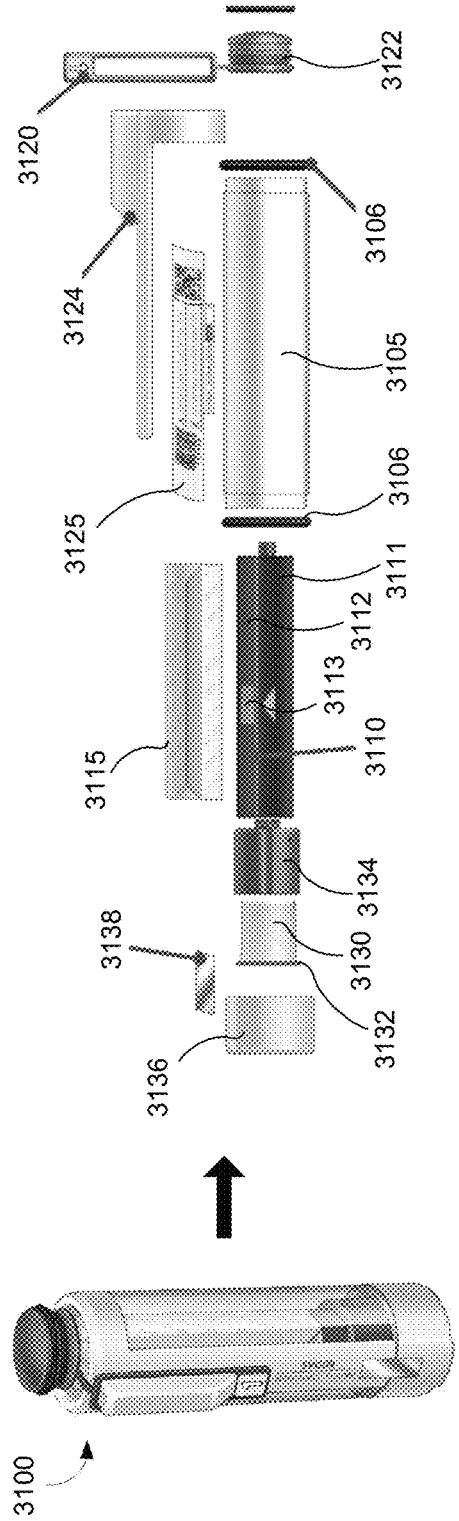

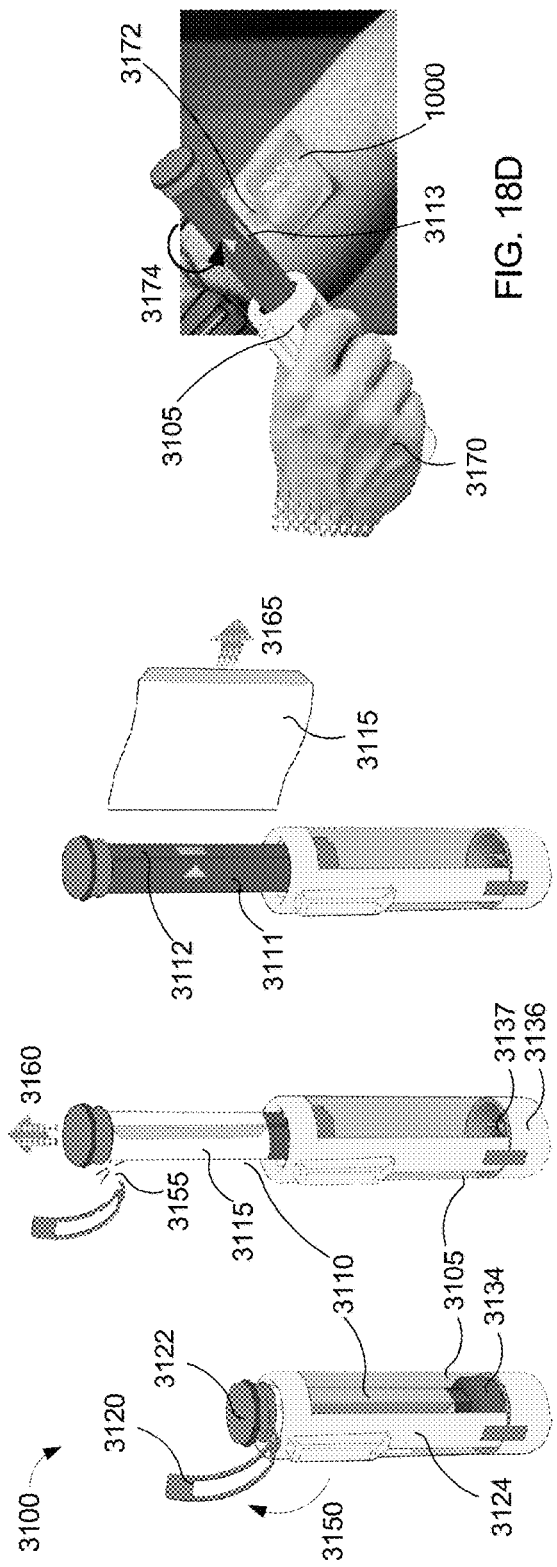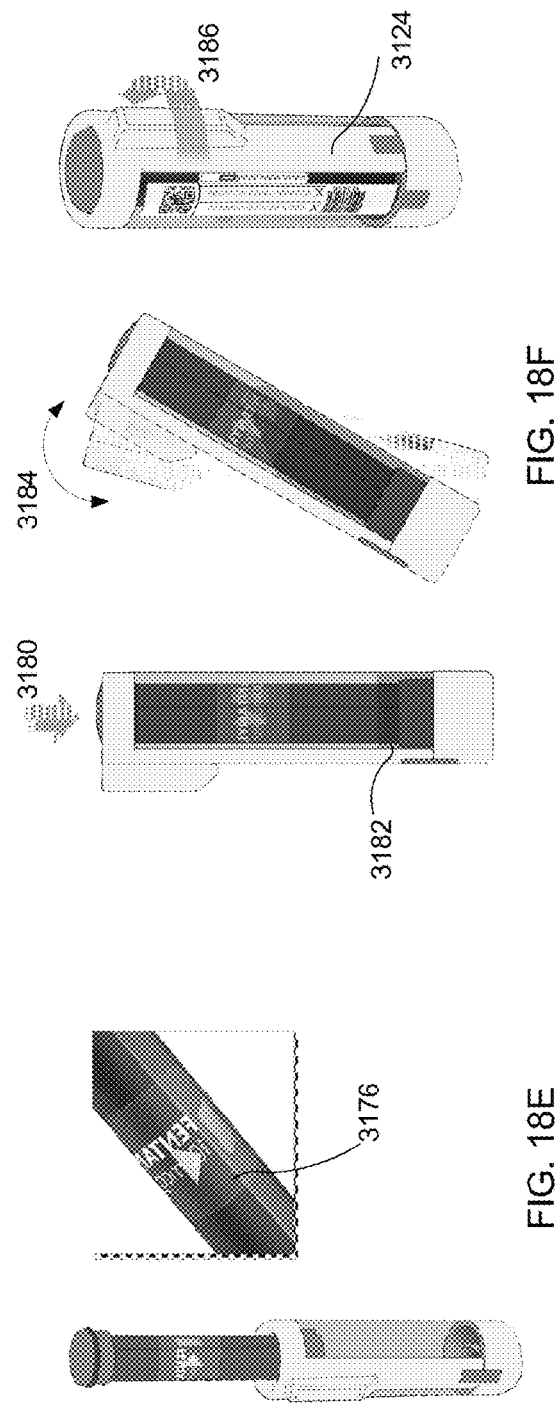

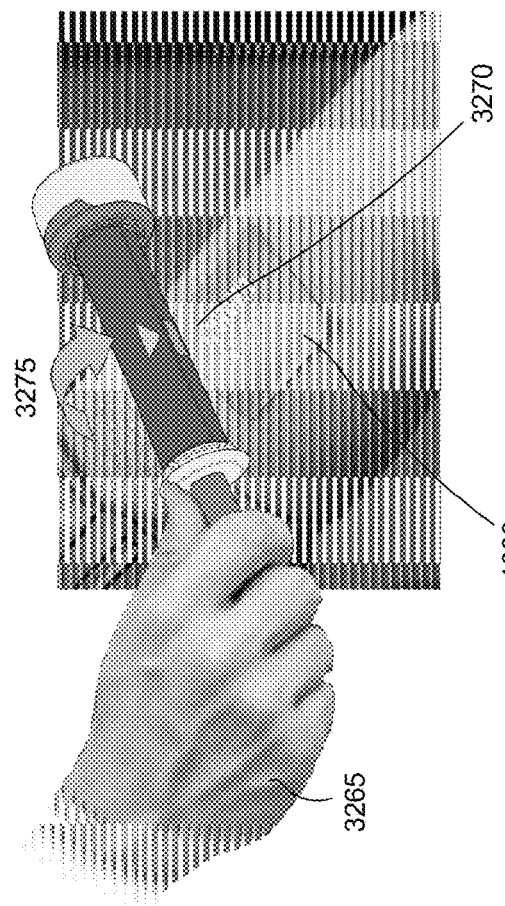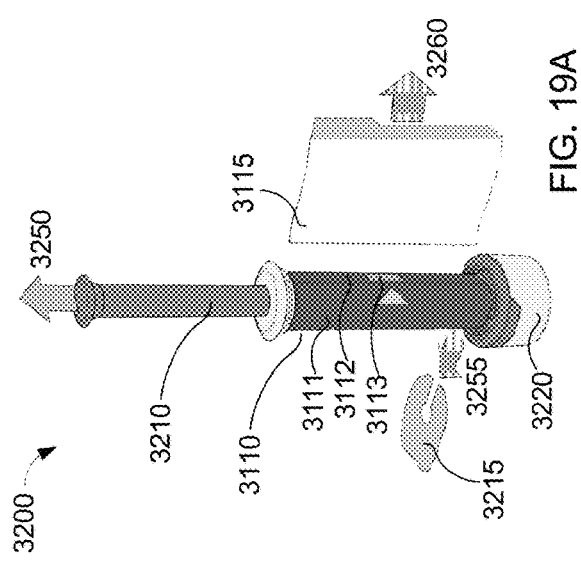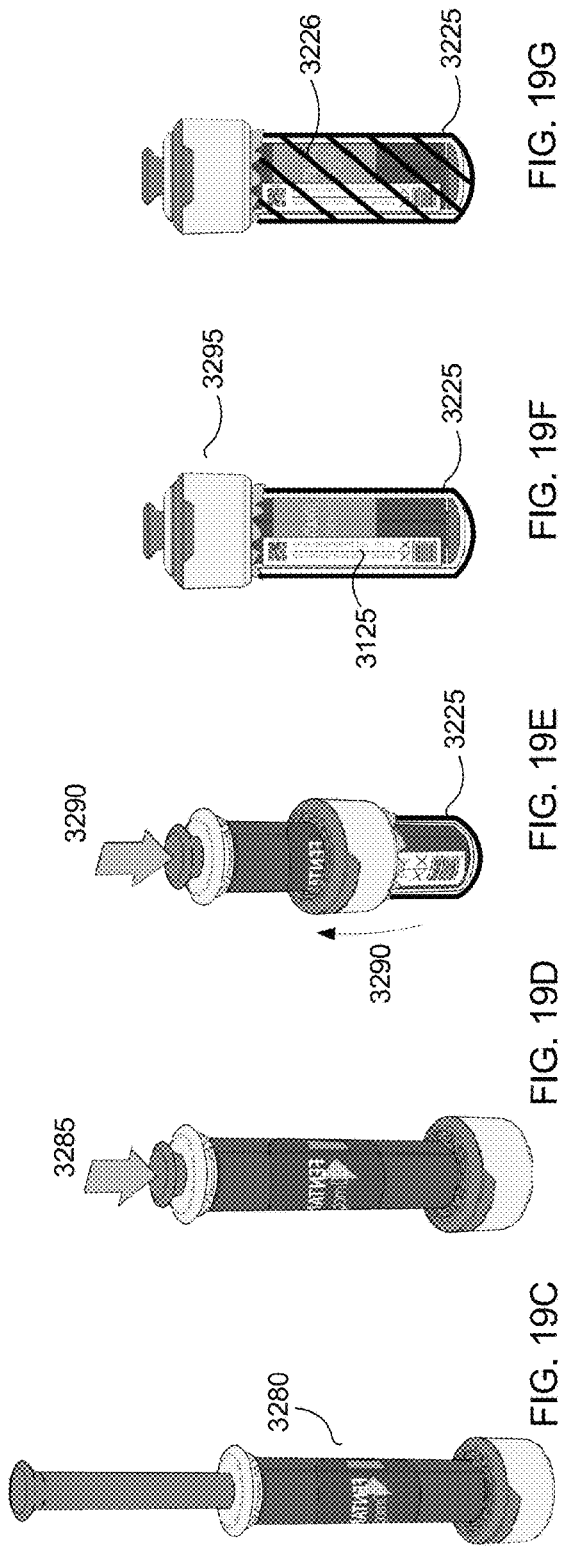

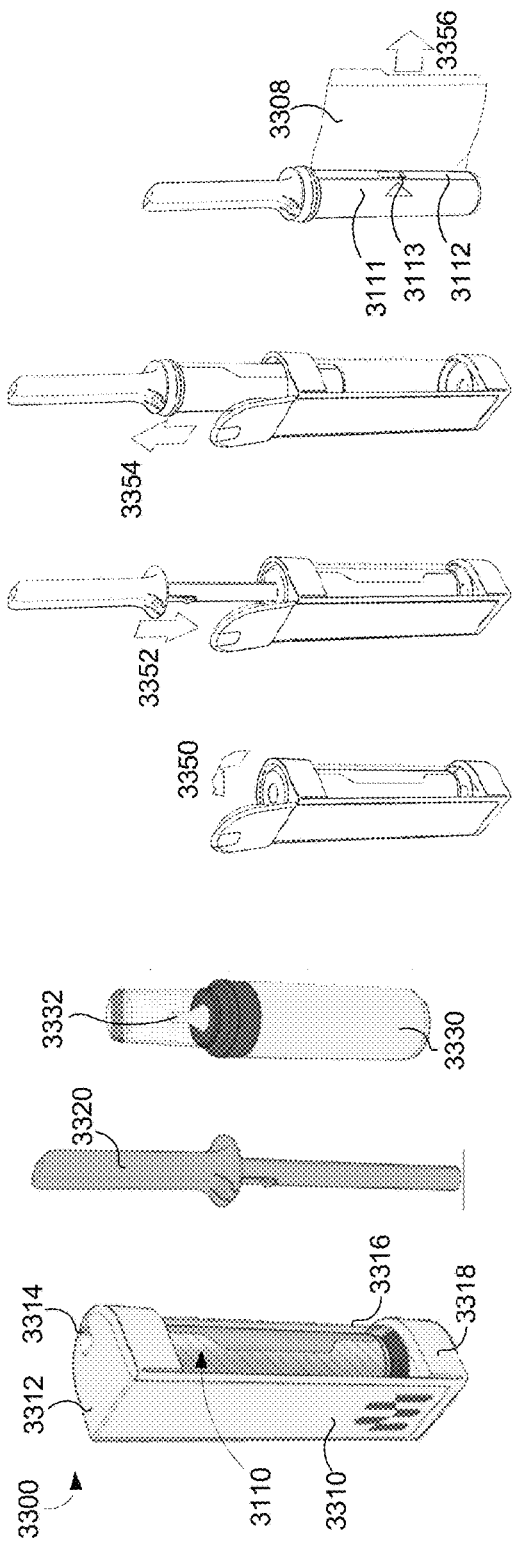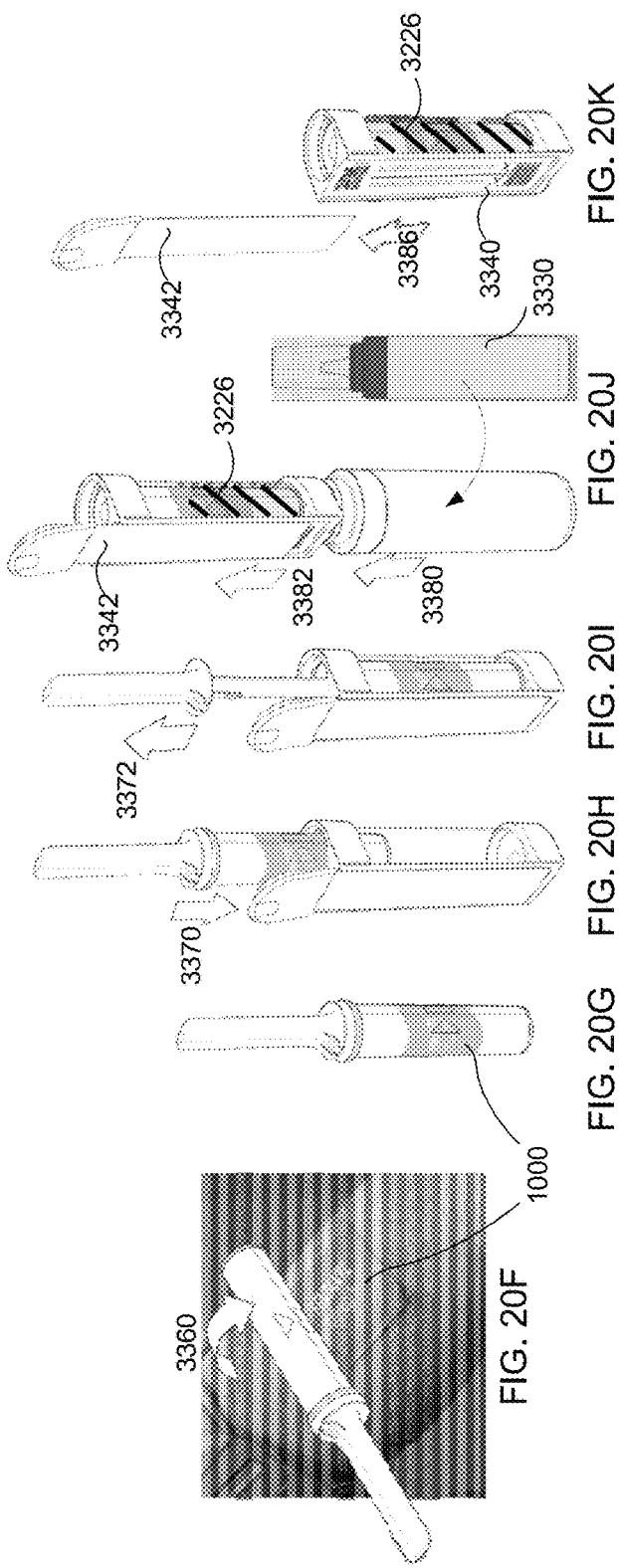

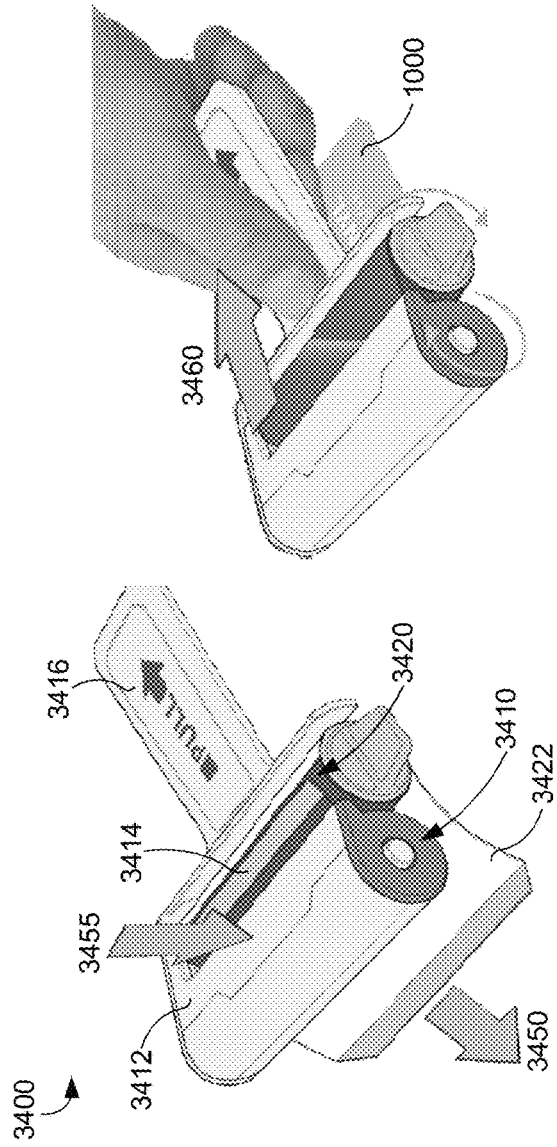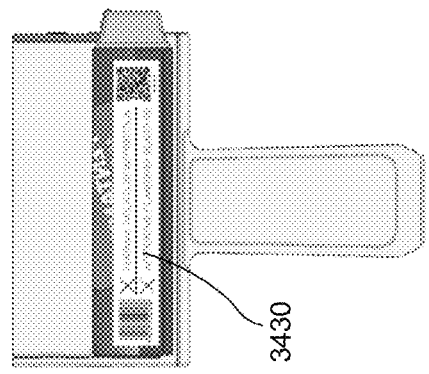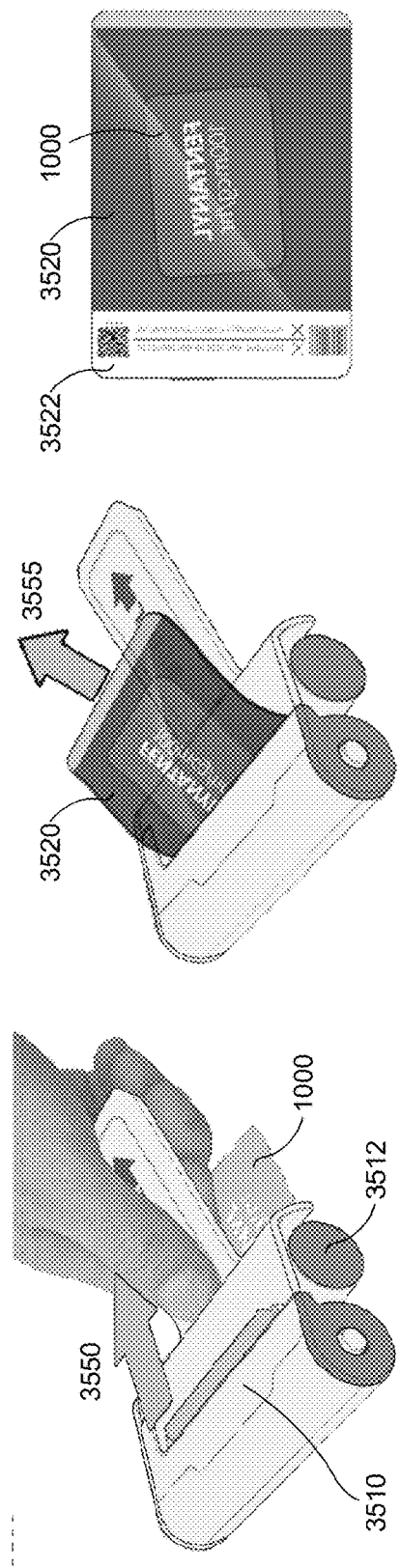

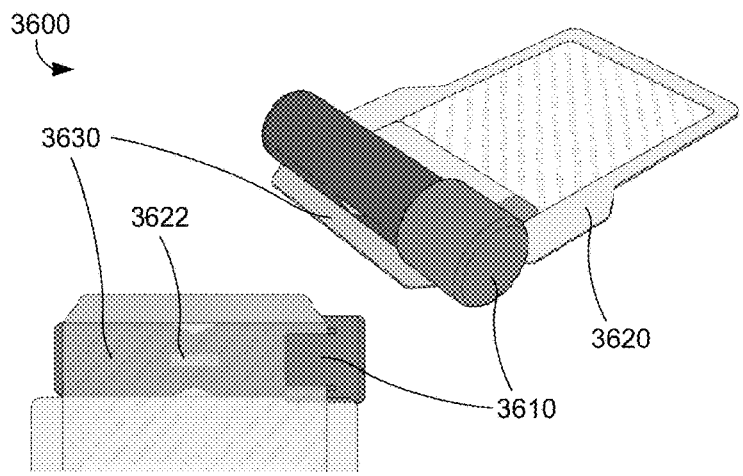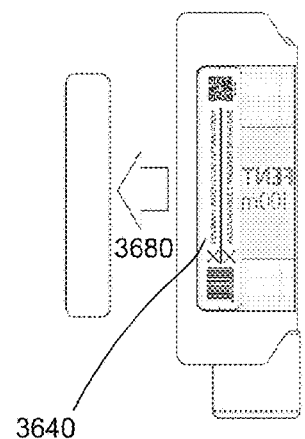
FIG. 23A  FIG. 23H
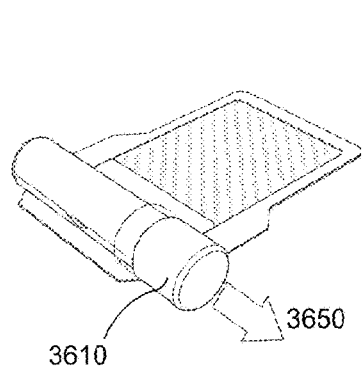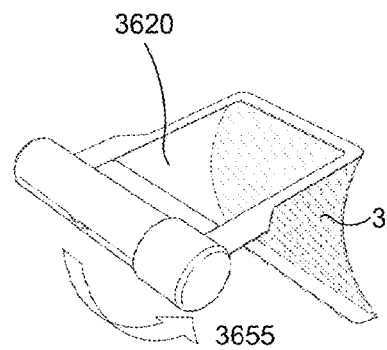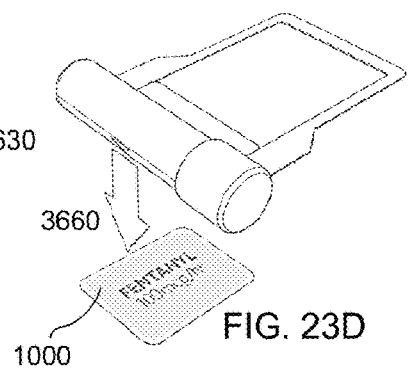
FIG. 23B  FIG. 23C  FIG. 23D
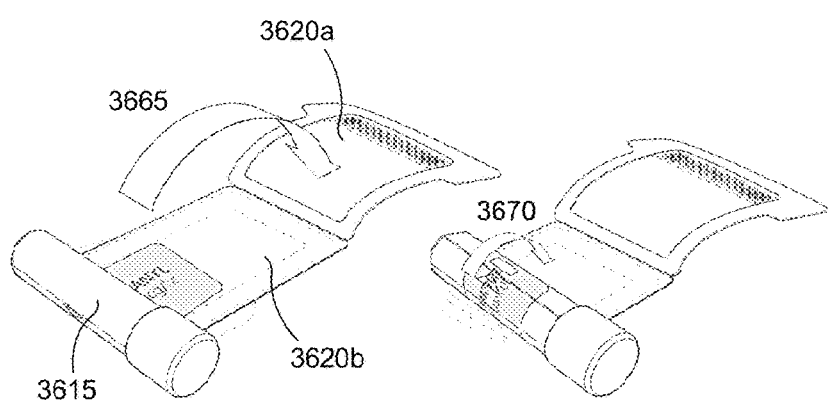
FIG. 23E  FIG. 23F  FIG. 23G

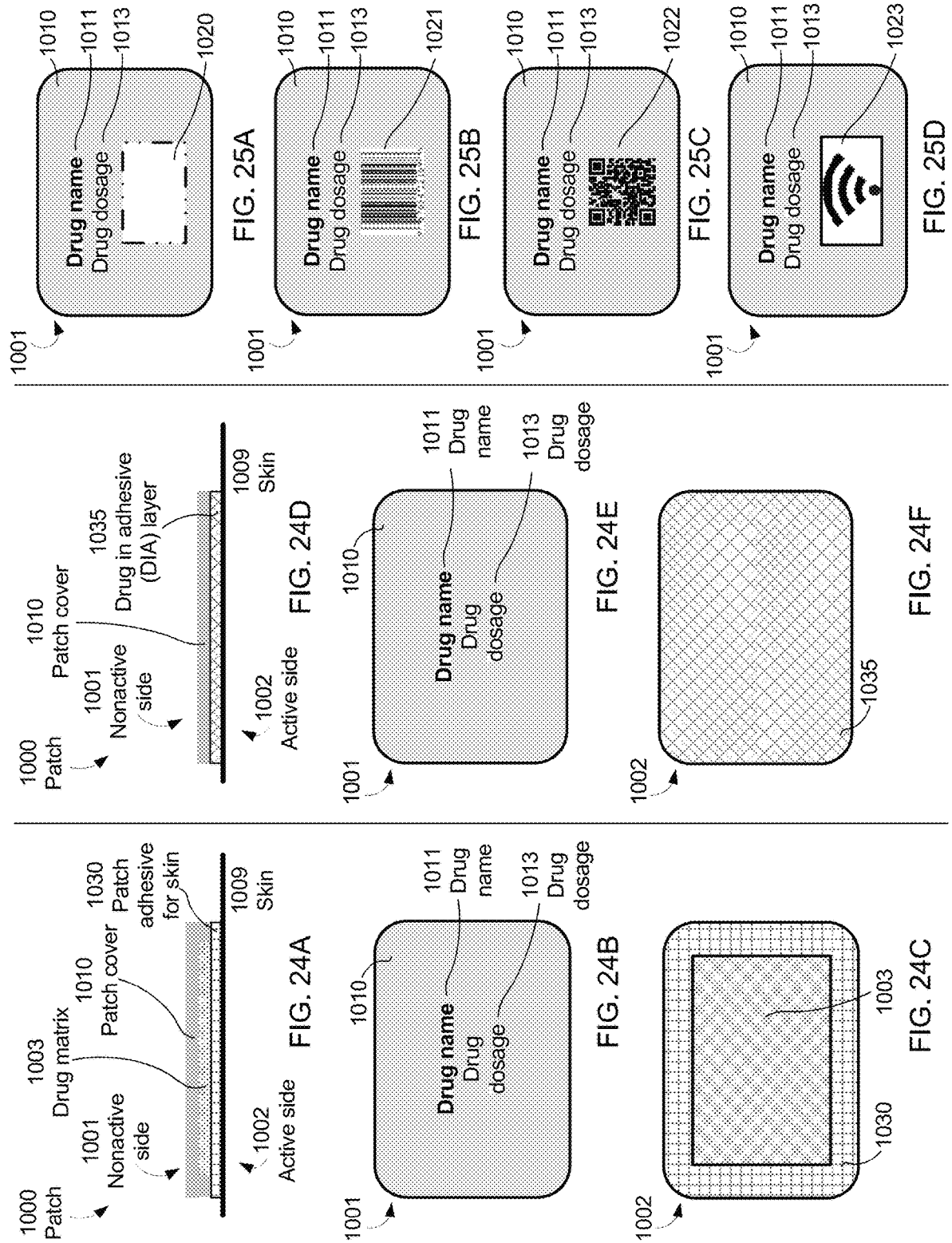

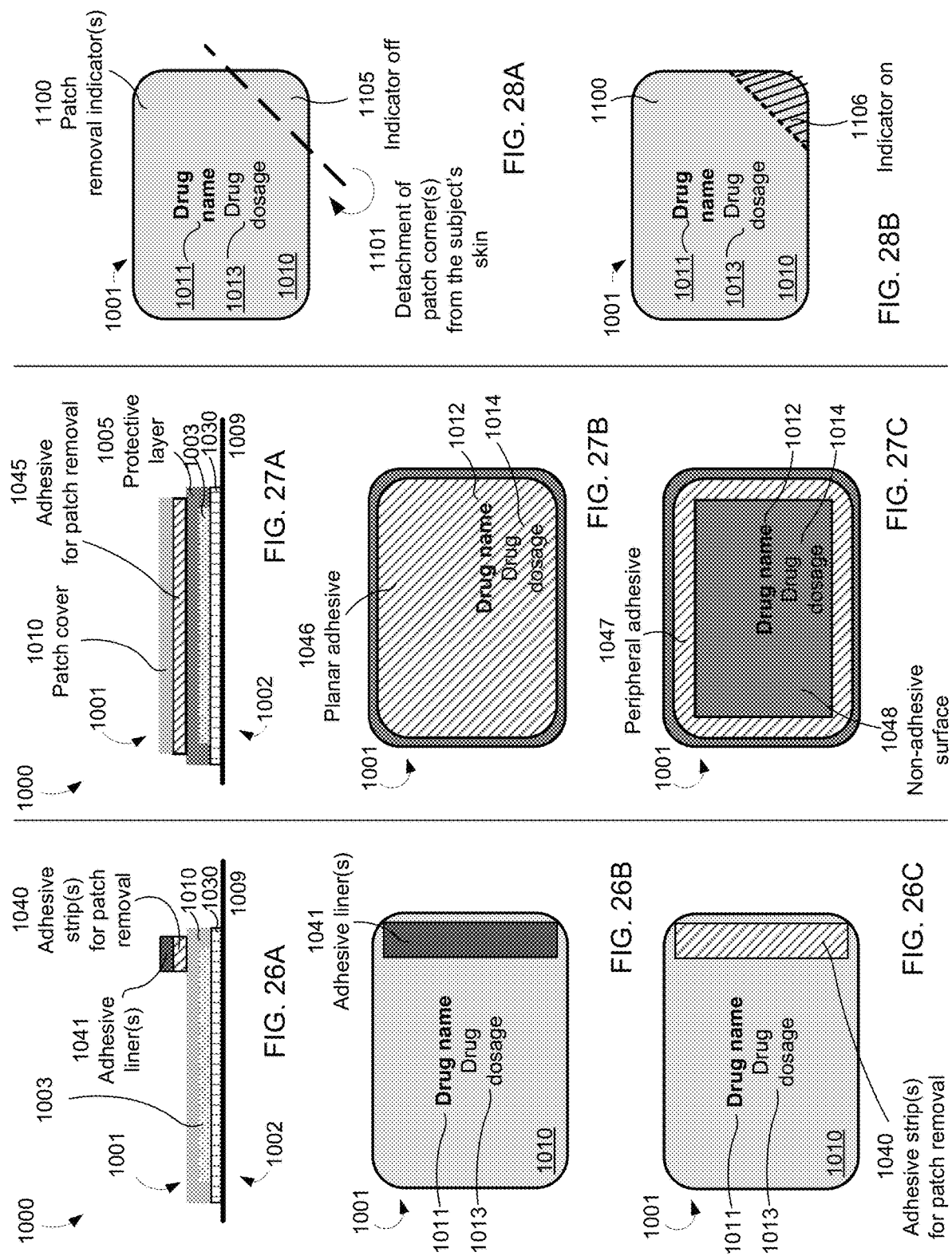

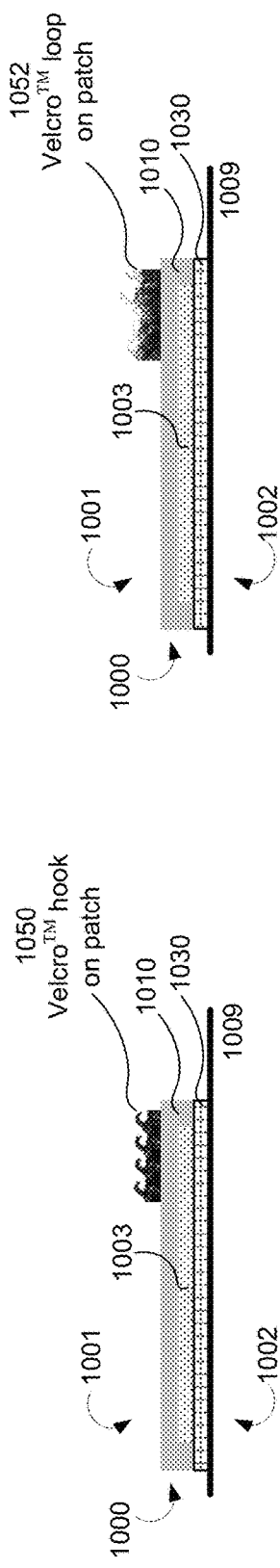
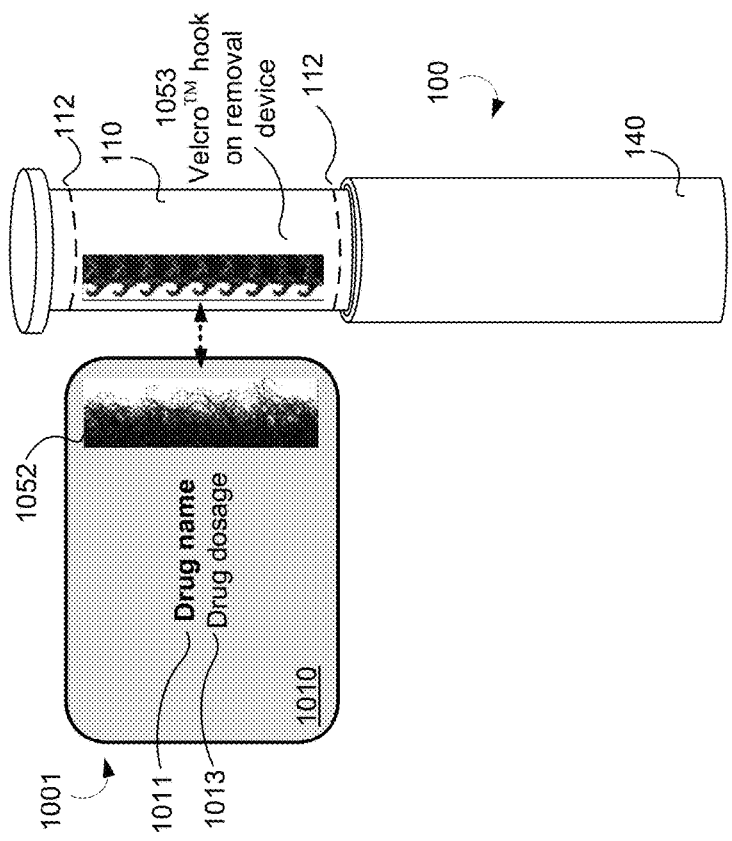
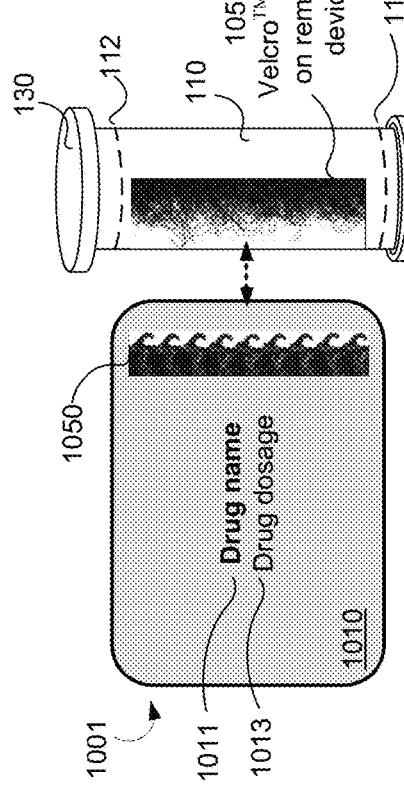
FIG. 29A
FIG. 29B
FIG. 29C
FIG. 29D

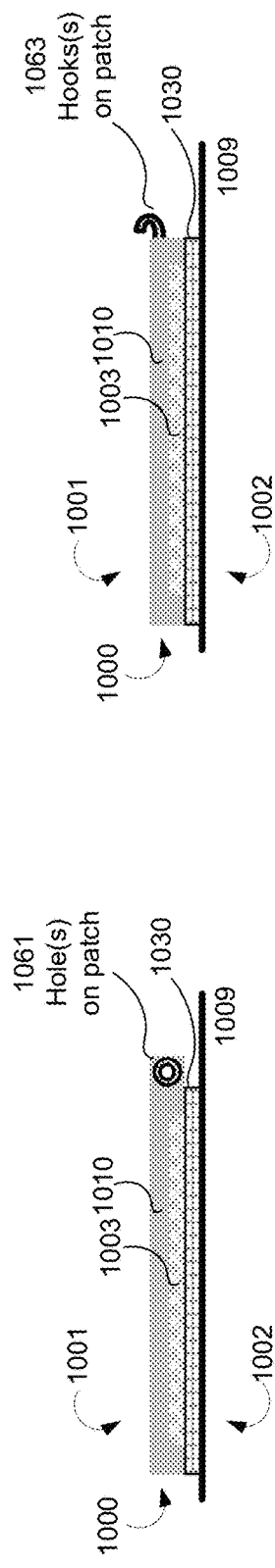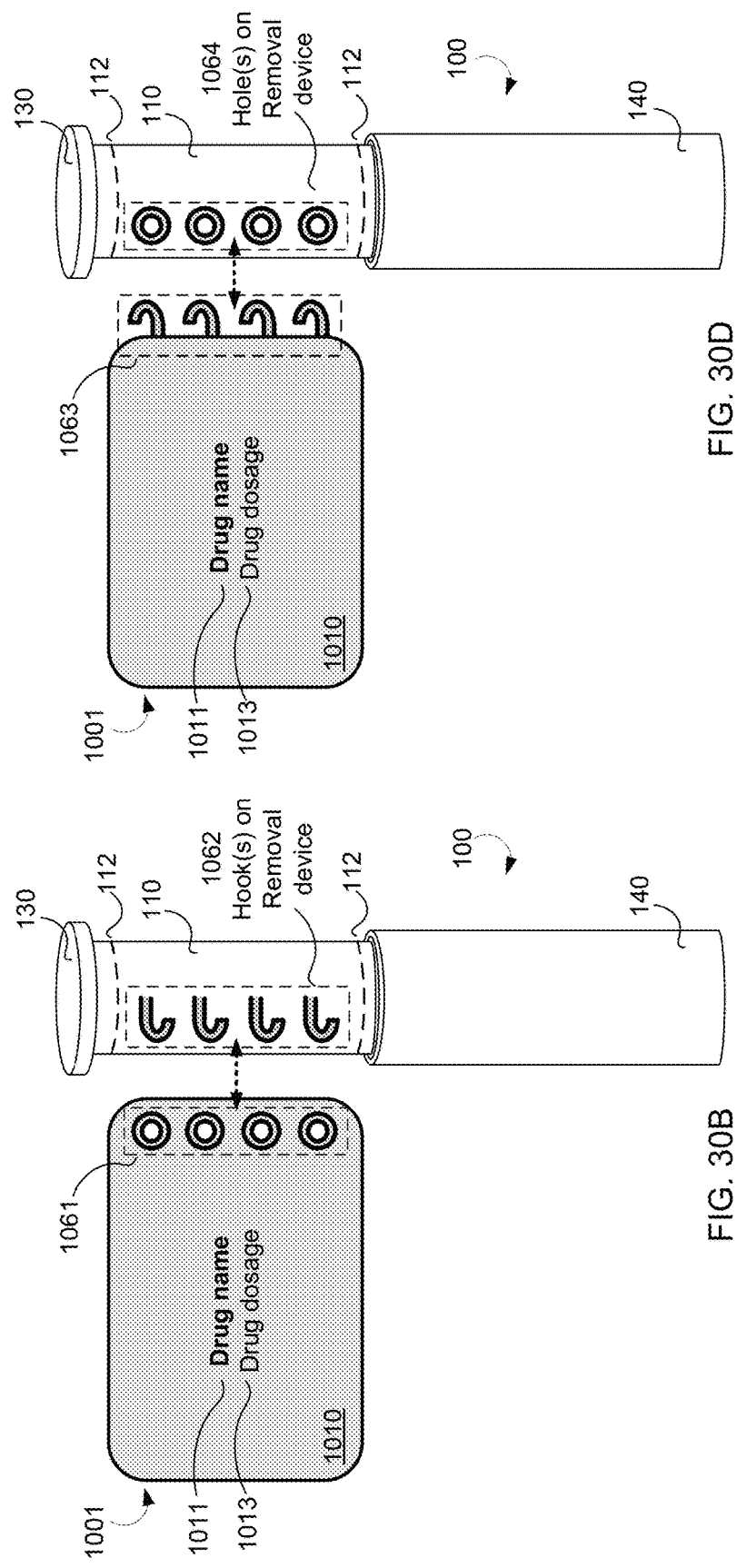

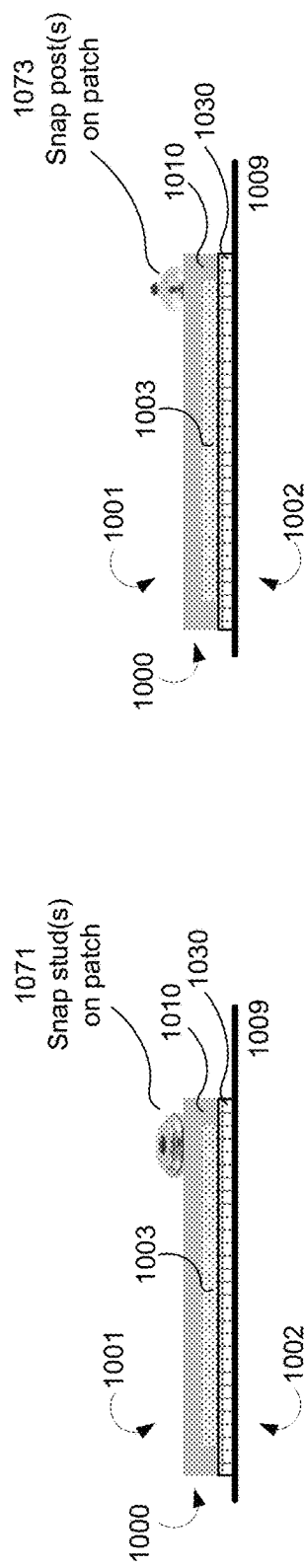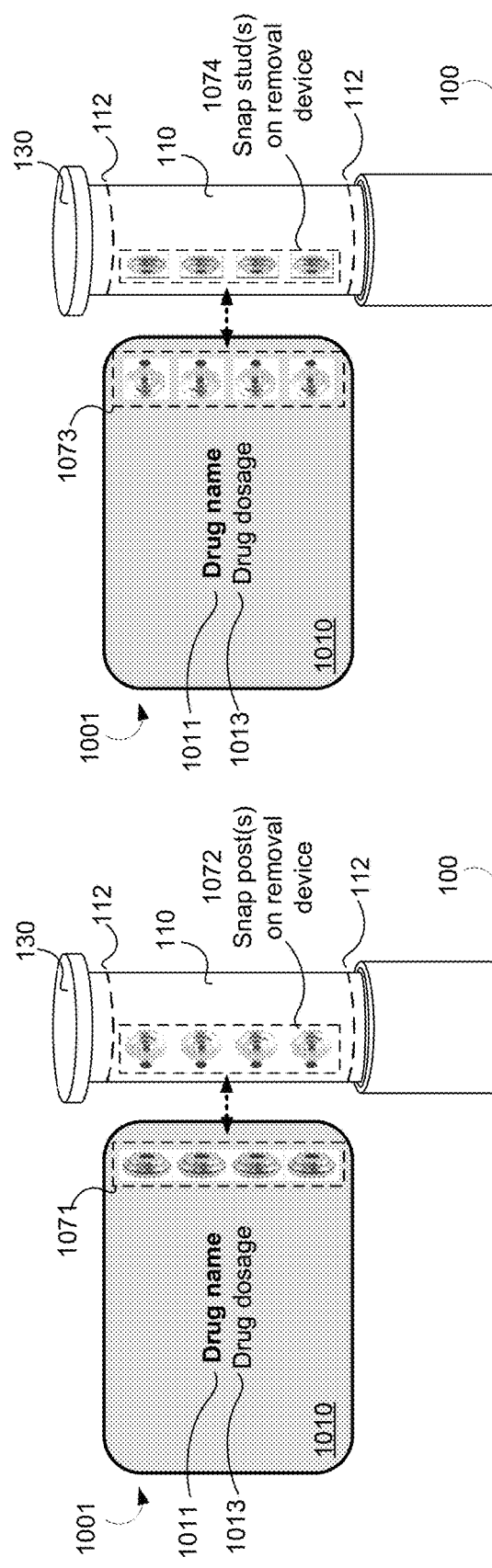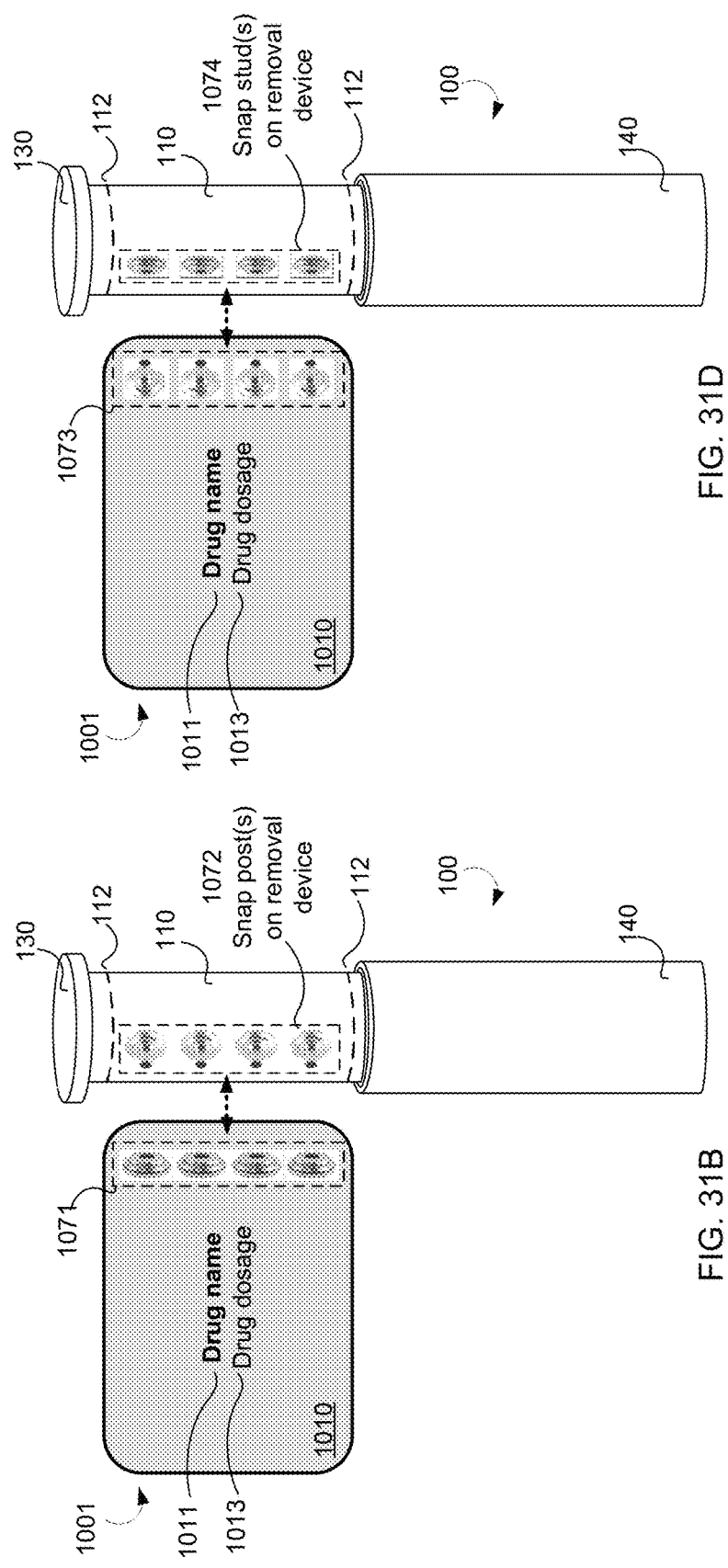

SYSTEMS AND METHODS FOR REMOVING A COVERING FROM A BODILY SURFACE

CROSS-REFERENCE

This application is a continuation of International Application No. PCT/US19/42059, filed Jul. 16, 2019, which claims the benefit of U.S. Provisional Patent Application No. 62/699,505, filed Jul. 17, 2018, U.S. Provisional Patent Application No. 62/711,872, filed Jul. 30, 2018, and U.S. Provisional Patent Application No. 62/728,595, filed Sep. 7, 2018, each of which is entirely incorporated herein by reference.

BACKGROUND

Diversion of prescription medications (e.g., controlled substances such as opioids and other pharmaceuticals) for illicit purposes, unintended uses and accidental exposures can lead to medical issues (e.g., fetal exposure from maternal substance uses), hospitalization and even death. The prescription medications can be administered in multiple forms, including oral drugs, injectable drugs, and transdermal patches. The diversion of prescription medications can account for about 30 percent (%) of the overall drug problem in the United States. Furthermore, the diversion of prescription medications can cost billions of dollars of economic burden in areas including law enforcement, health care, social services, and court costs. In some cases, opioid diversion through theft or unlawful distribution can cost over $70 billion to insurers and employers. In such a case, the employers can be adversely affected by lack of productivity, absence and/or carelessness of employees with substance abuse issues.

The diversion of prescription medications can be related to lack of compliance by patients, family members and/or medical practitioners (e.g., healthcare providers). In some cases, practitioners can tamper with retrieved transdermal patches to extract, use and/or distribute residual pharmaceuticals (e.g., fentanyl). In some cases, approximately 15% of pharmacists, approximately 10% of nurses and/or approximately 8% of physicians can be involved in the diversion and/or illicit distribution of prescription medications for non-prescription (e.g., recreational) uses. Practitioners with knowledge and access to such prescription medications may tamper with their storage means (e.g., containers or vessels) or treatment vehicles (e.g., transdermal patches) to extract, use, and/or distribute residual pharmaceuticals.

Current methods of monitoring controlled substances include using controlled medical dispensing systems (e.g., requiring thumbprint of the practitioner) and/or tracking the controlled substances from a subject's bodily fluid (e.g., urine or blood). Other examples include the "honor system" of retrieval, disposal and destruction of storage/treatment means, as well as physical or electronic surveillance in areas within the hospital (e.g., patient rooms, medication rooms, nursing stations) or other relevant institutions (e.g., pharmacies).

SUMMARY

There is a need for improved tracking of prescription medications pre-administration, post administration, and pre-destruction (e.g., prior to the destruction of wasted or refused medications). The systems and methods disclosed herein can provide closed loop tracking of prescription medications, for example the tracking and retrieval of used transdermal patches for dispensing prescription medications. The present disclosure provides device configurations and methods to remove, secure, and/or track delivery means (e.g., transdermal patches) of prescription medications prior to their use, subsequent to their use, and prior to their destruction or disposal.

An aspect of the disclosure provides a method of selectively removing a covering from a bodily surface of a subject. The method may comprise: (a) applying a covering removal device to a portion of the covering disposed on the bodily surface of the subject, thereby generating a connection between the covering removal device and the portion of the covering; and (b) moving the covering removal device across the bodily surface of the subject in order to selectively remove the covering from the bodily surface and capture the covering onto the covering removal device, without the covering removal device substantially affecting or interfering with the bodily surface of the subject.

In some embodiments, the covering removal device may comprise an adhesive material to generate the connection between the covering removal device and the portion of the covering. In some cases, a first binding strength between the adhesive material and the covering may be greater than a second binding strength between the covering and the bodily surface underneath the covering. In other cases, a first binding strength between the adhesive material and the covering may be greater than a second binding strength between the adhesive material and an additional bodily surface of the subject adjacent to the covering. In some instances, the adhesive material may not generate a connection with the bodily surface of the subject. The adhesive material can be a solid, semi-solid, or gel. The covering removal device can be a roller. The pulling may comprise rolling of the covering removal device over the covering.

In some embodiments, the covering may be pre-medicated with a drug. In other cases, the covering may not be pre-medicated. In some embodiments, the covering may further comprise an additional covering, wherein the covering may be disposed over an additional covering adjacent to the bodily surface of the subject.

The covering removable device may comprise a housing coupled to a releasable core comprising the adhesive material. The releasable core can be configured to be released from the housing.

In some embodiments, the method may further comprise releasing the releasable core from the housing and coupling an additional releasable core to the housing. In some embodiments, at least a portion of the releasable core may be flat, and the method may further comprise, in (a), applying the at least the portion of the releasable core to the portion of the covering disposed on the bodily surface of the subject.

In some embodiments, the covering removal device may be operatively coupled to a source of a neutralizer, and the method may further comprise, subsequent to (b), using the neutralizer from the source of the neutralizer to neutralize any excess drug in the covering or an additional covering coupled to the covering.

In some embodiments, the source of the neutralizer may be a part of the covering removal device. In some cases, the source of the neutralizer may be detachable from the covering removal device. In some instances, the neutralizer can be configured to (i) encapsulate the controlled substance and/or (ii) deactivate the controlled substance. The source of the neutralizer can be a container configured to hold the neutralizer. Alternatively, the source of the neutralizer can be a film configured to cover at least a portion of the covering.

In some embodiments, the method may further comprise, prior to (a), coupling a handle to the covering removal device. The method may further comprise, subsequent to (b), removing the handle from the covering removal device.

Another aspect of the disclosure provides a covering removal device for selectively removing a covering from a bodily surface of a subject. The covering removal device may comprise: a base structure; and an adhesive material coupled to the base structure, wherein the adhesive material aids in generating a connection between the covering removal device and the covering disposed on the bodily surface of the subject, wherein the covering removal device is configured to be moved across the bodily surface of the subject in order to selectively remove the covering from the bodily surface and capture the covering onto the covering removal device, without the covering removal device affecting or interfering with the bodily surface of the subject.

In some embodiments, a first binding strength between the adhesive material and the covering may be greater than a second binding strength between the covering and the bodily surface underneath the covering. In some cases, a first binding strength between the adhesive material and the covering may be greater than a second binding strength between the adhesive material and an additional bodily surface of the subject adjacent to the covering. In some cases, the adhesive material need not generate a connection with the bodily surface of the subject.

In some embodiments, the adhesive material can be a solid, semi-solid, or gel. The base structure can be a movable base structure. The movable base structure may comprise a roller, and wherein an outwardly facing surface of the roller may comprise the adhesive material.

In some embodiments, the covering may be pre-medicated with a drug. In other cases, the covering need not be pre-medicated. In some embodiments, the covering may further comprise an additional covering, wherein the covering may be disposed over an additional covering adjacent to the bodily surface of the subject. In some embodiments, the device may further comprise a housing coupled to the base structure, wherein the base structure may be configured to be released from the housing. The housing can be configured to release the base structure and couple to an additional removable base structure. In some embodiments, at least a portion of the base structure may be flat.

In some embodiments, the covering removal device may be operatively coupled to a source of a neutralizer. The neutralizer can be configured to neutralize any excess drug in the covering or an additional covering coupled to the covering. In some cases, the source of the neutralizer may be a part of the covering removal device. In other cases, the source of the neutralizer can be detachable from the covering removal device. The neutralizer can be configured to (i) encapsulate the controlled substance and/or (ii) deactivate the controlled substance. The source of the neutralizer can be a container configured to hold the neutralizer. Alternatively, the source of the neutralizer can be a film configured to cover at least a portion of the covering.

In some embodiments, the device may further comprise a removable handle configured to be coupled to the base structure.

A kit comprising the device of any of the aforementioned embodiments may be provided. The kit may comprise (i) a pair of the housing and the base structure and (ii) the removable handle. In some embodiments, the kit may comprise the source of the neutralizer. The source of the neutralizer may be a part the housing. The source of the neutralizer may be configured to couple to the housing. In some embodiments, the kit may further comprise a plurality of the pair of housing and base structure.

Another aspect of the disclosure provides a device for aiding removal, securing, and closed loop tracking of a controlled substance. The device may comprise: a housing; and an extendable core that may be operably coupled to the housing and movable relative to the housing, wherein the core can be configured to extend from the housing, and the extended core may be usable to aid a user in removing a transdermal patch comprising the controlled substance from a subject, and wherein the core with the removed transdermal patch can be further configured to retract into the housing, to thereby secure the transdermal patch within the housing in order to inhibit diversion of the controlled substance.

In some embodiments, the housing may further comprise one or more external windows that selectively display information upon securing of the transdermal patch within the housing. The information can be selectively displayed on the housing comprises one or more of the following: (a) one or more landing zones that are configured to indicate a dimension of the transdermal patch; (b) a machine readable code corresponding to the device; (c) one or more writable areas for the user to record (i) the user's name, (ii) time, date and/or location of securing of the transdermal patch, (iii) transdermal patch dose and/or (iv) a location of the transdermal patch on the subject; and (d) a chemical indicator that is configured indicate a presence of the controlled substance in the transdermal patch.

In some embodiments, the device may comprise one or more neutralizing elements in the core or the housing. The one or more neutralizing elements can be configured to aid in neutralization or chemical treatment of the transdermal patch. The information may comprise one or more graded bars that indicate a remaining concentration of the controlled substance on the patch.

A further aspect of the disclosure provides a transdermal patch. The patch may comprise: (a) a cover; (b) a carrier comprising a medication; (c) an adhesive configured to adhere on a bodily surface of a subject; and (d) a connection mechanism adjacent to the cover, wherein the connection mechanism can be configured to generate a connection between the patch and a patch removal device.

In some embodiments, the connection mechanism may include one or more components of a male-to-female fastener, a tether, an adhesive, a metal piece, and a magnet. In some cases, a first binding strength of the connection between the patch and the device may be greater than a second binding strength between the patch and the bodily surface of the subject. In some embodiments, the cover may comprise a machine readable code corresponding to the patch. In some embodiments, the patch may further comprise an indicator that indicates detachment of the patch from the bodily surface of the subject.

A method of removing a transdermal patch is provided in another aspect of the disclosure. The method may comprise: (a) providing the transdermal patch on a bodily surface of a subject, the patch comprising: (i) a cover; (ii) a carrier comprising a medication; (iii) an adhesive configured to adhere on a bodily surface of a subject; and (iv) a connection mechanism adjacent to the cover, and (b) generating a connection between the patch and a patch removal device by using the connection mechanism.

In some embodiments, the connection mechanism may include one or more components of a male-to-female fastener, a tether, an adhesive, a metal piece, and a magnet. In some cases, a first binding strength of the connection between the patch and the device may be greater than a second binding strength between the patch and the bodily surface of the subject. In some embodiments, the cover may comprise a machine readable code corresponding to the patch. In some embodiments, the patch may further comprise an indicator that indicates detachment of the patch from the bodily surface of the subject.

A method for tracking a transdermal patch is provided in another aspect of the disclosure. The method may comprise: (a) scanning a first identifier of the transdermal patch and a second identifier of a subject; (b) obtaining, with aid of a computer processor and based on the scanning, (i) a predetermined medication time for which the transdermal patch is to be applied to the subject; and (ii) a duration of time for which the transdermal patch is being applied to the subject; and (c) if the duration of time meets a predetermined threshold, displaying a message on an electronic device an instruction to remove the transdermal patch from the subject.

In some embodiments, the predetermined threshold may be within at most 2 hours from the predetermined medication time. In some cases, the predetermined threshold may be within at most 1 hour from the predetermined medication time. In some cases, the predetermined threshold may be within at most 30 minutes from the predetermined medication time.

In some embodiments, the method may further comprise obtaining, with aid of the computer processor and based on the scanning, a predetermined time at which the transdermal patch is to be applied to the subject. In embodiments, the method may further comprise obtaining, with aid of the computer processor and based on the scanning, a time at which the transdermal patch is applied to the subject.

In some embodiments, the method may further comprise removing the transdermal patch from the subject. In some cases, the method may further comprise obtaining, with aid of the computer processor and based on the scanning, a time of removal of the transdermal patch from the subject. In some cases, the method may further comprise retrieving the removed transdermal patch in a collection device. In some cases, the method may further comprise scanning a third identifier of the collection device.

In some embodiments, the method may further comprise updating date, time, and/or location of the scanning of the first identifier and/or the second identifier in a database. In some embodiments, the method may comprise scanning a fourth identifier of a practitioner responsible for (i) application of the transdermal patch to the subject and/or (ii) removal of the transdermal patch from the subject. In some cases, the method may comprise updating date, time, and/or location of the scanning of the fourth identifier in a database.

In some embodiments, the transdermal patch may be pre-medicated. In some embodiments, the transdermal patch may not be pre-medicated.

In some embodiments, the transdermal patch may be tracked pre-administration to the subject, during administration to the subject, and/or post-administration to the subject. In some embodiments, the transdermal patch may be tracked prior to usage of the transdermal patch, post-usage of the transdermal patch, prior to disposal of the used transdermal patch, during disposal of the used transdermal patch, and/or post-disposal of the used transdermal patch.

Another aspect of the disclosure provides a non-transitory computer readable medium comprising machine executable code that, upon execution by one or more computer processors, implements any one of the subject methods of the disclosure.

A further aspect of the disclosure provides a system comprising one or more computer processors and computer memory coupled thereto, wherein the computer memory comprises machine executable code that, upon execution by the one or more computer processors, implements any one of the subject methods of the disclosure.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 1A is a schematic view of a patch removal/tracking device in an extended configuration, in accordance with an embodiment;

FIG. 1B is a schematic view of a patch removal/tracking device in a retracted configuration, in accordance with an embodiment;

FIGS. 2A through 2E are schematic illustrations showing the retrieval of a transdermal patch from a subject using a patch removal/tracking device, in accordance with an embodiment;

FIG. 3A is a schematic view of a patch removal/tracking device, showing a patch that is retrieved by the device, in accordance with an embodiment;

FIGS. 3B and 3C are schematic views of a patch removal/tracking device, showing various spacing mechanisms within the device, in accordance with some embodiments;

FIGS. 4A through 4F are cross-sectional views of a patch removal/tracking device, showing various spacing mechanisms within the device, in accordance with some embodiments;

FIGS. 5A through 5E are schematic views of a patch removal/tracking device, showing different components of the device, in accordance with some embodiments;

FIG. 10 is a schematic view of a covering removal device to selectively remove a covering from a subject's skin, in accordance with an embodiment;

FIGS. 11A through 11G are schematic side views of a covering removal device being used to selectively remove a covering from a subject's skin, in accordance with some embodiments;

FIGS. 13A through 13F are schematic illustrations showing a one-piece covering removal device to selectively remove a covering from a subject's skin, in accordance with some embodiments;

FIGS. 14A through 14G are schematic illustrations showing a two-piece covering removal device to selectively remove a covering from a subject's skin, in accordance with some embodiments;

FIGS. 15A through 15D are schematic illustrations showing a different two-piece covering removal device to selectively remove a covering from a subject's skin, in accordance with some embodiments;

FIGS. 16A through 16H are schematic illustrations showing a refillable covering removal device with a housing and a refillable core cartridge, in accordance with some embodiments;

FIG. 17 is a schematic illustration of one or more components of a covering removal device, in accordance with an embodiment;

FIGS. 18A through 18F are schematic illustrations of systems and methods of using a device to remove a covering from a subject, in accordance with some embodiments;

FIGS. 19A through 19G are schematic illustrations of systems and methods of using a different device to remove a covering from a subject, in accordance with some embodiments;

FIGS. 20A through 20M are schematic illustrations of systems and methods of using a different device to remove a covering from a subject, in accordance with some embodiments;

FIGS. 21A through 21C are schematic illustrations of systems and methods of using a different device to remove a covering from a subject in accordance with some embodiments;

FIGS. 22A through 22C are schematic illustrations of systems and methods of using a different device to remove a covering from a subject, in accordance with some embodiments;

FIGS. 23A through 23H are schematic illustrations of systems and methods of using a different device to remove a covering from a subject, in accordance with some embodiments;

FIGS. 24A through 24F are schematic illustrations of patches that are adhered to a subject's skin, in accordance with some embodiments;

FIGS. 25A through 25D are schematic illustrations of patches with an identifier, in accordance with some embodiments;

FIGS. 26A through 26C are schematic illustrations of a patch with a patch removal mechanism, in accordance with some embodiments;

FIGS. 27A through 27C are schematic illustrations of a patch with a different patch removal mechanism, in accordance with some embodiments;

FIGS. 28A and 28B are schematic views of a patch that includes one or more patch removal indicators, in accordance with some embodiments;

FIGS. 29A through 29D are schematic illustrations of a patch and a patch removal device with a Velcro™ strip as a patch removal mechanism, in accordance with some embodiments;

FIGS. 30A through 30D are schematic illustrations of a patch and a patch removal device with hook(s) and hole(s) as a patch removal mechanism, in accordance with some embodiments;

FIGS. 31A through 31D are schematic illustrations of a patch and a patch removal device with snap stud(s) and snap post(s) as a patch removal mechanism, in accordance with an embodiment;

DETAILED DESCRIPTION

Figure 6:
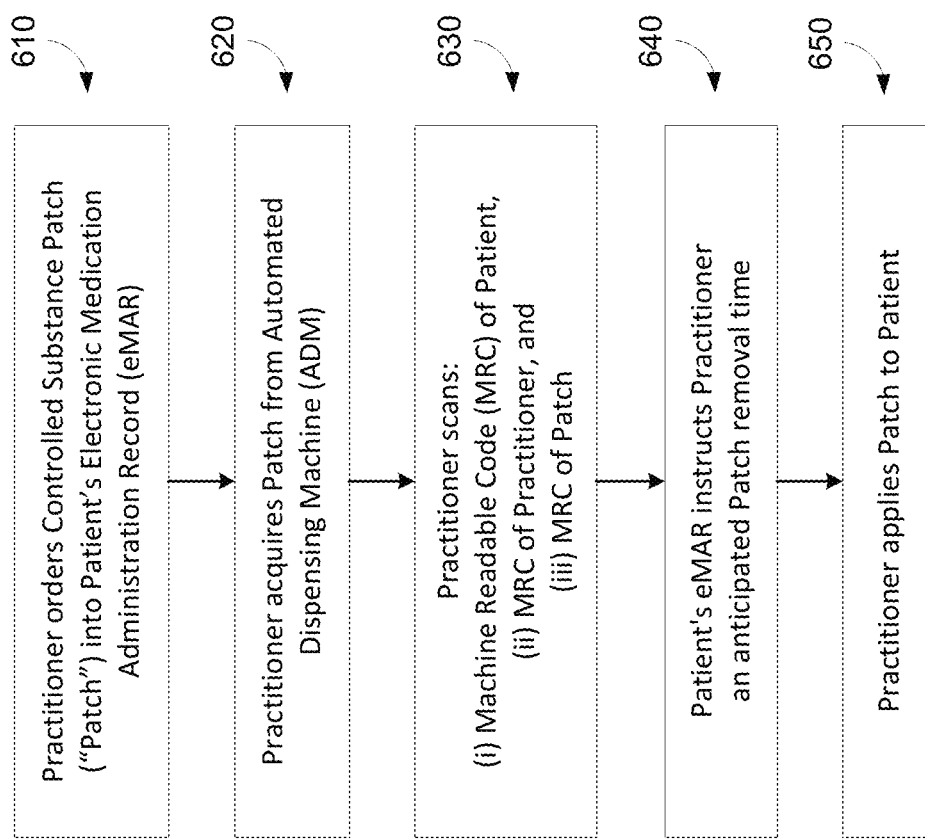
FIG. 6 is a flowchart illustrating a method of administering a controlled substance transdermal patch to a subject, in accordance with an embodiment.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used herein, the singular forms "a," "an," and "the" include plural references unless the context clearly dictates otherwise. Any reference to "or" herein is intended to encompass "and/or" unless otherwise stated.

Whenever the term "at least," "greater than," or "greater than or equal to" precedes the first numerical value in a series of two or more numerical values, the term "at least," "greater than" or "greater than or equal to" applies to each of the numerical values in that series of numerical values.

For example, greater than or equal to 1, 2, or 3 is equivalent to greater than or equal to 1, greater than or equal to 2, or greater than or equal to 3.

Whenever the term "at most", "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The terms "covering" and "layer," as used interchangeably herein, generally refers to an object that is to be adhered to a bodily surface of a subject, and removed after a period of time. The covering may comprise an adhesive material to connect (e.g., adhere, attach, bind) to the bodily surface of the subject. The covering may not be pre-medicated. The covering may be pre-medicated (e.g., a transdermal patch comprising a drug). The covering may comprise patches, pads, films, dressings, plasters, bandages, wrappers, strips, patches, gauzes, tapes, and the like that adheres to a bodily surface (e.g., healthy and/or wounded skin) of a subject. In some cases, the covering may be disposed over an additional covering that is adhered to the bodily surface (e.g., a pre-medicated patch) or an object (e.g., a needle assembly, such as an intravenous needle), thereby to protect the additional covering or the object (e.g., from damage, unintentional removal, etc.).

The covering may be flexible and/or stretchable. The covering may be transparent, semi-transparent, opaque, or not transparent. The thickness of the covering may be at least about 0.01 mm, 0.02 mm, 0.03 mm, 0.04 mm, 0.05 mm, 0.06 mm, 0.07 mm, 0.08 mm, 0.09 mm, 0.1 mm, 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, or more. The thickness of the covering may be at most about 5 mm, 4 mm, 3 mm, 2 mm, 1 mm, 0.9 mm, 0.8 mm, 0.7 mm, 0.6 mm, 0.5 mm, 0.4 mm, 0.3 mm, 0.2 mm, 0.1 mm, 0.09 mm, 0.08 mm, 0.07 mm, 0.06 mm, 0.05 mm, 0.04 mm, 0.03 mm, 0.02 mm, 0.01 mm, or less.

Examples of the covering include BAND AID®, TEGADERM™ TRANSPARENT DRESSING, NEXCARE™, ADVANCED CURAD™, AQUA-PROTECT™, and modifications thereof. In some embodiments, examples of the covering include transdermal patches, such as DuoFilm®, Durageisc®, Butrans®, Evra®, etc.

Overview

Coverings (e.g., transdermal patches) may be applied to a bodily surface of a subject for a variety of applications (e.g., medical applications). The coverings may be applied to a skin of a subject. The coverings (e.g., bandages, such as BANDAID®) can cover a wound on the skin. In some cases, the coverings may be transdermal patches that are pre-medicated. Transdermal patches can be used as a cosmetic, topical, and/or transdermal delivery system (TDS). In some examples, a TDS can be designed to deliver a drug (e.g., a therapeutic drug) onto a subject's body (e.g., a patient's skin). In some cases, the drug can cross the skin of the patient into the bloodstream of the patient. The TDS can deliver a therapeutically effective amount of the drug. The TDS can include a protective layer, a drug carrier (e.g., a liquid, gel, or solid matrix, a membrane, a pressure sensitive membrane, etc.), and an adhesive to adhere to the patient's skin. In some cases, the drug carrier can be the adhesive.

Examples of drugs that can be delivered via the TDS and its therapeutic application include scopolamine for motion sickness, nitroglycerin for angina, clonidine for hypertension, and estradiol for female hormone replacement therapy. Other examples of the drug include, but are not limited to, methylphenidate, selegiline, rivastigmine, rotigotine, granisteron, buprenorphine, oestrodiol, fentanyl, nicotine, testosterone, etc. Other examples of therapeutic applications include, but are not limited to, attention deficit hyperactivity disorder, urologic issues, erectile dysfunction, dermatologic conditions, migraine, other types of acute and chronic cephalgia, Parkinson's disease, restless leg syndrome, pain management, etc.

Removal (e.g., peeling) of the coverings from the bodily surface of the subject can cause complications (e.g., abrasions). In some cases, manually (e.g., by hand) peeling the covers can cause abrasions on the skin (e.g., on the skin adjacent to the covers). In some cases, residual drugs can exist within the pre-medicated covers (e.g., TDS) after usage (e.g., after a prescribed duration on the patient's skin). The residual drugs can be at the protective layer-drug carrier interface, within the drug carrier, or within the adhesive. In some examples, between about 25 percent (%) and 90% of originally contained fentanyl can remain within a fentanyl patch after a 72 hours use. Such presence of the residual drugs can be hazardous to the patient, a person removing the TDS from the skin of the patient (e.g., healthcare providers), and/or other third parties (e.g., a family member or a pet of the patient). In an example, an improper or unsuccessful removal of the patch can lead to an unintended exposure of the residual drugs to an unintended site (e.g., hands, eyes, other exposed bodily areas, or clothing) at a potentially toxic or lethal amount.

In some cases, gloves can be worn while removing the TDS from the skin. However, gloves or not, an unsuccessful removal of the TDS (e.g., excessive stretching or tearing of the TDS) can still lead to an unintended exposure of the residual drugs (e.g., via leak or spill from the TDS). A standard medical tool such as a tweezer can be used to remove the TDS from the patient's skin, but without a proper disposal of the tweezer, a secondary use of the tweezer can also lead to an untended exposure of the residual drugs.

In view of the foregoing, there exists a considerable need for alternative systems and methods for removal of coverings (e.g., plasters, TDS) from the subject's skin. The systems and methods disclosed herein can provide a removal (e.g., a complete removal) of the coverings without complications, such as abrasions on the skin or tearing of the coverings. In some cases, the present disclosure provides systems and methods of removing transdermal patches from the subject's skin. The systems and methods disclosed herein can provide neutralization of the residual drugs in the transdermal patches upon their removal. The present disclosure can provide configurations and methods to track, remove, and/or neutralize transdermal patches of medications subsequent to their use using a patch removal device.

Systems and Methods for Removing a Covering

In an aspect, the present disclosure provides apparatus and methods for providing improved mechanisms of removing a covering from a bodily surface of a subject using a covering removal device. The apparatus and methods may provide mechanisms of selectively removing the covering from the bodily surface of the subject using the device. The apparatus and methods may provide mechanisms of tracking the covering, prior to, during, and subsequent to a use of the covering on the bodily surface of the subject. In some cases, the present disclosure provides apparatus and methods for providing improved mechanisms of removing a transdermal patch (herein referred to as a "patch") by using a patch removal device (herein referred to as a "device"). The transdermal patch may be pre-medicated (e.g., with a drug). The device may further be used for the tracking of used patches for dispensing of residual medications (e.g., controlled substances) contained within the patches.

The medications to be administered via the covering may be prescription medications (e.g., controlled substances) or non-prescription drugs. The medications may be pharmaceuticals or nutraceuticals. The medications may include any other therapeutic treatment modalities using passive or active treatment methodologies. The medications may be any other compounds (natural, synthetic, modified natural, or combinations thereof) that is to be delivered on a bodily surface of a subject (e.g., a patient's skin). In some cases, the medications may permeate into the body of the subject (e.g., in the skin or the bloodstream of the patient).

The controlled substances administered via the patch can include opiate and opioids, as well as central nervous system (CNS) depressants and stimulants. Examples of opioids include morphine, codeine, thebaine, oripavine, morphine dipropionate, morphine dinicotinate, dihydrocodeine, buprenorphine, etorphine, hydrocodone, hydromorphone, oxycodone, oxymorphone, fentanyl, alpha-methylfentanyl, alfentanil, trefantinil, brifentanil, remifentanil, octfentanil, sufentanil, carfentanyl, meperidine, prodine, promedol, propoxyphene, dextropropoxyphene, methadone, diphenoxylate, dezocine, pentazocine, phenazocine, butorphanol, nalbuphine, levorphanol, levomethorphan, tramadol, tapentadol, anileridine, any functional variant thereof, and any functional combinations thereof. Examples of CNS depressants and stimulants include methylphenobarbital, pentobarbital, diazepam, clonazepam, chlordiazepoxide, alprazolam, triazolam, estazolam, any functional variant thereof, and any functional combinations thereof.

Various components of the covering (e.g., the patch) or the device can include biologically acceptable and/or compatible materials suitable for medical applications, depending on the particular application and/or preference of a medical practitioner. For example, components of the covering or the device can include or be fabricated from materials such as polyvinyl chloride, polyvinylidene chloride, low density polyethylene, linear low density polyethylene, polyisobutene, poly(ethylene-vinylacetate) copolymer, lightweight aluminum foil and combinations thereof, stainless steel alloys, commercially pure titanium, titanium alloys, silver alloys, copper alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKEL-ITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaS04 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, glass, and combinations thereof.

Various components of the covering or the device may have material composites, including one or more of the above materials, to achieve various desired characteristics such as strength, rigidity, elasticity, compliance, biomechanical performance, and/or durability. The components of the covering or the device, individually or collectively, may also be fabricated from a heterogeneous material such as a combination of two or more of the above-described materials. The components of the covering or the device may be monolithically formed or integrally connected.

Prior to use, the covering (e.g., patch) or device can be contained in a storage area inside or outside of a medication room (e.g., a hospital room where the covering would be applied to or removed from a patient). The covering or device may be in a container (e.g., a box). The container may be dedicated to storing the covering or device only. Such container for the covering or device may be on a table, a cabinet, or a wall.

In some cases, the covering or the device can be stored in an automated dispensing machine (ADM) (commercially available ADMS include, for example the McLaughlin dispensing system, the Baxter ATC-212 dispensing system, and the Pyxis MedStation). In some embodiments, one or more of the coverings or devices disclosed herein can be stored in a drawer of the ADM (e.g., a CUBIE pocket in the Pyxis MedStation). The drawer, the ADM, and/or the room containing the ADM can be temperature controlled (e.g., to a preset or selected average temperature) to prevent various components of the coverings (and the incorporated drug) or device from damage (e.g., degradation) and to enhance its shelf-life.

The covering or the device disclosed herein can be packaged using any suitable forms of packaging. The packaging can protect the covering or the device from damage and/or to enhance its shelf-life. The patch (prior to or subsequent to incorporating a drug into the covering), the packaging or the covering, the device, and/or the packaging of the device can be sterilizable to allow them to be sterilized for medical use.

The covering, the packaging of the covering, the device, or the packaging of the device can have an identifier (e.g., a machine readable code (MRC) or an identification device) for identification or tracking. In some cases, the identifier may be used for covering tracking (e.g., patch tracking), personal linking (e.g., recording identification of practitioner(s) responsible for application and/or removal of the covering), patient linking, device tracking, pharmacy tracking (e.g., distributing the covering, receiving the device containing the covering, and/or destroying the device containing the covering), etc. In some cases, the identifier can be a unique covering identifier (UCI) (e.g., a unique patch identifier (UPI)) that is specific to the covering and/or the packaging of the covering. The MRC may be a barcode (e.g., a linear barcode, a matrix barcode, etc.). The identification device may be a communications device, such as a radio frequency device (e.g., a radio-frequency identification (RFID) system, a near-field communication (NFC) system, improvements thereof, etc.) or other internal integrated circuits. The identification device may be an electronic chip. In some cases, the packaging of the device may include the identifier, which can be scanned during (i) loading to the ADM for storage and/or (ii) unloading from the ADM for usage. In some cases, the covering may include the identifier, which can be scanned prior to (i) application of the covering to the subject and/or (ii) removal of the covering from the subject. In some examples, such identifier may be scanned, recorded, and tracked by a system (e.g., electronic medication administration record (eMAR)). The identifier on the covering and the identifier on the covering's packaging may be the same or different.

An identifier of the present discloser may be scanned by an identifier reader, such as a barcode reader, RFID reader, a NFC reader, etc. In some cases, the identifier reader may be a device in digital communication with a machine (e.g., a computer with a processor) configured to read and identify the identifier. In some cases, the identifier reader may be a personal device (e.g., a smart phone with a camera) that is in digital communication (e.g., a wireless communication) with the machine. In some cases, the identifier reader may be used by a practitioner (e.g., a nurse). In some cases, the identifier reader may be used by a user of the covering.

Subsequent to use (e.g., after a predetermined or prescribed duration) on a subject's skin (e.g., a patient's skin), the covering (e.g., bandage, patch) can be removed from the skin by using the device. To remove the covering, an attachment zone of the device can be brought in contact with a corresponding attachment zone of the covering (e.g., a side of a bandage opposite the skin or a portion of a "nonactive" side of the patch that is opposite the subject's skin). The initial contact between the attachment zones of the device and the covering can be secured using any means of connection mechanism that is present in the attachment zones, for example, various male-to-female fastener (e.g., mating or interlocking fasteners, hooks and holes, hooks and loops such as Velcro™, etc.), linear closure devices (e.g., a zipper, a zip-lock with or without a slider, etc.) tethers (e.g., string tethers), adhesives (e.g., solids, semi-solids, gels, viscous liquids, etc.), magnets, and other grasping mechanisms.

In some cases, the device may be designed for a left-handed use, e.g., designed to be held by a left hand when using the device to remove a covering (e.g., a patch) from a subject. In some cases, the device may be designed for a right-handed use, e.g., designed to be held by a right hand when using the device to remove the covering. Systems and methods of using the device for the left-handed use may utilize various aspects of systems and methods of using the device for the right-handed use, with one or more aspects (e.g., direction of rotation of the device or a core of the device across the covering, alignment of the device to the patch, etc.) being opposite or inverted with respect to those for the right-handed use. In some cases, the device may be compatible to be used by both the left hand and the right hand.

In some cases, the device may have a first connection mechanism, the covering may have a second connection mechanism, and the first and second connection mechanisms may pair (e.g., male-to-female fasteners) to create a connection between the device and the covering. In some cases, the device may have a first connection mechanism, the covering may have a second connection mechanism, but the first connection mechanism and the second connection mechanism may not connect (or interact or overlap) with each other upon generating the connection between the device and the covering. In such a case, the first connection mechanism of the device may generate a connection (e.g., bind) with a portion of the covering that does not comprise the second connection mechanism. Similarly, the second mechanism of the covering may generate a connection with a portion of the device that does not comprise the first connection mechanism. In some cases, only the device may have the connection mechanism that is sufficient to create the connection between the device and the covering. In some cases, only the covering may have the connection mechanism that is sufficient to create the connection between the device and the covering. In such a case, the covering's connection mechanism operable to adhere to the device may be covered (e.g., by a removable sheet) prior to removal of the covering from the skin.

Covering Remover

The device can have various shapes and sizes. In some cases, a device may be in the shape of a sphere, cuboid, or disc, or any partial shape or combination of shapes thereof. The device may have a cross-section that is circular, triangular, quadrilateral (e.g., square, rectangle, rhombus, trapezoid, parallelogram, etc.), pentagonal, hexagonal, or any partial shape or combination of shapes thereof. The device may have two or more cross-sections that are different. In an example, a cross-section of at least a portion of the device may have a flat region and a non-flat region. The flat region may be configured to enhance/maximize a contact point or connection strength between the device (e.g., an adhesive on the device) and the covering (e.g., the patch). In such a case, the cross-section of at least the portion of the device may be a partial circle, oval, or ellipse with a flat edge (e.g., a D-shape or semi-circular cross-section).

In some cases, a perimeter of the cross-section of the device may comprise a flat region and a non-flat region (i.e., a curved region), and the flat region may be less than, equal to, or greater than 50% of the perimeter of the cross-section of the device. The flat region may be at least 5%, 10%, 15%, 20%, 25%, 30%, 35%, 40%, 45%, 50%, or more of the perimeter of the cross-section of the device. The flat region may be at most 50%, 45%, 40%, 35%, 30%, 25%, 20%, 15%, 10%, 5%, or less of the perimeter of the cross-section of the device.

In some cases, the cross-section of the device may be a segment (e.g., a major segment) of a circle, wherein an arc of the segment of the circle is intercepted by a chord (e.g., a flat line). In some cases, the cross-section of the device may be a major segment of a circle that is bounded by (1) the chord and (2) the major arc of the circle that is intercepted by the chord. In some examples, a length of the chord may be less than a diameter of the circle. The length of the chord may be at least 5%, 10%, 20%, 30%, 40%, 50%, 60%, 70%, 80%, 90%, 95%, or more of the diameter of the circle. The length of the chord may be at most 95%, 90%, 80%, 70%, 60%, 50%, 40%, 30%, 20%, 10%, 5%, or less of the diameter of the circle. In some examples, the cross-section may be the major segment of the circle, and the arc (i.e., a major arc) of the major segment may be longer than 50% of the circumference of the circle. The major arc of the major segment may be at least 55%, 60%, 65%, 70%, 75%, 80%, 85%, 90%, 95%, or more of the circumference of the circle. The major arc of the major segment may be at most 95%, 90%, 85%, 80%, 75%, 70%, 65%, 60%, 55%, or less of the circumference of the circle.

The connection mechanism of the device may couple to, stick to, adhere to, fuse to, glued to, attach to, combine with, connect to, fasten to, tethered to, insert into, poke through, entangle with, or be tied to the covering. The connection mechanism (e.g., an adhesive material) may be only for one-time use or capable or being used two or more times (e.g., 2, 3, 4, 5, or more times). The connection mechanism may have a surface area sufficient for connecting (e.g., coupling, binding) to only one covering. The connection mechanism may have a surface area sufficient for connecting to two or more coverings (e.g., 2, 3, 4, 5, or more coverings), and the covering(s) may be a same covering or different coverings. The connection between the device and the covering may be a temporary connection or a permanent connection. The connection between the device and the covering may utilize at least a portion of an area of the connection mechanism and at least a portion of an area of the covering opposite the subject's skin.

The device (e.g., a device comprising an adhesive material as a connection mechanism to connect to the covering) can preferably connect (e.g., couple, stick, attach, etc.) to any type of covering described herein relative to skin. In some cases, the device may not connect (e.g., couple, stick, attach, etc.) to the skin. In some cases, the device may not connect (e.g., couple, stick, attach, etc.) to the skin. A binding strength between the device and the covering (e.g., a bandage, patch, etc.) may be stronger than a binding strength between the covering and the subject's skin. A binding strength between the connection mechanism (e.g., adhesives) and the covering may be stronger than a binding strength between the covering and the subject's skin.

The device may come in contact with a portion of the skin adjacent to the covering during the process of removing the covering. In some cases, the device may not make a connection (binding, adhesion) with the skin adjacent to the covering, thereby allowing a selective removal (i.e. selective catching) of the covering from the skin. In some cases, the device may generate a connection with the skin adjacent to the covering. In such a case, the binding strength between the device and the covering may be stronger than a binding strength between the device and the skin, thereby to facilitate the selective removal of the covering from the skin. Strength of the connection between the device and the skin, if any, may be minimal to reduce or prevent injuring the skin during removal of the covering from the skin using the device. The selective removal of the covering by the device may not leave wounds, bruises, cuts, lacerations, scratches, grazes, abrasions, rashes, contusions, lesions, irritations, itchiness, pain, and/or other forms of trauma on the skin. The device may not leave any residues (e.g., residues from the adhesives of the device that makes the connection with the covering) on the skin.

The device can have one or more connection mechanisms (e.g., one or more adhesive materials). The device can have a plurality of connection mechanisms that are the same or different. In an example, the plurality of connection mechanisms may have the same or different connection strengths. The device may have at least 1, 2, 3, 4, 5, 6, 7, 8, 9, 10, or more connection mechanisms. The device may have at most 10, 9, 8, 7, 6, 5, 4, 3, 2, or 1 connection mechanism. The plurality of different connection mechanisms may be disposed along the length of the device and/or the width of the device. The plurality of connection mechanisms may or may not overlap with each other. The plurality of connection mechanisms may or may not be in contact (e.g., on one or more edges) with each other.

In some cases, the device can have a first adhesive material in a first portion of a surface of the device (e.g., a portion along a circumference of a circular or semi-circular device), a second adhesive material in a second portion of the surface of the device (e.g., a portion along a length of the circular or semi-circular device), and the first and second adhesive materials can be the same or different. In some cases, the second adhesive material may be a stronger adhesive than the first adhesive material. In some cases, while the first adhesive material of the device may not be sufficient to make a connection with the skin adjacent to the covering, the second adhesive material may be sufficient to make a connection with the skin adjacent to the covering. Such strong adhesive material of the second adhesive material may be useful in generating an initial, strong connection between the device and the covering (and not between the device and the skin) prior to, during, and/or subsequent to making other connections (e.g., via the first adhesive material) between the device and the covering. The second adhesive material of the device (e.g., at a central portion of the device) may adhere to and generate a connection with a leading portion (e.g., a leading point or edge) of the covering to initiate (i) connection between the device and the covering, (ii) further connection between the first adhesive material and other portions of the covering, and (iii) removal of the covering from the skin.

In an example, the device (e.g., a tube or a rod) configured to bind and remove the covering may have a cross-section that is substantially D-shaped. The round and non-flat portion of the D-shaped device may have a first adhesive material that selectively binds the covering and not the skin. The flat portion of the D-shaped device may have a second adhesive material that is a stronger adhesive than the first adhesive material. The second adhesive may be configured to generate a strong and/or permanent connection between the device and the covering. In some cases, the strong and/or permanent connection may initiate the removal of the covering by the device.

In some cases, a connection mechanism of a device may have a gradient of connection strengths, e.g., a gradient of adhesive strengths along a dimension (e.g., a length) of the connection mechanism.

The connection mechanism (e.g., a high tack adhesive) of the device may be covered by one or more removable sheets prior to using the device to remove a covering. Each removable sheet can be detached individually from the device by a user, thereby to allow exposing different areas of the connection mechanism. In some examples, the different areas of the connection mechanism may correspond to a dimension (e.g., a length of an edge) of the covering to be removed from the skin.

In some cases, one or more portions of each removable sheet can be detached from the device by the user. In such a case, each removable sheet may be configured to be divided (or split, tear, etc.) into a plurality of portions. Each removable sheet may be configured to be divided into at least 2, 3, 4, 5, 6, 7, 8, 9, 10 or more portions. Each removable sheet may be configured to be divided into at most 10, 9, 8, 7, 6, 5, 4, 3, or 2 portions. Thus, the connection mechanism may be user adjustable and/or customizable in its size (or area) and/or position by detaching one or more portions of the removable sheet that is covering the connection mechanism. The user adjustable and/or customizable connection mechanism may reduce or prevent exposure of the connection mechanism (e.g., the high tack adhesive) to the skin adjacent to the covering. Detaching the one or more of the portions of each removable sheet may be useful in exposing a predetermined/desired area of the connection mechanism to the covering.

In an example, different portions of the removable sheet of the device may be removed to substantially match different sizes/dimensions of the covering. The sizes/dimensions of the coverings (e.g., drug patches) may correspond to the respective doses of the drug in the coverings (e.g., 12, 25, 50, 75, or 100 microgram per hour (mcg/h) of fentanyl in a fentanyl patch). The multiple portions of each removable sheet may be coded with letters (e.g., alphabets, such as A, B, C, D, and/or E), numbers (e.g., 12, 25, 50, 75, and/or 100), icons, shapes, symbols, pictures, and/or colors, thereby corresponding to the respective sizes/dimensions and/or drug doses of the covering.

In some cases, each of the multiple portions of the removable sheet may have an extrusion (e.g., a tab) without any connection mechanism. Such extrusion may be used as a handle to hold (or grab, grasp, grip, etc.) each of the multiple portions of the removable sheet.

The device may be configured to allow the user to visualize a leading corner or edge of the covering during the initial contact between the device and the covering. Such visualization may allow a proper connection between the device (e.g., its high tack adhesive) and the covering, while reducing or preventing a connection between a portion of the device (e.g., its high tack adhesive) and the skin adjacent to the covering.

In some cases, the device can comprise or more indentations (e.g., one or more notches, slits, grooves, dents, or holes) that allows the user to visualize the leading corner or edge of the covering during the initial contact between the device and the covering. The device may comprise at least 1, 2, 3, 4, 5, 6, 7, 8, 9, 10 or more indentations for visualization of the leading corner/edge of the covering. The device may comprise at most 10, 9, 8, 7, 6, 5, 4, 3, 2, or 1 indentation for visualization of the leading corner/edge of the covering. The one or more indentations may be disposed at one or more corners of the device and/or edges of the device.

In some cases, at least a portion of the device comprising the connection mechanism (e.g., one or more adhesive materials) can be transparent or semi-transparent (e.g., opaque) to allow the user to visualize the leading corner/edge of the covering. At least 1%, 2%, 3%, 4%, 5%, 10%, 15%, 20%, 25%, 30%, 35%, 40%, 45%, 50%, or more of the portion of the device comprising the connection mechanism can be transparent or semi-transparent for visualization of the leading corner/edge of the covering. At most 50%, 45%, 40%, 35%, 30%, 25%, 20%, 15%, 10%, 5%, 4%, 3%, 2%, 1%, or less of the portion of the device comprising the connection mechanism can be transparent or semi-transparent for visualization of the leading corner/edge of the covering.

In some cases, the device may comprise one or more protrusions (e.g., one or more guards or bumps) adjacent to a corner or edge of the connection mechanism, which protrusion(s) may be aligned adjacent to a leading corner or edge of the covering to be removed. During or prior to generating an initial contact between the covering and the device, the protrusion(s) of the device may be aligned against a leading edge of the covering on the skin, to thereby ensure a proper alignment between the device and the covering. In some cases, position(s) of the one or more protrusions on the surface of the device may be fixed. In some cases, the position(s) of the one or more protrusions on the surface of the device may be movable, thereby to adapt to different sizes and/or shapes of the covering to be removed.

Once the covering (e.g., a bandage, patch, etc.) is removed from the skin and adhered to the device, the adhesion of the covering to the device may be reversible or irreversible. In some cases, the device may be used only once. In some cases, the device may be reusable. The device may be reusable to remove and retrieve at least 2, 3, 4, 5, 6, 7, 8, 9, 10, or more covering(s) simultaneously or at different times. The device may be reusable to remove and retrieve at most 10, 9, 8, 7, 6, 5, 4, 3, 2, or 1 covering(s) simultaneously or at different times. In an example, the device may be reusable to remove 5 fentanyl patches, either simultaneously or at different times, to thereby allow a simultaneous return and tracking of the 5 fentanyl patches that are initially provided in a single container prior to use.

In some cases, the device can comprise at least one component. In some examples, the device can be a single, individual device. In such a case, a portion of the individual device may comprise the connection mechanism configured to bind and retrieve a covering from the skin, and an additional portion of the individual device may be used as a handle for the user to hold the individual device during removal of the covering from the skin.

In some cases, the device can comprise at least two components. The at least two components can be movable relative to each other. The at least two components may be coupled to one another. Such coupling may be reversible. The at least two components can be separated from each other or at least partially connected to each other during removal of a covering from the skin. In some cases, the device can comprise two components: (1) a core, wherein at least a portion of an outer surface of the core comprises the connection mechanism to bind and remove the covering from the skin, and (2) a handle that is coupled to the core.

In some cases, the device can comprise two components: (1) a core, wherein at least a portion of an outer surface of the core comprises the connection mechanism to bind and remove the covering from the skin, and (2) a housing that covers at least a portion of the core. The housing can cover at least the connection mechanism of the core prior to or subsequent to removal of the covering by the core. The housing can cover the entirety of the core prior to or subsequent to removal of the covering by the core. Use of the core to remove the covering can require a partial or complete removal of the housing from the core. After the use of the core to remove the covering, the core which now comprises the covering can be retrieved back into the housing. Removal of the core from the housing to expose (or deploy) the connection mechanism of the core can require translation and/or rotation of the core relative to the housing. The translation and/or rotation may be a relative movement, and thus the translating and/or rotating piece can be the core, the housing, or both the core and the housing. Retrieval of the core back into the housing can require the same or different translation and/or rotation of the core relative to the housing.

In some cases, the core and/or the housing can comprise one or more handles for a user to hold the core and/or the housing during the removal of the core from the housing. Examples of the handle(s) can include a ring, hook, string, etc. The handle(s) may or may not be covered (or concealed) prior to use of the device to remove the covering. In some cases, the handle(s) may be movable relative to the core, such that the handle(s) can be hidden prior to and subsequent to the use of the core to remove the covering.

In some cases, the core can be partially removed from the housing to expose the connection mechanism (e.g., adhesive material on the surface of the core) for removal of the covering. During removal of the covering, the core may or may not be movable relative to the housing. In an example, the core may not be movable relative to the housing during the removal of the covering. In such a case, thus the core and the housing may need to be moved in the same fashion (e.g., rotated and translated relative to the covering on the skin) to remove the covering. In another example, the core may be movable (e.g., rotatable but not translatable) relative to the housing during the removal of the covering. In such a case, removing the covering may require (1) translating the housing relative to the covering (e.g., along the length of the covering) while (2) allowing the core to rotate relative to (and/or within) the housing to roll onto the covering, bind the covering, and remove the covering from the skin. Controlling the relative movement between the core and the housing can allow the user of the device to remove the covering without the user having to make contact with the connection mechanism (e.g., the adhesive material) of the core.

In some cases, the core can comprise one or more protrusions on its outer surface, and the housing can comprise one or more depressions on its inner surface. The depression(s) can correspond to the protrusion(s). Engagement of the protrusion(s) of the core and the depression(s) of the housing may be used to control movement (e.g., rotation) of the core relative to the housing. In some cases, an inner diameter of the housing may be sufficiently large such that the protrusion(s) of the core do not engage the depression(s) of the housing without exerting an external force (e.g., pressure) on the housing towards the core. In such a case, the core may be movable (e.g., rotatable) relative to the housing. On the other hand, upon application of the external force to engage the protrusion(s) of the core and the depression(s) of the housing, the core may not be movable relative to the housing. A portion of the housing comprising the depression(s) may be flexible (e.g., comprised of a flexible material), thereby allowing compression of the housing upon the application of the external force to engage the protrusion(s) and the depression(s).

The core may have, on its outer surface, at least 1, 2, 3, 4, 5, 6, 7, 8, 9, 10, or more protrusion(s). The core may have, on its outer surface, at most 10, 9, 8, 7, 6, 5, 4, 3, 2, or 1 protrusion(s). The housing may have, on its inner surface, at least 1, 2, 3, 4, 5, 6, 7, 8, 9, 10, or more depression(s). The housing may have, on its inner surface, at most 10, 9, 8, 7, 6, 5, 4, 3, 2, or 1 depression(s). In some examples, the protrusion(s) of the core may be part of a textured roll ring disposed on the outer surface of the core. In some examples, the depression(s) of the core may be part of a textured roll ring disposed on the inner surface of the housing. In some cases, the protrusion(s) of the core may be part of a gear with one or more teeth protruding outwards and away from the surface of the core. In some cases, the depression(s) of the housing may be part of a gear with one or more teeth protruding inwards and towards the surface of the core.

The housing and the core of the device may be used for a single covering removal. Alternatively, the housing and the core of the device may be reusable for multiple covering removals. In another alternative, either the housing or the core of the device may be reusable for multiple covering removals. Reusing one or more components of the device may help reduce an overall cost of removing and retrieving multiple coverings.

In some cases, the housing can be reusable for multiple covering removals. The housing and the core can be configured such that the housing can be refillable with a replacement core (i.e., a "core cartridge" or a "cartridge"). In such a case, once the housing and a first core cartridge are used in combination to remove a first covering (e.g., a first patch), the used first core cartridge can be removed from the housing and replaced with a new second core cartridge for removal of a second covering (e.g., a second patch). The housing can be reused at least 1, 2, 3, 4, 5, 6, 7, 8, 9, 10 or more time(s) by using at least 1, 2, 3, 4, 5, 6, 7, 8, 9, 10, or more core cartridge(s). The housing can be reused at most 10, 9, 8, 7, 6, 5, 4, 3, 2, or 1 time(s) by using at most 10, 9, 8, 7, 6, 5, 4, 3, 2, or 1 core cartridge(s). Each core cartridge may be configured to remove at least 1, 2, 3, 4, 5, or more covering(s). Each core cartridge may be configured to remove at most 5, 4, 3, 2, or 1 covering(s). In an example, each core cartridge may be configured to remove one individual covering.

In some cases, the housing may be configured to hold one individual core cartridge. In some cases, the housing may be configured to hold a plurality of core cartridges. In such a case, the housing may be configured to (i) use a first core cartridge (e.g., an outermost core cartridge) to remove and retrieve a covering from the skin, (ii) eject the used first core cartridge from the housing, and (iii) move a subsequent core cartridge that is contained within the housing in place of the ejected first core cartridge for removal of an additional covering. In such a case, the housing may be configured to hold at least 2, 3, 4, 5, or more core cartridges. The housing may be configured to hold at most 5, 4, 3, or 2 core cartridges.

The housing can include cartridge guides for guiding and holding the core cartridge inside the housing. The core cartridge can be releasably coupled to the housing via a quick release coupling mechanism. A quick release coupling mechanism can enable a user to rapidly mechanically couple (attach) and/or decouple (remove) the core cartridge to and from the housing with a short sequence of simple motions (e.g., rotating or twisting motions; sliding motions; depressing a button, switch, or plunger, etc.). For example, a quick release coupling mechanism can require no more than one, two, three, or four user motions to perform a coupling and/or decoupling action. In some cases, a quick release coupling mechanism can be coupled and/or decoupled manually by a user without the use of tools. In some cases, the quick release coupling mechanism can include a luer-type fitting that mechanically engages with the core cartridge when the core cartridge is inserted into the housing.

In some cases, the housing, the core cartridge(s), or both the housing and the core cartridge(s) can have an identifier (e.g., a machine readable code (MRC), an identification device, or a space for a user to sign or write name, date, notes, etc.) for identification and/or tracking purposes. One or more embodiments of such identifier are provided herein in the present disclosure. In some cases, the at least a portion of the housing may be transparent or semi-transparent to allow visualization of at least a portion of the core cartridge inside the housing. In some cases, the core cartridge along with its retrieved covering (e.g., a patch) may be collected at a hospital or a centralized location (e.g., a retail pharmacy, outpatient care hospital, nursing home, rehabilitation facility, long-term acute care hospital, etc.) for closed loop tracking of the used covering. In some cases, the core cartridge can comprise a neutralizer (e.g., chemical decontaminants, drug antagonists, mechanical encapsulant, etc.) that is activated upon or subsequent to retrieval of a covering by the core cartridge. The activated neutralizer may deactivate residual pharmaceuticals on the retrieved covering.

In some cases, the core cartridge may comprise a covering mechanism to cover and shield a retrieved covering. The core cartridge may comprise an outer layer and an inner layer that are movable relative to each other. Thus, the moving piece may be the outer layer, the inner layer, or both. The inner layer of the core cartridge may comprise the connection mechanism (e.g., an adhesive material) for removal of the covering from the skin. The outer layer of the core cartridge may be a shield that covers at least a portion of the inner layer of the core cartridge, e.g., a shield that covers at least the connection mechanism of the core cartridge. The outer layer of the core cartridge may be configured to cover and lock in the entire inner layer of the core cartridge, to thereby prevent access to the retrieved covering on the inner layer of the core cartridge. A coupling and release mechanism (e.g., the quick release coupling mechanism) may be part of the inner layer of the core cartridge, the outer layer of the core cartridge, or both.

In some cases, the device may be a film (e.g., a thin film) comprising a first side and a second side opposite the first side. A first portion of the first side of the film may comprise the connection mechanism (e.g., an adhesive material), and the second side of the film may not comprise the connection mechanism. The film may come in contact with the covering and moved (e.g., pulled away, translated, rolled) from the skin to remove the covering from the skin. The connection mechanism on the first side of the film may be covered by a different film prior to and/or subsequent to the use of the film to remove the covering from the skin.

A portion of a surface of the device may comprise the connection mechanism (e.g., an adhesive material) to bind the covering (e.g., a bandage, patch, etc., whether pre-medicated or not pre-medicated). The device may have an outwardly facing surface that comprises the connection mechanism. The device may have an additional component to cover (shield, hide) the connection mechanism on the outwardly facing surface prior to and/or removal of the patch or covering. The device may be a roller having an outwardly facing surface that comprises the connection mechanism. The device may be a roller having a plurality of outwardly facing sheets that are stacked (e.g., reversibly adhered), and each sheet may comprise the connection mechanism on the outwardly facing surface of the sheet to make a connection to the patch or covering. In such a case, once the roller is used to remove the patch or the covering, the outer most sheet with the removed patch or covering may be detached (e.g., peeled off) from the roller to expose a new sheet with a new outwardly facing surface comprising a new connection mechanism (e.g., the adhesive material). Each sheet may further comprise a portion (e.g., a corner tab) without the connection mechanism to facilitate easy removal of the used sheet.

In some embodiments, the device may be a wearable article (e.g., a glove, a finger cot). The wearable article may have an outwardly facing surface, and at least a portion of the outwardly facing surface of the wearable article may comprise the connection mechanism (e.g., an adhesive material) to bind the covering (e.g., a bandage, patch, etc., whether pre-medicated or not pre-medicated).

In some cases, the connection mechanism itself may be the device to remove the patch or covering from the bodily surface of the subject. In an example, an adhesive material may form an object that can be handled manually. The object may comprise a planar or curved surface that serves as the attachment zone. Such object may come in contact with the covering and moved (e.g., pulled away, translated, rolled) from the skin to remove the covering from the skin.

In such case of using the adhesive material as the connection mechanism, the adhesive material may adhere to the covering with less than, equal to, or greater than finger pressure. In some cases, the adhesive material may not require physical and/or chemical activation by an energy source to adhere to the covering. In some cases, the adhesive material may have sufficient ability to hold onto the adher-end (e.g., the covering). In some cases, the adhesive material may have enough cohesive strength to be able to cleanly remove the covering from the skin.

An area (e.g., a surface area) of the adhesive material of the device may be smaller, equal to, or greater than an area of the covering. In some cases, the area of the adhesive material may be larger than the area of the covering, such that the entire covering adheres to the adhesive material during or upon removal of the covering from the skin. In some cases, the area of the adhesive material may be at least about 1%, 5%, 10%, 20%, 30%, 40%, 50%, 60%, 70%, 80%, 90%, 100%, 200%, 300%, 400%, 500%, 1000%, or more than the area of the covering. In some cases, the area of the adhesive material may be at most about 1000%, 500%, 400%, 300%, 200%, 100%, 90%, 80%, 70%, 60%, 50%, 40%, 30%, 20%, 10%, 5%, 1%, or less than the area of the covering.

Suitable materials for the adhesive material can include hot melt-coated formulations, transfer-coated formulations, solvent-coated formulations, and latex formulations. The adhesive material can be a pressure-sensitive adhesive. Examples of the pressure-sensitive adhesive comprises natural rubber, styrene butadiene, butyl rubber, polyisobutylene, styrenic block copolymers, ethylene-vinyl acetate and related copolymers, poly-alpha olefins, acrylic adhesives, silicone, butadiene-acrylonitrile, polychloroprene, polybutadiene, atactic polypropylene, and modifications thereof.

Additional suitable materials for the adhesive material can comprise one or more of polyacrylates, polyvinyl ethers, rubbers (e.g., natural, butyl, etc.), butadiene-acrylonitrile polymer, elastomers (e.g., thermoplastic elastomers), copolymers, block copolymers (e.g., styrene-isoprene and styrene-isoprene-styrene block copolymers, styrene-diene type block copolymers such as SBS, SIBS, SEBS, and SEPS, styrene-ethylene-butylene, styrene-ethylene-propylene-styrene, ethylene-propylene-diene polymers, and styrene-butadiene polymer), poly-alpha-olefin, amorphous polyolefins, silicones, ethylene-containing copolymers (e.g., ethylene vinyl acetate, ethylacrylate, ethyl methacrylate), polyurethanes, polyamides, epoxies, polyvinylpyrrolidone and vinylpyrrolidone copolymers, polyesters, modifications thereof, and mixtures thereof. In some cases, the adhesive material can comprise additives, such as tackifiers, plasticizers, fillers, antioxidants, stabilizers, pigments, diffusing particles, curatives, fragrance, and solvents.

The adhesive material may not come off the device (e.g., a roller) as the cover is being removed, by the device comprising the adhesive material, from the subject's skin.

The adhesive material may be provided as a single layer on the device. The adhesive material may be provided as a multi-layer (e.g., 2, 3, 4, 5, or more layers) laminate. In some cases, an outer adhesive layer that has been used to remove a covering may be removed (e.g., peeled off) from the device to reveal an immediate inner adhesive layer that is to be used to remove another covering. The adhesive material may be provided as a single area or multi-areas (e.g., 2, 3, 4, 5, or more areas) on the device. In some cases, a first adhesive area may be used to remove a covering, and a second adhesive area may be used to remove another covering.

A single layer of the adhesive material may have a thickness ranging between about 0.01 millimeters (mm) to 5 mm. The thickness of the single layer of the adhesive material may be at least about 0.01 mm, 0.02 mm, 0.03 mm, 0.04 mm, 0.05 mm, 0.05 mm, 0.07 mm, 0.08 mm, 0.09 mm, 0.1 mm, 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, or more. The thickness of the single layer of the adhesive material may be at most about 5 mm, 4 mm, 3 mm, 2 mm, 1 mm, 0.9 mm, 0.8 mm, 0.7 mm, 0.6 mm, 0.5 mm, 0.4 mm, 0.3 mm, 0.2 mm, 0.1 mm, 0.09 mm, 0.08 mm, 0.07 mm, 0.06 mm, 0.05 mm, 0.04 mm, 0.03 mm, 0.02 mm, 0.01 mm, or less.

In some cases, the adhesive material may comprise one or more particles. Examples of one or more particles include polymers, metals, and ceramics. The particles may have various shapes and sizes. For example, a particle may be in the shape of a sphere, cuboid, or disc, or any partial shape or combination of shapes thereof.

The adhesive material, with or without any additional components (e.g., one or more particles), may be hypoallergenic. The adhesive material may not evoke any allergic response when in contact with a bodily surface (e.g., skin) of subject.

The adhesive material may be pressure sensitive. The pressure sensitive adhesive material may be temporarily or permanently tacky (sticky) at room temperature. The pressure sensitive adhesive material may be capable of adhering to surfaces (e.g., skin of the subject) by an application of nothing more than manual pressure (e.g., manual pressure by hand).

In some embodiments, the device may include one or more electric batteries to power one or more devices (e.g., actuators) included with the device.

FIG. 1A is a schematic view of the device 100 in an extended configuration, in accordance with an embodiment. The device 100 may generally comprise of two components: (i) a core 110 for removing a used patch from a subject (e.g., a patient) and supporting the used patch, and (ii) a housing 140 for encapsulating the core with or without the used patch. The core 110 may be movable (e.g., extendable and retractable) relative to the housing 140. The core 110 may move through the opening 141 of the housing 140. In addition, the core 110 can comprise a locking cap 130 with a locking mechanism to assist in securing and locking the core 110 (e.g., with the used patch loaded) inside the housing 140. In some cases, the locking cap 130 can have a display 132 to indicate whether the locking mechanism between the locking cap 130 and the housing 140 has been activated (e.g., locked or unlocked). FIG. 1B is a schematic view of the device 100 in a retracted configuration, in accordance with an embodiment. When retracted, the core 110 can be completely stored within the housing 140, and thus the locking cap 130 can be in contact with the opening 141 of the housing 140. Referring to FIG. 1A, the display 132 indicates that the locking cap 130 is in an unlocked state when the core 110 is extended out of the housing. Conversely, referring to FIG. 1B, the display 132 indicates that the locking cap 130 is in a locked state when the core (with a used patch loaded) is retracted and secured within the housing. In some embodiments, the device 100 can be locked to create a sealed container which is watertight to enable deployment of liquids within the sealed container. In some cases, the liquids may be chemical indicators, chemical or other neutralizers, tamper-evident dyes or other chemicals. The liquids may contain chemicals that react with residual controlled substances on the used patch.

The core shown in FIG. 1A or any of the embodiments disclosed herein can be a roller, scroll, bar or insert. The housing shown in FIGS. 1A and 1B or any of the embodiments disclosed herein can be a cover, shell, sleeve or canister. When the device is stored in the packaging, prior to use, at least a portion of the core may be positioned inside the housing. In an alternative embodiment, the core and the housing may be stored separately in the packaging, or stored in different packaging. As previously described, the core may be configured to be movable relative to the housing. The relative movement between the core and the housing may be a translational movement and/or a rotational movement. The housing may serve as a handle for a practitioner (e.g., a medical doctor, medical assistant, etc.) to hold the device while retrieving the used patch from the subject. During removal of the used patch, using the housing as a handle can prevent or substantially reduce the chance of the practitioner from contacting the active ingredient (pharmaceuticals) and/or adhesive of the used patch.

The core can be extendable from the housing and retractable into the housing. In some embodiments, not all of the core may be extended from the housing. In some embodiments, in some cases, about 50 percent (%) to about 90% of the length of the core may be extended from the housing. At least about 50%, 60%, 70%, 80%, 90% or more of the length of the core may be extend from the housing. At most about 90%, 80%, 70%, 60%, 50% or less of the length of the core may be extended from the housing. In an alternative embodiment, the core may be moved out of the housing completely without any overlap between the core and the housing. In such cases, the core may comprise a handle for the practitioner to hold while retrieving the used patch. The device may include a gap between the core and the housing. The gap may be larger than a thickness of the onboard patch that is rolled one or more times around the core (sufficient to roll the entire patch entirely onto the roller), so as to avoid physical contact between (i) the active matrix and/or adhesive of the used patch and (ii) the inner surface of the housing.

An outer cross-sectional dimension (e.g., diameter) of the core may be smaller than an inner cross-sectional dimension of the housing. In some embodiments, the outer cross-sectional dimension of the core may be about 20% to about 90% of the inner cross-sectional dimension of the housing. In some cases, the outer cross-sectional dimension of the core may be at least about 20%, 30%, 40%, 50%, 60%, 70%, 80%, 90% or more than the inner cross-sectional dimension of the housing. The outer cross-sectional dimension of the core may be at most about 90%, 80%, 70%, 60%, 50%, 40%, 30%, 20% or less than the inner cross-sectional dimension of the housing. The core and housing may have various shapes. The core and/or the housing may have a cross-section that is circular, triangular, square, rectangular, pentagonal, hexagonal, or any partial shape or combination of shapes thereof. The core and housing may have the same or different shapes.

FIGS. 2A-2E schematically illustrate a method for using the device 100 to retrieve a used patch 200 from a subject 300 (e.g., a patient). Referring to FIG. 2A, the device 100 is first brought in proximity to the subject 300. Referring to FIG. 2B, the core 110 can be extended out 402 from the housing 140 to remove the patch 200 from the subject's skin. In some cases, the surface of the core 110 can comprise one or more guides 112 (e.g., guard rails) to help align the patch around the core 110 during patch retrieval. The guide(s) 112 may help to wrap or align the patch 200 around the core 110. Thus, the guide(s) 112 may prevent slanting or misalignment of the patch 200 on the core 110 during the retrieval process. In an example, the core 110 can have two parallel guard rails around the circumference of the core 110, and the distance between the guard rails may be substantially equal to the height of the patch 200. Referring to FIG. 2C, the device 100 comprising the core 110 can couple (e.g., 'catch' or attach to) to the patch 200 on the subject 300, then rolled over 404 the patch 200 to remove the patch 200 from the subject's skin. The rolling can be manual (e.g., by the practitioner) or automatic (e.g., by an actuator). In some cases, the device 100 may have an actuator (e.g., an electric motor) that directs the core 110 to roll clockwise and/or counterclockwise to facilitate removal of the patch 200 from the subject 300. Referring to FIG. 2D, as the patch 200 is being rolled over the core 110, the adhesive 114 on the underside of the patch 200 can promote coupling of the underlying layer of the patch to a subsequently rolled over layer of the patch.

Referring to FIG. 2E, the patch 200 can be completely removed from the subject 300 and rolled around the core 110 of the device 100. An example of the patch that is retrieved and rolled up on the core 110 is shown as 204 in FIG. 2E. In some cases, removal of the patch 200 may reveal a visible mark on the skin of the subject 300, given that the patch had been applied to the subject's skin for a period of time.

Although the illustrated invention herein shows the device 100 comprising the core 110 and the housing 140, any configuration of devices can be used to (i) make a physical contact with the patch 200 and (ii) remove, contain, and/or retrieve the patch 200.

Figure 9:
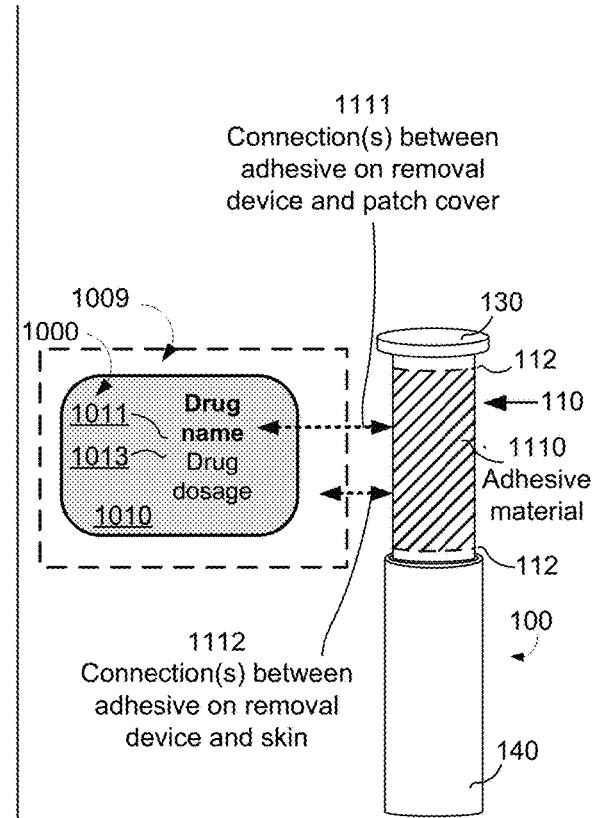
FIG. 9 is a schematic view of a pairing between a patch and a patch removal device that comprises an adhesive material on its patch removal area, in accordance with an embodiment.

In some cases, the patch 200 (as shown in FIG. 2, for example) and patch 1000 (as shown in FIG. 9, for example) may be used interchangeably herein in the present disclosure. In some cases, patch adhesive 202 and patch adhesive 1030 may be used interchangeably herein.

In any of the embodiments disclosed herein, the covering (e.g., the patch) can be provided in different sizes and/or shapes. In some examples, the different sizes and/or shapes of the patch can correspond to different doses of the drug. The patch may have a shape that is circular, triangular, square, rectangular, pentagonal, hexagonal, or any partial shape or combination of shapes thereof. In some cases, a surface area of a patch with a greater dose (i.e., strength) of the drug may be larger than a surface area of another patch with a lower dose. In an example, fentanyl patches of varied doses (e.g., microgram per hour (mcg/h)), sizes (e.g., centimeter squared ($cm^2$)) and drug content (e.g., milligrams (mg)) are provided in Table 1.

TABLE 1

| Dose (mcg/h) | Size ($cm^2$) | Fentanyl content (mg) |
|---|---|---|
| 12 | 5.25 | 2.1 |
| 25 | 10.5 | 4.2 |
| 50 | 21 | 8.4 |
| 75 | 31.5 | 12.6 |
| 100 | 42 | 16.8 |

After the used patch has been retrieved on the core of the device, the core can be slid into and locked with respect to the housing, to thereby encapsulate the used patch inside the housing and inhibit/prevent further tampering. The locking mechanism between the core and the housing may be irreversible. In an example, the device may comprise a ratchet mechanism to irreversibly lock the used patch/core inside the housing. In another example, the device may deploy an adhesive (e.g., cyanoacrylate) upon locking the core inside the housing. In some alternative embodiments, the locking mechanism may be reversible (locked and unlocked).

FIG. 3A is a schematic view of the device 100, showing the core 110 that is partially inserted into the housing 140, in accordance with an embodiment. The core 110 may comprise the used patch 200 rolled around the outer circumference of the core 110. In some cases, the circumference of the core may be greater than or substantially equal to the length/width of the patch, and the used patch may not overlap onto itself around the core. In some cases, the circumference of the core may be smaller than the length/width of the patch, and the used patch may overlap onto itself (e.g., roll one or more times around the core 110) as the patch is being retrieved. During retraction of the core 110 comprising the used patch 200, the exposed surface of the used patch 200, which may be the active matrix and/or adhesive of the used patch, may not make contact with the inner surface of the housing.

FIG. 3B is a schematic view of the device 100, showing a spacing mechanism between the core 110 and the housing 140, in accordance with an embodiment. The core 110 may comprise the used patch 200 rolled around the outer circumference of the core. In some cases, the housing 140 may comprise one or more protrusions (e.g., a rod) 151 on the interior surface 152 that faces a bottom surface 119 of the core 110. The bottom surface 119 of the core 110 may be an opposite end to the locking cap 130. The bottom surface 119 of the core 110 may comprise one or more depressions (e.g., a cavity) 120 that allow the protrusion(s) 151 to be inserted. When a portion of the core 110 is placed inside the housing 140, a portion of the protrusion(s) 151 may be configured to reside within the depression(s) 120. The protrusion(s) 151 and the depression(s) 120 may serve as a guide during the relative movement between the core 110 and the housing 140. In some embodiments, the insertion of the protrusion(s) 151 into the depression(s) 120 may substantially limit a horizontal movement (perpendicular to the length of the device) of the core 110 relative to the housing 140. Thus, the protrusions(s) 151 and the depression(s) 120 may serve as a spacing mechanism to maintain a set spacing between (i) the outer surface of the core 110 and/or the exposed surface of the used patch 200 and (ii) the inner surface of the housing 140. The spacing mechanism may also inhibit any accidental damage to the retrieved patch 200 that is captured on the core 110.

As shown in FIG. 3B or any of the embodiments disclosed herein, the surface of the protrusion(s) of the housing and/or the surface of the depression(s) of the core may include or be coated with a low friction material (e.g., a low friction polymer) to facilitate relative movement between the housing and the core. Examples of low friction polymers may include a fluorocarbon such as polytetrafluoroethylene (PTFE), high density polyethylene, other low friction polymers, or combinations thereof. In some cases, the low friction material may be a lubricant, such as a liquid lubricant (e.g., oil). In some embodiments, the low friction material may be used for other components of the device.

In some embodiments, the relative movement between the core and the housing may be a translational movement. In some cases, the surface of the protrusion(s) of the housing and/or the surface of the depression(s) of the core may be partially or entirely smooth, knurled, or serrated to adjust contact surface area and/or frictional force between the protrusion(s) of the housing and the depression(s) of the core. Additionally, a cross-sectional dimension (e.g., diameter) of the protrusion(s) of the housing may be smaller than a cross-sectional dimension of the depression(s) of the core. In some cases, the cross-sectional dimension of the protrusion(s) of the housing may be about 80% to about 98% of the cross-sectional dimension of the depression(s) of the core. The cross-sectional dimension of the protrusion(s) of the housing may be at least about 80%, 81%, 82%, 84%, 86%, 88%, 90%, 92%, 94%, 96%, 98%, or more of the cross-sectional dimension of the depression(s) of the core. The cross-sectional dimension of the protrusion(s) of the housing may be at most about 98%, 96%, 94%, 92%, 90%, 88%, 86%, 84%, 82%, 81%, 80%, or less of the cross-sectional dimension of the depression(s) of the core.

In some embodiments, the relative movement between the core and the housing may include both translational and rotational movements. In some cases, the protrusion(s) of the housing may include a screw comprising external threads, and the depression(s) of the core may include one or more bolts comprising internal threads that complement the external threads.

FIG. 3C is a schematic view of the device 100, showing another spacing mechanism between the core 110 and the housing 140, in accordance with an embodiment. In some cases, the core 110 may comprise one or more protrusions 121. The protrusion(s) 121 may be radial protrusions (e.g., ring(s) or rod(s)). The protrusion(s) 121 may have various shapes. The position(s) of the protrusion(s) 121 on the core 110 may be different than the position of the retrieved patch 200. In an example, the protrusion(s) 121 may be located beneath the locking cap 130, above the used patch 200. Alternatively or in addition to, the protrusion(s) 121 may be located at the bottom of the core 110, beneath the used patch 200. In some embodiments, the protrusion(s) 121 may substantially limit a horizontal movement (perpendicular to the length of the device) of the core 110 relative to the housing 140. Thus, the protrusion(s) 121 may serve as a spacing mechanism to maintain a set spacing between (i) the outer surface of the core 110 and/or the exposed surface of the used patch 200 and (ii) the inner surface of the housing 140. The spacing mechanism may also inhibit any accidental damage to the retrieved patch that is captured on the core.

As shown in FIG. 3C or any of the embodiments disclosed herein, an overall cross-sectional dimension (e.g., longest diameter or width) of the core including the protrusion(s) may be smaller than an inner cross-sectional dimension of the housing. In some cases, the overall cross-sectional dimension of the core including the protrusion(s) may be about 80% to about 98% of the inner cross-sectional dimension of the housing. The overall cross-sectional dimension of the core including the protrusion(s) may be at least about 80%, 81%, 82%, 84%, 86%, 88%, 90%, 92%, 94%, 96%, 98%, or more of the inner cross-sectional dimension of the housing. The overall cross-sectional dimension of the core including the protrusion(s) may be at most about 98%, 96%, 94%, 92%, 90%, 88%, 86%, 84%, 82%, 81%, 80%, or less of the inner cross-sectional dimension of the housing.

In some cases, the surface of the protrusion(s) of the core and/or the respective (or complementary) inner surface of the housing may be partially or entirely smooth, knurled, or serrated to adjust contact surface area and/or frictional force between the protrusion(s) of the core and the respective inner surface of the housing.

FIGS. 4A-4C illustrate various examples of the protrusion(s) 121 of the core 110, each showing a cross-sectional view of the core 110 along the cut plane 1 indicated in FIG. 3C. Referring to FIG. 4A, the protrusion(s) of the core 110 can include one or more rings 122. In such a case, the cross-sectional shape of the inner surface of the housing 140 may be circular in order to match and align with the ring(s) 122, as shown in FIG. 4D. Referring to FIGS. 4B and 4C, the protrusion(s) of the core 110 can include one or more (e.g., 1, 2, 3, 4, 5, or more) sectional protrusions (e.g., rods or pegs). As such, the inner surface of the housing 140 may comprise one or more (e.g., 1, 2, 3, 4, 5 or more) sectional depressions. In some cases, the sectional protrusion(s) of the core may assist in proper alignment of the core relative to the housing during the retraction of core into the housing. In some cases, once the device is locked, the sectional protrusion(s) of the core may inhibit rotational and/or horizontal movement of the core (with the retrieved patch) relative to the housing. In some cases, the core may comprise two or more sectional protrusions, and the spacing between the sectional protrusions around the circumference of the core may be substantially the same. Alternatively, the spacings between the sectional protrusions around the circumference of the core may be different. In an example, as shown in FIG. 4B, the core 110 can comprise two rods 123a and 123b. As such, the housing 140 of the device may comprise two depressions 153a and 153b that match the shape of the rods 123a and 123b, respectively, as shown in FIG. 4E. In another example, as shown in FIG. 4C, the core 110 can comprise three rods 124a, 124b and 124c. As such, the housing 140 of the device may comprise three depressions 154a, 154b and 154c that match the shape of the rods 154a, 154b and 154c, respectively, as shown in FIG. 4F.

In any of the embodiments disclosed herein, the device may comprise the spacing mechanism between the core and the housing as described in (i) FIG. 3B or variations thereof, (ii) FIG. 3C and FIGS. 4A-4F, or variations thereof, or (iii) both.

FIGS. 5A-5C illustrate various embodiments of the device 100. Referring to FIG. 5A, the core 110 is extended out from the housing 140 to remove and secure a used patch. The core 100 can comprise one or more attachment zones 114 that can couple to a leading edge of the patch and initiate patch retrieval. The location on the core 110 where the patch would be initially attached to is indicated in 208. In some cases, the attachment zone(s) 114 may be a designated location within the core 110 as a standardized starting point for all patches of different sizes and/or drug doses. The binding strength between the attachment zone(s) 114 and the outer surface of the patch may be greater than the binding strength between the underside ("active") side of the patch and the subject. In some embodiments, the attachment zone(s) 114 can have an adhesive 116 as a coupling mechanism to make contact and bind the outer surface of the patch. Alternatively, the attachment zone(s) 114 may have one or more pinch or grab mechanisms (e.g., hooks) for latching onto the leading edge of the patch. In some cases, the attachment zone(s) 114 may have a locking mechanism (e.g., a cover). Upon attachment of the leading edge of the patch to the attachment zone(s) 114, the locking mechanism of the attachment zone(s) 114 may be triggered by the practitioner to lock the leading edge of the patch onto the core 110 and facilitate rolling of the entire patch onto the core 110. In some cases, the core 100 may comprise additional attachment zone(s) to couple to other portions of the patch during removal of the patch. The housing 140 may comprise one or more windows 142 for visual identification of the patch that is retrieved and stored within the device 100. Thus, prior to retrieving the patch and retracting the core 110 into the housing 140, the window(s) 142 may not display any information regarding the patch.

Referring to FIG. 5B, once the retrieved patch 204 is rolled-up on the core 110, the core 110 can be retracted 404 back into the housing 140. Such retraction mechanism of the device 100 may be manual (e.g., by the practitioner) or automatic (e.g., by an actuator). In some cases, the device 100 may include an actuator (e.g., an electric motor) that enables relative movement (e.g. linear translation) between the core 110 and the housing 140. The locking cap 130 of the core 110 and the housing 140 can include one or more complementary locking mechanisms 134. The locking mechanism(s) 134 may completely encapsulate and secure/lock the retrieved patch 204 inside the housing 140. The locking mechanism(s) 134 may be irreversible. In some cases, the locking mechanism(s) 134 may comprise snap fits that irreversibly lock in one direction when the user twists or rotates the locking cap in that direction. In some cases, the locking mechanism(s) 134 may be a permanent adhesive (e.g., a super glue) that is deployed only upon retracting the core 110 with the retrieved patch 204 back into the housing 140, to thereby make a permanent adhesion between the core 110 and the housing 140. In some cases, the locking mechanism(s) 134 may be time sensitive. For example, the locking mechanism(s) 134 may be configured to automatically lock within a predetermined time (e.g. 10 seconds, 15 seconds, or 20 seconds, or any time duration therebetween) after the core and used patch have been retracted into the housing.

Referring to FIG. 5C, once the retrieved patch is completely contained within the housing 140, the display 132 can indicate that the locking mechanism between the locking cap 130 and the housing 140 has been successfully activated. As described above, the housing 140 can comprise window(s) for visual identification of the retrieved patch. In some embodiments, one of the window(s) can be a viewing window 142a for one or more landing zones 144. The landing zone(s) 144 may indicate whether a patch with a correct dimension (indicating a correct controlled substance dose) has been retrieved inside the device 100. The landing zone(s) 144 may show written descriptions of the expected patch size and/or dose. In some cases, the landing zone(s) 144 may be one or more lines drawn next to each dose of the controlled substances (e.g., fentanyl in 12 mcg/h, 25 mcg/h, 50 mcg/h, 75 mcg/h and 100 mcg/h). The line(s) of the landing zone(s) 144 may be indicative of the expected target position of the end of the patch that is opposite to its leading edge. In an example, a 75 mcg/hr fentanyl patch is shorter than a 100 mcg/hr fentanyl patch. If the leading edges of the two patches are coupled to the same initial attachment zone of the core 110 (e.g., the attachment zone(s) 114 in FIGS. 5A-5B), then the 75 mcg/hr fentanyl patch end may align with its respective landing zone that is different than the respective landing zone of the 100 mcg/hr fentanyl patch. Upon locking the device 100, a landing marker 145 may appear adjacent to one of the landing zone(s) 144 to visually confirm that the patch with the correct size and/or dose has been retrieved. In some cases, the window 142a may be transparent or semitransparent, and the landing marker 145 may be a portion of the end of the retrieved patch shown through the window 142a, to thereby visualize a correct alignment of the end of the retrieved patch to its corresponding landing zone. In an example, the circumference of the core may be greater than or substantially equal to the length/width of the patch. In such a case, as shown in FIG. 5D, a portion of the end of the retrieved patch 145a may (i) not overlap onto another portion of the retrieved patch and (ii) align to its corresponding landing zone (e.g., 75 mcg/h). In another example, the circumference of the core may be smaller than the length/width of the patch. In such a case, as shown in FIG. 5E, a portion of the end of the retrieved patch 145b may (i) overlap onto another portion of the retrieved patch and (ii) align to its corresponding landing zone (e.g., 75 mcg/h). In some cases, the window 142a may not be transparent or semitransparent, and the landing marker 145 may be a display, comprising ink or electronic ink (E-ink), that is automatically activated upon locking the device 100.

In some embodiments, the viewing window 142a of the device 100 may always display the landing zone(s) 144, regardless of whether the used patch is retrieved. In such cases, the landing marker 145 may only appear adjacent to the appropriate landing zone once the retrieved patch is completely contained within the housing 140 and the device 100 is locked.

Referring to FIG. 5C, one of the window(s) of the housing 140 can include a selective information display 142b. Subsequent to locking the device 100, a machine readable code (MRC) (e.g., a barcode or unique patch identifier (UPI)) 148 and one or more practitioner identification blocks 150 can appear on the display 142b. The MRC 148 may be for the practitioner to scan and electronically record the retrieval of the used patch in the device 100 in a database. In some cases, the date, time and/or location of scanning the MRC 148 may be automatically updated to the database. In some cases, the practitioner may need to log in (e.g., with the practitioner's user identification (ID) and password) to the computer that is operatively coupled to the scanner that scans the MRC 148. Thus, the electronic information about the practitioner may be automatically updated to the database when scanning the MRC 148 of the device 100. This may aid tracking of the retrieved patch within the device 100, as well as the practitioner who is responsible for retrieving the patch. Scanning the MRC 148 may close the digital loop on the physical removal of the patch, thereby electronically linking the patient, the specific patch, and the practitioner with a date, time and/or location of the patch retrieval. As shown in FIG. 5C, the practitioner identification block(s) 150 may be an additional mechanism to keep the practitioner accountable. The practitioner identification block(s) 150 may be one or more writable areas. The practitioner may be required to personally and manually document various information regarding the patch retrieval on the practitioner identification block(s) 150, such as the practitioner's name, patch retrieval time (e.g., start and/or end time) and date, patch dose, a location on the subject where the patch was applied to, etc. In some cases, the information documented on the practitioner identification block(s) 150 has to correlate with electronic entry of the same event (e.g., from scanning the MRC 148) as an additional anti-deterrent measure during the patch retrieval process. The practitioner may be required to use a writing instrument with a permanent ink (e.g., a sharpie) to prevent deletion or tampering of the documented information on the practitioner identification block(s) 150.

In some embodiments, the display 142b can comprise a mechanical and/or polarization lens that only exposes the MRC 148 and the practitioner identification block(s) 150 upon the relative movement between the core 110 and the housing 140 when/upon locking the device 100. In an example, an out of phase polarized lens can be used. In a manner similar to polarized eyeglass lenses or polarization filters on camera lenses, the display 142b can include out of phase polarized lines, which, upon deployment and locking of the device 100, change phase and switch from out of phase (e.g., opaque) to in phase (e.g., transparent). As such, the MRC 148 and the practitioner identification block(s) 150 can appear on the display 142b upon locking the device 100.

In some embodiments, the housing 140 of the device 100 can comprise two layers. Both internal and external layers of the housing 140 can have windows that would overlap each other only when the housing 140 and the core 110 are locked in place. The internal layer of the housing 140 may be hidden from view until and after the patch is retrieved and the device 100 is locked. Each pixel of the internal window may be a linearly polarized film, and the pixels that make up the MRC 148 and the practitioner identification block(s) 150 may be rotated by 90 degrees with respect to the background pixels (e.g., background pixels are horizontally polarized, and the pixels for the MRC 148 and the practitioner identification block(s) 150 are vertically polarized). Each pixel of the external window may be linearly polarized and parallel to the polarization direction of the background pixels of the internal window. As such, once the internal and external windows are overlaid upon locking the device 100, the MRC 148 and the practitioner identification block(s) 150 of the internal window may be cross-polarized with respect to the pixels of the external window and become visible to the naked eye.

In some embodiments, the housing 140 of the device 100 can comprise two layers. The external layer of the housing 140 may comprise the display 142b that (i) is transparent or semitransparent and (ii) permanently displays the MRC 148 and the practitioner identification block(s) 150 (e.g., in permanent ink). The internal layer of the housing 140 may have two panels. The first panel of the internal layer may be configured to overlap with the display 142b of the external layer when the device 100 is not locked. The second panel of the internal layer may be configured to overlap with the display 142b of the external layer when the device 100 is locked by the locking mechanism(s) 134. The color of the first panel of the internal layer may be identical to the color of the MRC 148 and the practitioner identification block(s) 150. As such, when the display 142b overlays the first panel, the MRC 148 and the practitioner identification block(s) 150 may not be visible to the naked eye and/or the scanner that scans the MRC 148. On the other hand, the color of the second panel of the internal layer may be different than the color of the MRC 148 and the practitioner identification block(s) 150. As such, when the display 142b overlays the second panel, the MRC 148 and the practitioner identification block(s) 150 may be visible to the naked eye and/or the scanner that scans the MRC 148.

In some embodiments, the display 142b can comprise other mechanisms to present the MRC 148 and the practitioner identification block(s) 150. In some cases, the locking mechanism of the device 100 may trigger release of chemicals (e.g., ink) to display the MRC 148 and the practitioner identification block(s) 150. In some cases, the locking mechanism of the device 100 may trigger rotation of electronic ink (E-ink) capsules (e.g., E-ink microcapsules) within the display 142b in a specific configuration to present the MRC 148 and the practitioner identification block(s) 150.

In some embodiments, the practitioner identification blocks may be present on the display 142b at all times, whether the device is locked or not, and only the MRC 148 may be triggered to appear on the display 142b upon and after locking the device.

Referring to FIG. 5C, the housing 140 can further comprise a chemical indicator window 146. The chemical indicator window 146 may confirm retrieval of a correct patch as an additional accountability and/or security mechanism. Upon locking the device 100, a chemical indicator inside the housing 140 may undergo a chemical reaction with residual pharmaceuticals on the retrieved patch, resulting in an appearance of a visual marker displayed on the chemical indicator window 146. In an example, the chemical indicator may comprise a detector molecule (e.g., a small molecule or an antibody) configured to bind to the target pharmaceutical (e.g., fentanyl). In some cases, the chemical indicator may be presented on one or more protrusion(s) on the inner surface of the housing 140, and the protrusion(s) may come in contact with the "active" side of the retrieved patch to promote a reaction between the detector molecule and the target pharmaceutical. Alternatively or additionally, locking of the device 100 may deploy one or more liquids that can dissolve the target pharmaceutical on the retrieved patch, and the liquid(s) may come in contact (e.g., by gently shaking the device 100) with the chemical indicator to promote reaction between the detector molecule and the target pharmaceutical. Alternatively or additionally, the chemical indicator may detect trace amounts of the target pharmaceutical in air inside the device 100. In some embodiments, the chemical indicator may comprise an additional molecule (e.g., an additional antibody) for detection and visualization of the complex between the detector molecule and the target pharmaceutical. In some embodiments, detection of the target pharmaceutical by the chemical indicator can induce a change in color (e.g., from transparent to a visible color) of the chemical indicator window 146. In some embodiments, detection of the target pharmaceutical by the chemical indicator can display a message (e.g., from blank to "fentanyl") using ink or electronic ink (E-ink) on the chemical indicator window 146. In some embodiments, the chemical indicator can only be initiated upon the locking of the device 100 to prevent "pre-treatment" of the indicator and subsequent patch diversion.

FIG. 6 is a flowchart illustrating a method of administering a controlled substance transdermal patch to a subject (e.g., a patient), in accordance with an embodiment. Referring to 610, a practitioner (e.g., a physician) can order a controlled substance transdermal patch (referred elsewhere as a "patch") (e.g., a fentanyl patch) into the patient's electronic medication administration record system (eMAR). The practitioner may select an appropriate dose and/or duration time of applying the patch for the patient. Referring to 620, the same practitioner (e.g., the physician) or a different practitioner (e.g., a nurse) can open the eMAR of the patient to see the order of the patch, and acquire the appropriate patch from an automated dispensing machine (ADM). Referring to 630, the practitioner can scan (i) a machine readable code (MRC) of the patient (e.g., from a wristband of the patient), (ii) a MRC of the practitioner obtaining the patch from the ADM (e.g., from the practitioner's badge), and (iii) a MRC of the patch to record the information in the database (e.g., electronic database). The MRC of the patch may be on the non-active side of the patch or on the packaging of the patch. Referring to 640, the patient's eMAR can instruct the practitioner of an anticipated patch removal time for a given patch application time. In some cases, the patient's eMAR may provide a 2-hour window of time around the anticipated patch removal time. Referring to 650, the practitioner can apply the patch to the patient. In some cases, after the application of the patch to the patient, the practitioner may need to electronically record the time of the actual application of the patch and the location on the subject's body where the patch was applied to.

Figure 7:
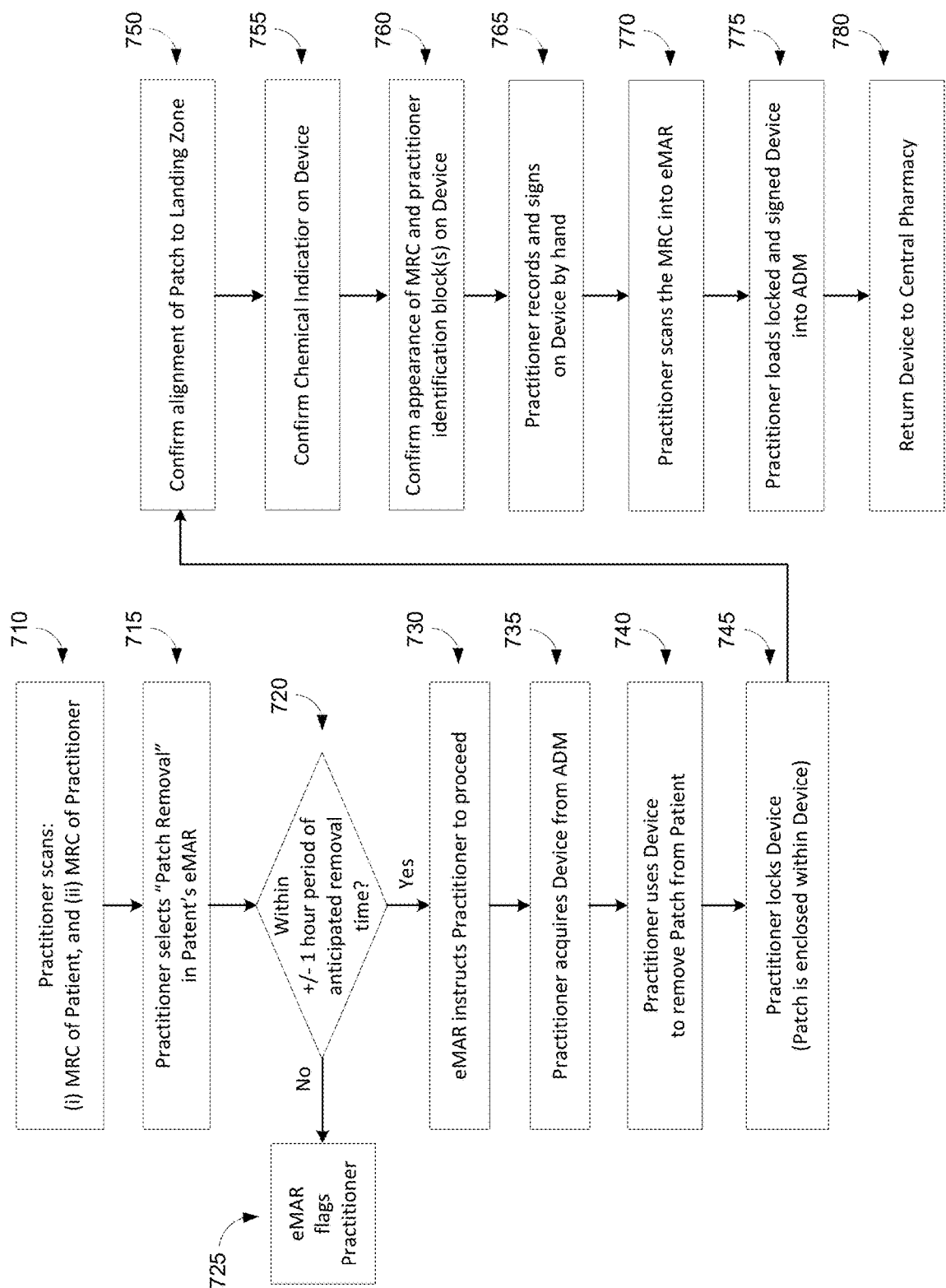
FIG. 7 is a flow chart illustrating a method of using a patch removal/tracking device to remove and track a controlled substance transdermal patch from a subject, in accordance with an embodiment.

FIG. 7 is a flow chart illustrating a method of using a patch removal/tracking device (referred elsewhere as a "device") to remove and track a controlled substance transdermal patch (referred elsewhere as a "patch") from a subject (e.g., a patient), in accordance with an embodiment. Referring to 710, the practitioner (e.g., a nurse) can scan (i) the MRC of the patient (e.g., from a wristband on the patient) and (ii) the MRC of the practitioner. Referring to 715, the practitioner can select "Patch removal" in the patient's eMAR. Referring to 720, the patient's eMAR determines whether 715 is performed within the 2-hour window (e.g., plus/minus 1 hour) of the anticipated patch removal time. Referring to 725, if the time at which 715 is performed is outside of the 2-hour window, then the patient's eMAR can flag the practitioner in the system and report it to the practitioner's supervisor. In some cases, the practitioner who is flagged by the eMAR may be prohibited from obtaining new patches from the ADM and/or removing used patches from the patients until the issue is resolved. Such hindrance to perform a daily task may serve as an accountability and security mechanism. Referring to 730, if the time at which 715 is performed is within the 2-hour window, then the patient's eMAR can instruct the practitioner to acquire the device from the ADM to remove the patch from the patient. Referring to 735 and 740, the practitioner can obtain the device from the ADM and uses the device to remove the patch from the patient. Referring to 745, the practitioner can retrieve the used patch inside the device and lock the device. The locking mechanism of the device may be irreversible to prevent tampering of the retrieved patch. Referring to 750, upon locking the device, the practitioner can visually confirm alignment of the patch to an appropriate landing zone. The one or more landing zones may be shown through a window on the housing of the device. Alternatively, the practitioner can confirm the appearance of a landing marker on the appropriate landing zone that corresponds to the retrieved patch. In some cases, the practitioner may record the result in the patient's eMAR. Referring to 755, the practitioner can visually scan the chemical indicator window on the housing of the device. The chemical indicator window may exhibit a change in color or an appearance of a marking to indicate that the correct controlled substance (e.g., fentanyl) has been detected inside the device. In some cases, the practitioner may record the result in the patient's eMAR. Referring to 760, the practitioner can visually scan the appearance of (i) the MRC (e.g., a unique patch identifier (UPI)) that is specific to the device and (ii) the practitioner identification block(s) on the housing of the device. Referring to 765, the practitioner can be required to personally and manually document various information regarding the patch retrieval on the practitioner identification block(s), such as the practitioner's name, patch retrieval time (e.g., start and/or end time) and date, patch dose, a location on the subject where the patch was applied to, etc. Referring to 770, the practitioner can be required to scan the newly appeared MRC (e.g., the UPI) into the patient's eMAR. Referring to 775, the practitioner can load the locked, signed, and scanned device into the ADM. Referring to 780, one or more devise collected in the ADM can be returned to a central pharmacy for a complete disposal and/or destruction of the remaining controlled substances in the used transdermal patches.

In some embodiments, subsequent to application of a transdermal patch to a subject (e.g., a patient), both (i) a predetermined medication time for which the transdermal patch is to be applied to the subject and (ii) a duration of time for which the transdermal patch is being applied to the subject may be obtained (e.g., via scanning one or more identifiers of the transdermal patch and/or the subject). In some cases, if the duration of time meets a predetermined threshold, a message may be displayed on an electronic device, wherein the message comprises an instruction to remove the transdermal patch from the subject. In some cases, the predetermined threshold may be determined by a practitioner prescribing the transdermal patch to the subject. In some cases, the predetermined threshold may be determined by a manufacturer of the transdermal patch or a government agency (e.g., FDA). In some cases, the predetermined threshold may be within (e.g., longer than or less than) at most 5 hours, 4.5 hours, 4 hours, 3.5 hours, 3 hours, 2.5 hours, 2 hours, 1.5 hours, 1 hour, 50 minutes, 40 minutes, 30 minutes, 20 minutes, 10 minutes, 5 minutes, 1 minute, or less from the predetermined medication time. In some cases, the predetermined threshold may be within at least 1 minute, 5 minutes, 10 minutes, 20 minutes, 30 minutes, 40 minutes, 50 minutes, 1 hour, 1.5 hours, 2 hours, 2.5 hours, 3 hours, 3.5 hours, 4 hours, 4.5 hours, 5 hours, or more from the predetermined medication time. In some cases, a computer processor may automatically send an alert message (e.g., to a healthcare professional's network and/or a centralized location that monitors usage and/or distribution of the transdermal patch) when the duration of time is above or below a predetermined threshold.

In some embodiments, the patch removal/tracking device disclosed herein may be modified to be used as a patch supply/application unit for tracking of prescription and application of controlled substances and other pharmaceuticals.

In some embodiments, the device may have one or more security features to ensure closed loop tracking of the patch retrieval. In some cases, the device may comprise one or more external windows that selectively display information upon securing of the patch within the device. The one or more external window(s) may or may not be a magnifier. In some cases, such information may ensure that a correct patch has been retrieved within an expected time period. In some examples, the information selectively displayed on the device comprises one or more of the following: (a) one or more landing zones that are configured to indicate a dimension of the patch; (b) a MRC corresponding to the device; (c) one or more writable areas for a practitioner (who is removing the patch) to record (i) the practitioner's name, (ii) time, date, and/or location of securing of the patch, (iii) patch dose, and/or (iv) a location of the patch on the subject; and (d) a chemical indicator that is configured indicate a presence of the controlled substance in the patch.

In some embodiments, the device can include a neutralizer (e.g., chemical decontaminants, drug antagonists, mechanical encapsulant, etc.) to deactivate residual pharmaceuticals on the retrieved patch. The neutralizer may help prevent diversion of the prescription medication loaded in the patch inside the device. Once the device is locked, the neutralizer may be applied to the patch by way of a solid, liquid, gel, vapor or gas medium. In some cases, the neutralizer may be a chemical decontaminant for the controlled substance (e.g., fentanyl and its derivatives such as carfentanil). For example, the neutralizer for fentanyl and its derivatives may be a mixture of peracetyl borate, its functional variant thereof, and a solvent (e.g., water). In some cases, the neutralizer may be a molecular antagonist to the controlled substance (e.g., naloxone as an antagonist of opioids including fentanyl). In some cases, the neutralizer may be a mechanical encapsulant. The mechanical encapsulant may solidify upon locking of the device or another trigger (e.g., manually by the practitioner) to encapsulate the retrieved patch within the device and prevent any access to the retrieved patch on the core.

In some cases, the neutralizer may be automatically activated once the patch is removed and retrieved into the device. In an example, the device may have a cap with a locking mechanism. Once the patch is retrieved by the device and the cap is locked (to lock the device), the neutralizer may be automatically activated. In some cases, the neutralizer may be manually activated. In an example, subsequent to retrieving the patch in the device, the practitioner may use a sensor or a button disposed on the outer surface of the device to activate the neutralizer.

In some cases, the neutralizer may be coated on a surface of a sleeve (or sheath), and the sleeve may be disposed over the covering that is retrieved onto the core of the device, thereby neutralizing (e.g., encapsulating or deactivating) any residual drug on the retrieved patch. The sleeve may be rolled (e.g., rolled to a shape of a scroll, rolled to a shape of a packaged condom, folded one or more times onto itself, etc.) prior to neutralizing, then unrolled during use. In some cases, the sleeve may be a lubricated sleeve to glide over a target surface (e.g., a retrieved patch). The neutralizer may be solid (e.g., particles), liquid (e.g., aqueous, organic, or a combination thereof), gel, vapor or gas medium, or a combination thereof. The material of construction for such sleeve may be, for example, a natural or synthetic elastomeric material, such as a natural rubber (e.g., latex), a synthetic silicone rubber, or a polymer (e.g., polyvinylchloride, polyurethane, polyester, polyolefin, etc. At least a portion of the sleeve may be transparent, semi-transparent, or opaque. In some cases, the neutralization sleeve may comprise an identifier (e.g., a signature line for a practitioner to sign). Thus, the material of the neutralization sleeve may have a sufficient strength, such that it may not be punctured upon signature by a pen or pencil.

In some cases, the device containing the retrieved patch may be collected at a centralized location (e.g., a central pharmacy) prior to activating the neutralizer. The centralized location may be responsible for collection and destruction of the patch (e.g., by activating the neutralizer). In some cases, the device may be designed such that the neutralizer of the device may not be activated until a person at the centralized location confirms that the abovementioned security features of the device have been engaged. In some examples, the device may have a lock, and the person at the centralized location may have a corresponding key that is needed to engage with the lock to activate the neutralizer. Other male-to-female joining mechanisms (e.g., a socket and a wrench) may also be used. In such a case, no nurse or other practitioners that are responsible for removing the patch from the patient may be able to pretend to neutralize the patch when the device actually does not have any patch inside. This "last mile" methodology may help reduce or prevent diversion of the patch by the nurse of other practitioners.

In some cases, a patient may have a practitioner of a hospital to apply the patch, be admitted to the hospital during an active period of the patch (e.g., a prescribed duration), and have the patch removed by the same or different practitioner of the hospital using the device.

In some cases, the patient may have the practitioner of the hospital to apply the patch, not be admitted to the hospital during the active period of the patch, and use the device to personally (or with the help of a third party) remove the patch. Such patient may be an outpatient patient. The outpatient patient (or the outpatient's representative) may need to return the patch-containing device or at least a portion of the device that contains the removed patch to the hospital or the centralized location (e.g., the retail pharmacy, outpatient care hospital, nursing home, rehabilitation facility, long-term acute care hospital, etc.) to obtain a refill of the patch prescription. In such case, the hospital will forward the patch-containing device to the centralized location, if necessary, and the centralized location may activate the neutralizer of the device. Once the abovementioned security features of the device have been evaluated and the device neutralized by the central pharmacy, the patient may be able to obtain the refill of the patch prescription.

In some cases, the patient may receive a packaged patch from the hospital or a retail pharmacy (may or may not be the centralized location) and self-apply the patch. However, the patient may need to go to the hospital, the retail pharmacy, or the centralized location to have the patch removed via the device by a professional (e.g., the practitioner). Subsequently, the patient may be able to obtain the refill of the patch prescription.

In some embodiments, the mechanism of the device to activate the neutralizer may include a combination activation mechanism. In some cases, the combination activation mechanism can be a combination lock, which may be unlocked by rotating one or more dials (e.g., a single dial or a set of two or more dials). The dial(s) may be rotated to (i) one or more number(s), letter(s) (e.g., alphabetical letter(s)), and/or symbols, or (ii) through a specific sequence of number(s), letter(s), and/or symbol(s). In some cases, the mechanism of the device to activate the neutralizer may include both the combination activation mechanism and a second mechanism (e.g., a button, sensor, knob, etc.). In an example, a user may need to rotate the dial(s) to unlock the combination activation mechanism, and further activate the second mechanism (e.g., by pressing the button, activating the sensor, or turning the knob) to activate the neutralizer.

Figure 8A:
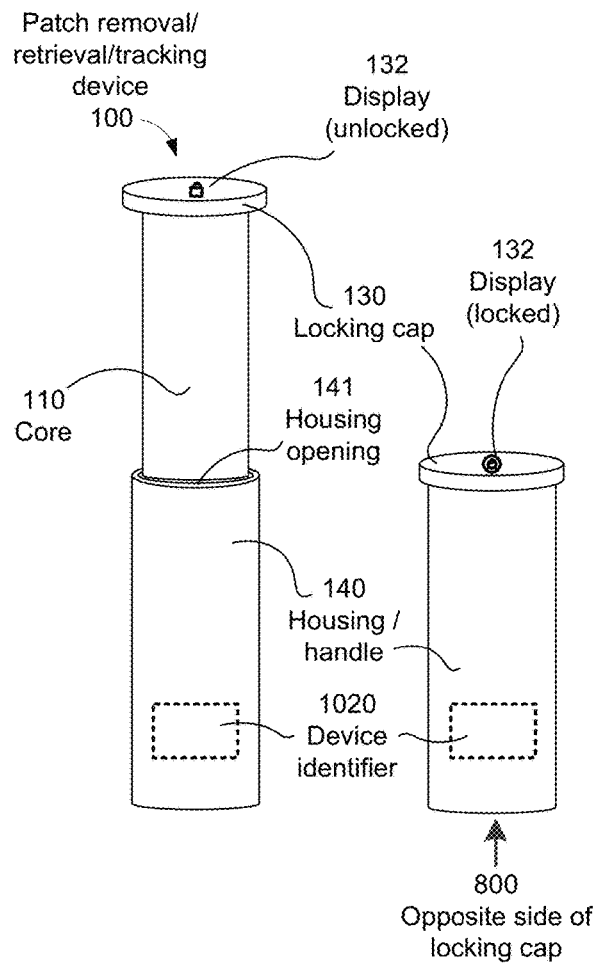
FIG. 8A shows schematic views of a patch removal device in an extended configuration and in a retracted configuration, in accordance with an embodiment.

FIG. 8A shows schematic views of the device 100 in an extended configuration (left) and in a retracted configuration (right), in accordance with an embodiment. As abovementioned, the device 100 comprises the core 110 and the housing 140. The core 110 may be movable (e.g., extendable and retractable) relative to the housing 140. The core 110 may move through the opening 141 of the housing 140. In addition, the core 110 can comprise a locking cap 130 with a locking mechanism to assist in securing and locking the core 110 (e.g., with the used patch loaded) inside the housing 140. In some cases, the locking cap 130 can have a display 132 to indicate whether the locking mechanism between the locking cap 130 and the housing 140 has been activated (e.g., locked or unlocked). When retracted, the core 110 can be completely stored within the housing 140, and thus the locking cap 130 can be in contact with the opening 141 of the housing 140. In some embodiments, the device 100 can be locked to create a sealed container which is watertight to enable deployment of liquids within the sealed container. In some cases, the liquids may be chemical indicators, a drug neutralizer, tamper-evident dyes or other chemicals. The liquids may contain chemicals that react with residual controlled substances on the used patch.

Figures 8B, 8C:
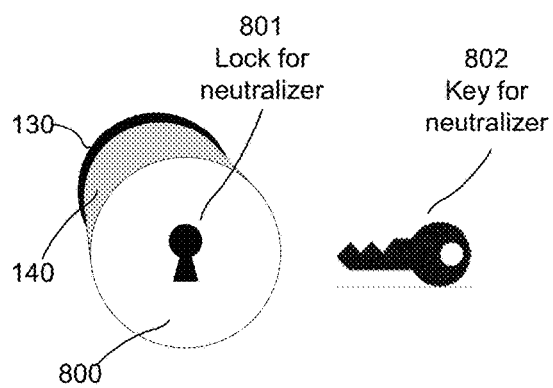
FIG. 8B shows a schematic view of a bottom side of a patch removal device that includes a lock to activate a drug neutralizer.
FIG. 8C shows a schematic view of a key for the lock of the patch removal device, in accordance with an embodiment.
Figures 8D, 8E:
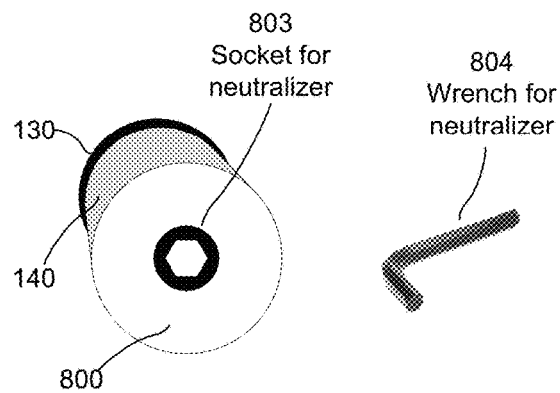
FIG. 8D shows a schematic view of a bottom side of a patch removal device that includes a socket to activate a drug neutralizer.
FIG. 8E shows a schematic view of a wrench for the socket of the patch removal device, in accordance with an embodiment.

Referring to FIG. 8A, in some embodiments, the device 100 may include one or more device identifiers 1020. For example, the identifier(s) 1020 may be on the housing 140 of the device 100. In some cases, the identifier(s) 1020 of the device 100 may be or more MRC, such as a linear MRC or a matrix MRC. In some cases, the identifier(s) 1020 of the device 100 may be a communications device, such as a RFID system or a NFC system. In some embodiments, the device may include an additional locking mechanism that can be used to activate the neutralizer. In some cases, the additional locking mechanism may be disposed at the bottom of the device 800, which is on the opposite side of the locking cap. FIG. 8B shows a schematic view of the bottom side 800 of the device 100 that includes a lock 801 to activate the neutralizer. As shown in FIG. 8C, a corresponding key 802 may be needed to engage with the lock 801 to activate the neutralizer. In another example, FIG. 8D shows a schematic view of the bottom side 800 of the device 100 that includes a socket 803 (e.g., a hex socket) as a mechanism to activate the neutralizer. As shown in FIG. 8E, a corresponding wrench 804 (e.g., a hex wrench) may be needed to engage with the socket 803 to activate the neutralizer.

FIG. 9 is a schematic view of a pairing between the patch 1000 and the device 100 that includes an adhesive material 1110 on its patch removal area, in accordance with an embodiment. The adhesive material may include any type of adhesive as described elsewhere herein. For removal of the patch 1000 from the subject's skin 1009, the device 100 may be applied to the patch 1000 to generate a connection 1111 (e.g., coupling, adhesion, attachment, etc) between the adhesive material 1110 of the device 100 and the patch cover 1010 of the patch 1000. The device 100 may then be pulled away from the subject's skin 1009. In some cases, the connection 1111 may initially occur at a corner or an edge of the patch cover 1010. In some cases, the connection 1111 may initially occur at an entire surface of the patch cover 1010.

Upon generating the connection 1111, the device 100 may be moved (e.g., rolled or translated over the patch 1000), thereby to remove (detach) the patch 1000 from the skin 1009. In some cases, such movement of the device 100 may increase an area of the connection 1111 between the adhesive material 1110 and the patch cover 1010. The device 100 may selectively remove the patch 1000 from the skin 1009, without attaching or adhering to the skin 1009. The adhesive material 1110 may selectively bind (e.g., couple, attach, adhere, etc.) to the patch cover 1010 without binding to the skin 1009. The adhesive material 1110 may preferentially bind to the patch 1000 instead of the skin 1009. The device 100 comprising the adhesive material 1110 may have reduced or no noticeable effect on skin while and after removing the patch 1000. Examples of such noticeable effect include wounds, bruises, cuts, lacerations, scratches, grazes, abrasions, rashes, redness, contusions, lesions, irritations, itchiness, pain, and/or other forms of trauma on the skin 1009. The device 100 may not remove hair from the skin 1009. The device 100 may not pull up the skin 1009 during removal of the patch 1000. In some cases, the device 100 may minimize or prevent injuring the skin during the selective removal of the patch 1000 from the skin 1009, as compared to removing the patch 100 by other means (e.g., manually).

Removing the patch 1000 from the skin 1009 by using the device 100 comprising the adhesive material 1110 may be more efficient and/or less painful in comparison to removing the patch 1000 from the skin 1009 without using the device 100 comprising the adhesive material 1110 (e.g., manual removal by hand). Removing the patch 1000 from the skin 1009 by using the device 100 comprising the adhesive material 1110 may reduce pain or discomfort level experienced by the subject from whom the patch 1000 is removed from by at least 1%, 2%, 3%, 4%, 5%, 10%, 20%, 30%, 40%, 50%, 60%, 70%, 80%, 90%, 95%, or more, in comparison to removing the patch 1000 without using the device 100. Removing the patch 1000 from the skin 1009 by using the device 100 comprising the adhesive material 1110 may reduce pain or discomfort level experienced by the subject from whom the patch 1000 is removed from by at most 100%, 90%, 80%, 70%, 60%, 50%, 40%, 30%, 20%, 10%, 5%, 4%, 3%, 2%, or less, in comparison to removing the patch 1000 without using the device 100.

The reduction of pain or discomfort level experienced by the subject may be attributed to the rolling manner of the core 110 of the device 100 as the core 110 is moved over the skin 1009 to remove the patch. As the core 110 rotates and removes (e.g., lifts) the patch 1000 from the skin 1009, the angle between the skin 1009 and the removed portion of the patch 1000 directly adjacent to the skin 1009 may be less than 90 degrees (e.g., less than 90 degrees, 80 degrees, 70 degrees, 60 degrees, 50 degrees, 40 degrees, 30 degrees, or less). The angle between the skin 1009 and the removed portion of the patch 1000 directly adjacent to the skin 1009 may be less when using the device 100 comprising the adhesive material 1110 than when peeled manually, which may yield an angle of approximately 90 degrees.

The adhesive material 1110 may feel like a solid, semi-solid, or gel (e.g., a soft gel) when in contact with the skin 1009. A surface of the adhesive material that is in contact with the skin 1009 may feel smooth (and not rough) as to not irritate the skin 1009. The adhesive material 1110 may provide a cooling (e.g., a menthol-like) sensation to the skin 1009.

A binding strength of the connection 1111 between the adhesive material 1110 and the patch cover 1010 may be greater than a binding strength between the patch 1000 and the skin 1009 (e.g., between the patch adhesive 1030 or 1035 and the skin 1009). The binding strength of the connection 111 between the adhesive material 1110 and the patch cover 1010 may be at least 1%, 2%, 3%, 4%, 5%, 10%, 20%, 30%, 40%, 50%, 60%, 70%, 80%, 90%, 100%, 200%, or greater than the binding strength between the patch 1000 and the skin 1009. The binding strength of the connection 111 between the adhesive material 1110 and the patch cover 1010 may be at most 200%, 100%, 90%, 80%, 70%, 60%, 50%, 40%, 30%, 20%, 10%, 5%, 4%, 3%, 2%, or less than the binding strength between the patch 1000 and the skin 1009.

The binding strength of the connection 1111 between the adhesive material 1110 and the patch cover 1010 (e.g., a force required to break the between the adhesive material 1110 and the patch cover 1010) may range between about 0.01 Newton (N) to 100 N. The binding strength of the connection 1111 may be at least about 0.01 N, 0.02 N, 0.04 N, 0.06 N, 0.08 N, 0.1 N, 0.2 N, 0.4 N, 0.6 N, 0.8 N, 1 N, 2 N, 4 N, 6 N, 8 N, 10 N, 20 N, 40 N, 60 N, 80 N, 100 N, or more. The binding strength of the connection 1111 may be at most about 100 N, 80 N, 60 N, 40 N, 20 N, 10 N, 8 N, 6 N, 4 N, 2 N, 1 N, 0.8 N, 0.6 N, 0.4 N, 0.2 N, 0.1 N, 0.08 N, 0.06 N, 0.04 N, 0.02 N, 0.01 N, or less.

In some cases, the adhesive material 1110 may come in contact with the skin 1009, but not generate any connection (e.g., adhesion) with the skin 1009. In some cases, the adhesive material 1110 may generate a connection 1112 with the skin 1009. In such a case, the binding strength of the connection 1111 between the adhesive material 1110 and the patch cover 1010 may be greater than a binding strength between the adhesive material 1110 and the skin 1009. Thus, upon moving the device 100 (e.g., over the patch 1000), the connection 1111 may remain intact or increase in size while the connection 1112 is removed (broken off).

The connection 1111 between the adhesive material 1110 and the patch cover 1010 may be reversible. In such a case, the device 100 comprising the adhesive material 1110 may be used multiple times by separating a previously removed patch 1000 from the adhesive material 1110 of the device 100 prior to using the device 100 to remove another patch from the same or a different subject's skin. Alternatively, the connection 1111 between the adhesive material 1110 and the patch cover 1010 may be irreversible. In such a case, the device 100 comprising the adhesive material 1110 may need to be discarded after a single use. In some cases, only the used adhesive material 1110 may need to be removed from the device 100 to expose a new adhesive material for the next use. Alternatively or in addition to, the used adhesive material 1110 may be replaced (swapped) with a new adhesive material for the next use.

A composition of the adhesive material 1110 of the device 100 may be universal for the patch 1000 and other types of coverings (e.g., dressings, bandages, etc.). Alternatively, the composition of the adhesive material 1110 of the device 100 may be different for different coverings (e.g., one adhesive material 1110 composition for BAND AID °, one adhesive material 1110 composition for TEGADERM™, and another adhesive material 1110 composition for fentanyl patches, etc.). Such design may compensate for different binding strengths between the different coverings and the subject's skin.

The device 100 can be used to remove the patch 1000 from the skin 1009 more efficiently. In an example, the device 100 may remove the patch 1000 from the skin 1009 in a fraction of time required to remove the patch 1000 manually (e.g., by hand). The removal of the patch 1000 from the skin 1009 using the device 100 comprising the adhesive material 1110 may take about 1 seconds (sec) to 10 sec. The removal of the patch from the skin 1009 using the device 100 comprising the adhesive material 1110 may take at least about 1 sec, 2 sec, 3 sec, 4 sec, 5 sec, 6 sec, 7 sec, 8 sec, 9 sec, 10 sec, or more. The removal of the patch from the skin 1009 using the device 100 comprising the adhesive material 1110 may take at most about 10 sec, 9 sec, 8 sec, 7 sec, 6 sec, 5 sec, 4 sec, 3 sec, 2 sec, 1 sec, or less.

Any other forms of the device 100 (e.g., a film, a roller, a wearable article such as a glove, etc.) comprising the adhesive material 1110 may be used to selectively remove the patch 1000 and/or any other forms of coverings (e.g., dressings, bandages, etc.) disclosed herein from the skin 1009.

In some cases, the adhesive material 1110 itself may be the device to selectively remove the patch 1000 from the skin 1009. The adhesive material 1110 may not need a carrier (e.g., the device 100) to be picked up and handled by hand. In an example, the adhesive material 1110 may be a solid-like or gel-like object. In such a case, a user (e.g., the practitioner) may hold the adhesive material 1110 by hand and use it to remove any covering from a subject's skin.

FIG. 10 shows a schematic view of a covering removal device 2000 that is to be used in selectively removing (detaching) a covering from a subject's skin. The device 2000 may be a roller that comprises a handle 2002 and a core 2005. The handle 2002 may comprise one or more arms 2003 that is coupled to the core 2005. The arm(s) 2003 may be coupled to one or more sides 2004 of the core 2005. The core 2005 may also comprise an adhesive material 2001 on its surface (e.g., on the circumferential external surface of the core 2005). The adhesive material 2001 may comprise any of the adhesive material disclosed herein. The device 2000 may move (e.g., translate and/or rotate) over the subject's skin to remove the covering from the skin.

FIGS. 11A-G show schematic side views of the device 2000 being used to selectively remove a covering 3000 from the skin 1009. Referring to FIG. 11A, the core 2005a of the device 2000 may have a circular cross-section, as indicated by a side view 2004a of the core 2005a. The device 2000 may be brought in contact with a portion (e.g., a corner or an edge) of the outer surface of the covering 3000 (opposite the skin 1009) to make an initial connection (e.g., binding or adhesion) between the adhesive material 2001 of the core 2005a of the device 2000 (not shown) and the covering 3000. Referring to FIG. 11B, the device 2000 may be translated 2011 across the skin 1009 and the core 2005a of the device 2000 may be rotated 2010 over the covering 3000 on the skin 1009 to remove at least a portion of the covering 3000 from the skin 1009. Referring to FIG. 11C, the covering 3000 may be completely removed from the skin 1009 by the device 2000, with the covering 3000 remaining on the adhesive material 2001 of the core 2005a of the device 2000.

Referring to FIG. 11D, a cross-section of the core 2005b of the device 2000 (or any other device configured to remove a covering from the skin) may comprise both a non-flat region and a flat region. In this example, the cross-section of the core 2005b may be a major segment of a circle that is intercepted buy a chord (i.e., the flat region), as illustrated in the side view 2004b of the core 2005b. The flat region of the core 2005b may be configured to enhance and/or maximize an initial contact and connection between a connection mechanism (e.g., adhesive material) that disposed on the outer surface of the core 2005b and a leading edge of the covering 3000 (e.g., the patch). Referring to FIG. 11E, after generation of the contact between the flat region of the core 2005b and the leading edge of the covering 3000, the device 2000 may be translated 2011 across the skin 1009 and the core 2005b of the device 2000 may be rotated 2010 over the covering 3000 on the skin 1009 to remove at least a portion of the covering 3000 from the skin 1009. Referring to FIG. 11F, the covering 3000 may be completely removed from the skin 1009 by the device 2000, with the covering 3000 remaining on the adhesive material 2001 of the core 2005b of the device 2000.

FIG. 11G shows examples of the core 2005 with different cross-sectional shapes and/or dimensions. In one example, the core 2005c may have a cross-section that is circular. In one example, the core 2005d may have a cross-section that is a major segment of a circle that is intercepted by a flat chord. A major diameter of the cross-section of the core 2005d may be smaller than the diameter of the circular cross-section of the core 2005c. In one example, the core 2005e may have a cross-section that is approximately circular with at least one protrusion (e.g., at least 1, 2, 3, 4, 5, or more protrusion(s)). In this example, the core 2005e may have a cross-section that is circular with one protrusion. The protrusion may have two or more flat portions. In some examples, the core 2005f and the core 2005g may both have a cross-section that is each a major segment of a circle that is intercepted by a flat chord. A major diameter of the cross-section of the core 2005f may be the same as a major diameter of the cross-section of the core 2005g. The flat chord of the cross-section of the core 2005f may be longer than the flat chord of the cross-section of the core 2005g.

FIG. 12 shows schematic views of the device 2000 and its use in removing (detaching) the covering 3000 from the subject's skin 1009. The device 2000 may selectively remove the covering 3000 from the skin 1009. The device 2000 comprising the adhesive material 2001 may have reduced or no noticeable effect on skin 1009 while and after removing the covering 3000. Examples of such noticeable effect include wounds, bruises, cuts, lacerations, scratches, grazes, abrasions, rashes, redness, contusions, lesions, irritations, itchiness, pain, and/or other forms of trauma on the skin 1009. The device 2000 may not remove hair from the skin 1009. The device 2000 may not pull up the skin 1009 during removal of the covering 3000. In some cases, the device 2000 may minimize or prevent injuring the skin during the selective removal of the covering 3000 from the skin 1009, as compared to removing the covering 3000 by other means (e.g., manually). Such removal of the covering 3000 from the skin 1009 may not cause one or more injuries on the skin 1009. The device 2000 may have an outwardly facing surface that comprises a connection mechanism. In some cases, the connection mechanism may be the adhesive material 2001. In some cases, the device may be a roller that is configured to rotate 2010 along its central axis such that the outwardly facing surface is rolled over the subject's skin 1009 as the device 2000 is moved across 2011 the skin 1009.

The device 2000 may be moved over the covering 3000 that is adhered to the skin 1009. Examples of the covering 3000 may include patches, pads, films, dressings, plasters, bandages, wrappers, strips, patches, gauzes, tapes, or the like that adheres to a bodily surface (e.g., healthy and/or wounded skin) of a subject. The covering 3000 may be medicated or not medicated. In some cases, the covering 3000 may be a film that is applied (e.g., attached) over an inner covering (e.g., a medicated patch), and the device 2000 may selectively remove both the covering 3000 and the additional covering underneath the covering 3000 from the skin 1009 at once. Alternatively, the device 2000 may selectively remove the covering 3000 from the additional covering and the skin 1009, and the same or a different device 2000 may be used to remove (e.g., selectively remove) the additional covering. In an example, the covering 3000 may be TEGADERM™, and the additional covering underneath the TEGADERM™ may be a medicated patch.

Figure 12A:
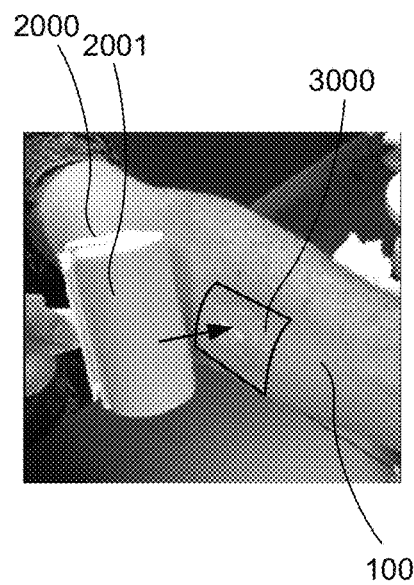
FIGS. 12A through 12E are schematic illustrations showing a selective removal of a covering from a bodily surface of a subject using a covering removal device, which selective removal does not injure the bodily surface of the subject, in accordance with some embodiments.

Referring to FIG. 12A, the device 2000 comprising the adhesive material 2001 on the outwardly facing surface may be applied to a portion (e.g., one or more corners, one or more sides, etc.) of the covering 3000 adhered on the subject's skin 1009. A connection (e.g., adhesion) may be generated between the adhesive material 2001 and an outer surface of the covering 3000.

Figure 12B:
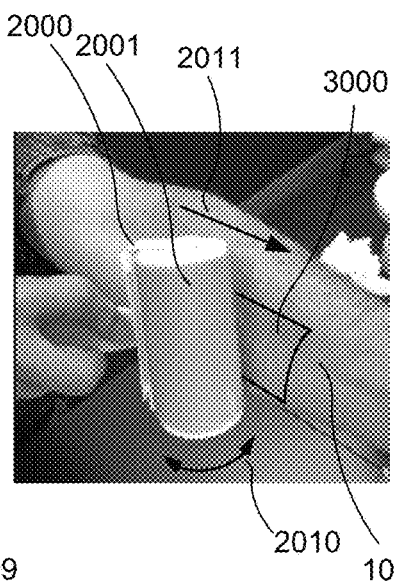

Referring to FIG. 12B, the device 2000 may be moved 2011 and rolled 2010 over the covering 3000 and the skin 1009 adjacent to the covering 3000. An area of the connection between the adhesive material 2001 and the covering 3000 may increase as the device 2000 is (i) moved across 2011 the covering 3000 and (ii) rotates 2010 around its central axis. A binding strength of the connection between the adhesive material 2001 and the covering 3000 may be greater than a biding strength of the covering 3000 to the skin 1009. Thus, as the device 2000 moves 2011 and rotates 2010 over the skin 1009, the portion of the covering 3000 in contact with the adhesive material 2001 of the device 2000 may be removed from the skin 1009.

Figure 12C:
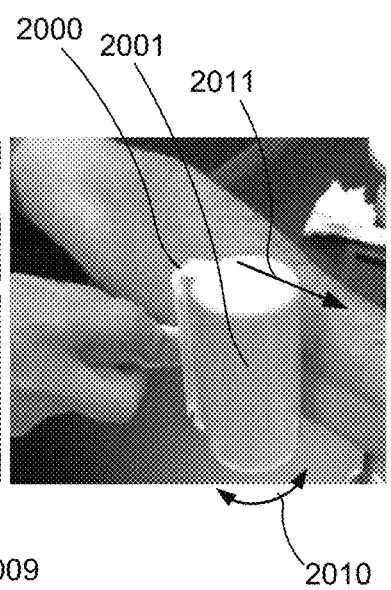

Referring to FIG. 12C, the device 2000 may be moved 2011 and rolled 2010 over the skin 1009 until the device 2000 is moved over an entire surface of the covering 3000. In some cases, the device 2000 may be moved over the skin 1009 in an area greater than the entire surface of the covering 3000 to ensure a complete and selective removal of the covering 3000 from the skin 1009.

Figure 12D:
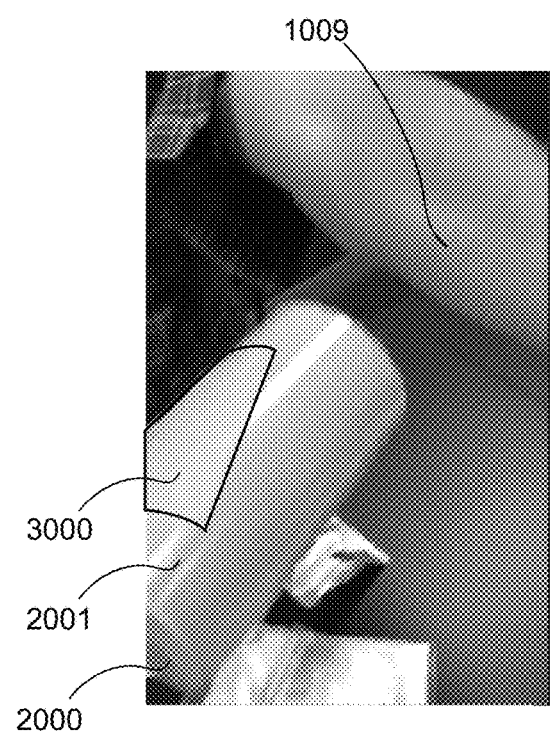
Figure 12E:
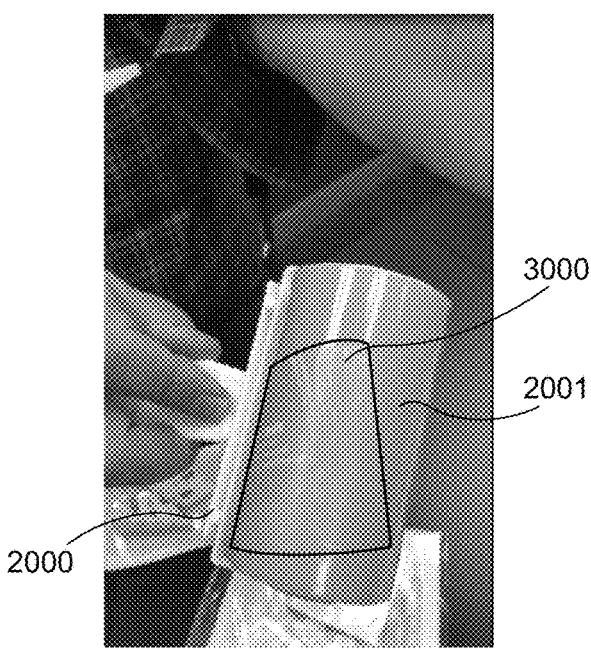

Referring to FIG. 12D, the device 2000 may selectively remove the covering 3000 from the skin 1009. Due to the connection between the adhesive material 2001 of the device 2000 and the covering 3000, the covering 3000 may remain intact to the adhesive material 2001. Another view of the covering 3000 intact on the adhesive material 2001 of the device 2000 is shown in FIG. 12E. In some cases, the used covering 3000 may be removed from the device 2000 and disposed in an appropriate manner. In some cases, the entire device 2000 comprising the used covering 3000 may be disposed in an appropriate manner.

FIG. 13 shows schematic views of a 1-piece device 2200 configured to remove and retrieve a covering (e.g., a patch) 3000 from a skin 1009 of a subject. Referring to FIG. 13A, the device 2200 may comprise a handle 2202 for a user (e.g., a practitioner) to hold the device while removing the covering 3000 from the subject. The handle may not comprise any adhesive. The device 2200 may comprise one or more adhesive materials as connection mechanism(s) to bind the covering 3000. The device 2200 may comprise a non-flat (e.g., round) adhesive material 2204 and a flat adhesive material 2206. The non-flat adhesive material 2204 may comprise of a low-strength adhesive material that selectively binds the covering, but not the skin 1009. The flat adhesive material 2206 may comprise of a high-strength adhesive material that exhibits a higher adhesive strength than the low-strength adhesive material. The flat adhesive material 2206 may be presented as a single zone or as a plurality of zones. In some cases, the flat adhesive material 2206 may comprise a center flat adhesive zone 2206a and one or more additional flat adhesive zones 2206b. The center flat adhesive zone 2206a may be configured to bind to a leading edge of the covering. A width of the center flat adhesive zone 2206a may be smaller than a width of the smallest covering to be removed to prevent contact between the high adhesive material of the center flat adhesive zone 2206a to the skin. In some cases, the center flat adhesive zone 2206a alone may sufficient to bind and retrieve a small covering. For larger coverings, at least a portion of the additional flat adhesive zone(s) 2206b may be exposed (e.g., via removing one or more layers that cover the additional flat adhesive zone(s) 2206b) to generate a higher initial contact area between the device 2202 and the leading edge of the larger coverings. In some cases, the device may comprise one or more notches 2208 adjacent to the center flat adhesive zone 2206a. The notch(es) 2208 may allow the user to visualize and correctly align the center flat adhesive zone 2206a of the device 2200 to a leading edge of the covering 3000. The notch(es) 2208 may help avoid undesired contact between the center flat adhesive zone 2206a and the skin 1009.

Referring to FIG. 13B, a schematic side view of the device 2200 shows the non-flat (e.g., round) adhesive material 2204 and the flat-adhesive material 2206 of the device 2200. The device may be brought towards the covering 3000 on the subject's skin 1009 to generate an initial contact between the flat-adhesive material 2206 of the device 2200 to the covering 3000. Referring to FIG. 13C, a schematic top-down and semi-transparent view of the device 2200 shows the non-flat adhesive material 2204, along with the flat-adhesive material 2206 that is disposed on a bottom portion of the device 2200. The schematic top-down and semi-transparent view of the device 2200 also shows the notch(es) 2208 of the device 2200 that allows a partial visualization of an object that is underneath the non-flat adhesive material 2204 of the device 2200. Referring to FIG. 13D, when the device 2200 is brought in towards the covering 3000, the partial visualization of the covering 3000 through the notch(es) 2208 of the device 2200 may help align the flat-adhesive material 2206 of the device 2200 to a leading edge of the covering 3000 without generating any undesirable contact between the flat-adhesive material 2206 and the skin.

Referring to FIGS. 13E and 13F, the flat-adhesive material 2206 of the device 2200 may be covered with one or more removable sheet 2210. When using the device 2200 to remove and retrieve the covering 3000, (i) a center of the removable sheet 2210 alone or (ii) the center of the removable sheet 2210 and an additional portion of the removable sheet 2210 may be removed to substantially match coverings with different sizes/dimensions. The sizes/dimensions of the coverings (e.g., drug patches) may correspond to the respective doses of the drug in the coverings. Referring to FIG. 13E, multiple portions of a removable sheet 2210a may be coded with numbers (e.g., 12, 25, 50, 75, and/or 100), thereby corresponding to the respective sizes/dimensions and/or drug doses of the covering. Referring to FIG. 13F, multiple portions a removable sheet 2210b may be coded with different colors and/or patterns, thereby corresponding to the respective sizes/dimensions and/or drug doses of the covering.

FIG. 14 shows schematic views of a 2-piece device 2400 configured to remove and retrieve a covering (e.g., a patch) 3000 from a skin 1009 of a subject. Referring to FIG. 14A, the device 2400 may comprise a housing 2410, a core 2420, and a cap 2450. The core 2420 may be movable relative to the housing 2410 (e.g., within the housing 2410). When the core 2420 is completely inside the housing 2410, the cap 2450 may seal the opening of the housing 2410 to prevent access to the core 2420. When the core 2420 is to be used for removal of the covering 3000, the cap 2450 may be removed. The cap 2450 may be kept separately or stored on the housing 2410 at an opposite end of the opening, as shown in FIG. 14A. With the cap 2450 removed from the opening, the core 2420 may be configured to be partially deployed out of a second end of the housing 2410, wherein the second end is opposite the first end. The core 2420 may comprise a handle 2422 for a user to hold to partially deploy the core 2420 out of the housing 2410.

Referring to FIG. 14B, the core 2420 may be partially deployed out of the housing 2410 to expose a connection mechanism (e.g., adhesive material) for binding and retrieving the covering 3000. For example, at least a non-flat adhesive material 2426 of the core 2420 may be exposed. Alternatively or in addition to, a flat adhesive material of the core 2420 may be exposed. The core 2420 may comprise one or more notches 2428 to help align the core 2420 to a leading edge of the covering 3000. The core 2420 may comprise a ring with one or more indents. The user may use one's fingers to hold or press the ring to prevent the core 2420 from rotation relative to the covering 3000 when generating the initial contact between the core 2420 (e.g., a high adhesive material of the core 2420) and the covering 3000. The ring may comprise a major indent 2430 that indicates a start position of the core 2420. In an example, the major indent 2430 may be facing upwards when generating an initial contact between the adhesive material of the core 2420 to the leading edge of the covering 3000.

Referring to FIG. 14B, the core 2420 may comprise a carriage (e.g., an end tubing) at an end opposite the handle 2422. A surface of the carriage 2423 may comprise one or more stopper rings (e.g., one or more rubber stoppers) 2424. The stopper ring(s) 2424 may be in contact with an inner surface of the housing 2410. The stopper ring(s) 2424 may be configured to hold the core 2420 in place within the housing 2420. Alternatively or in addition to, a portion of the inner surface of the housing 2410 may be coated with a stopper material (e.g., a rubber material), thereby to hold the core 2420 in place within the housing 2420.

FIG. 14C shows a schematic cross-sectional view of a device 2400a, comprising a housing 2410, a core 2420, and a cap 2450. For the device 2400a, the core 2420 may be configured to translate and rotate relative to the housing 2410. The core 2420 may be inserted inside the housing 2410, and the cap 2450 may seal an opening of the housing 2410 to prevent any access to the core 2420. When the cap 2450 is sealing the housing 2410, the cap 2450 may be in contact with a sealant 2416 (e.g., a rubber material) of the housing 2410. The sealant 2416 may make contact with the cap 2450 and thus make the device airtight and/or watertight. The core may comprise the carriage 2423, and a surface of the carriage 2423 may comprise one or more stopper rings 2424 that are in contact with the inner surface of the housing 2410. The stopper ring(s) may prevent movement (e.g., rotation and/or translation) of the core 2420 relative to the housing 2410 in the absence of an external force (e.g., manual pulling of the core 2420 out of the housing 2410). The carriage 2423 may be coupled to the core 2420 via a pivot 2423.

Referring to FIG. 14C, an inner surface of the cap 2450 may comprise a locking tab 2452. At the same time, an inner portion of the housing 2410 that is configured to be in contact with the cap 2450 may comprise a locking indent 2412 and a locking positioning mechanism 2414. The locking tab 2452 of the cap 2450 and the locking indent 2412 of the housing 2410 may be compatible with each other to securely fasten the cap 2450 onto the housing 2410. The locking positioning mechanism 2414 of the housing 2410 may be configured to ensure that the cap 2450 is positioned properly. A proper positioning of the cap 2450 relative to the housing 2410 may allow a proper visualization of the covering 3000 retrieved on the core 2420 or any identifier (e.g., barcode) provided on the covering 3000 or the core 2420.

FIGS. 14D and 14E show schematic illustrations of a device 2400b, comprising a housing 2410, a core 2420, and a cap 2450. Referring to FIG. 14D, the cap 2450 may be removed from an opening of the housing 2410 and stored on an end opposite the opening, thereby to allow the core 2420 to be deployed (e.g., partially deployed) out of the housing 2410. The core 2420 may comprise a handle 2422 so the user can pull on the core 2420 for its deployment. At least a portion of the housing 2410 may be transparent or semi-transparent to allow visualization of a recovered patch on the core 2420 inside the housing 2410. For the device 2400b, the core 2420 may be configured translate, but not rotate, relative to the housing 2410. The core 2420 and the housing 2410 may be connected via a shaft 2434 (e.g., a keyed shaft) to prevent the rotation of the core 2420 relative to the housing 2410.

Referring to FIG. 14E, the housing 2410 of the device 2400b may comprise a sealant that is configured to be in contact with the cap 2450 to make the device 2400b airtight and/or watertight. The core 2420 may further comprise a core lock 2436. Upon the partial deployment of the core 2420 out of the housing 2410, the core lock 2436 may connect with one or more components of the housing 2410 to prevent a complete deployment of the core 2420 out of the housing 2410. The core lock 2436 may thus ensure that the core 2420 and the housing 2410 are connected. Additionally, the core 2420 may have variations of the handle 2422, as exemplified in 2422a and 2422b.

FIGS. 14F and 14G show schematic illustrations of a device 2400c, comprising a housing 2410, a core 2420, and a cap (not shown). Referring to FIG. 14F, the housing 2410 may comprise housing layers 2410a, 2410b, and 2410c that are operatively and/or mechanically coupled to one another. The housing layer 2410c may be configured to conceal the core 2420 prior to its use to retrieve a covering 3000. Prior to use of the device 2400c, a portion of the housing layer 2410c may be inserted inside the housing layer 2410b. The housing layers 2410c and 2410b may be configured to rotate, but not translate, relative to each other. Prior to use of the device 2400c, a majority of the housing layer 2410b may be inserted inside the outermost housing layer 2410a. The housing layers 2410b and 2410a may be configured to translate, but not rotate, relative to each other. Prior to use of the device 2400c, a safety clip 2418 may be installed on the housing layer 2410a or at a junction between the housing layers 2410a and 2410b. The safety clip 2418 may (i) prevent the relative translation between the housing layers 2410a and 2410b, thereby to (ii) prevent the relative rotation between the housing layers 2410*b* and 2410*c*. The safety clip 2418 may also serve to prevent the core 2420 of the device 2400*c* from unintentionally locking into the housing 2410, which locking mechanism (e.g., neutralization, etc.) is configured to be activated upon retrieval of the covering (e.g., patch).

Referring to FIG. 14G, upon removal of the safety clip 2418 from the outermost housing layer 2410*a*, the intermediate housing layer 2410*b* (along with the innermost housing layer 2410*a* and the core 2420) may be translated (e.g., partially or completely) out of the outermost housing layer 2410*a* (as illustrated in FIG. 14G, top). Afterwards, the user (e.g., the practitioner) may use one hand to hold the innermost housing layer 2410*c*, while using the other hand to hold the intermediate housing layer 2410*b*. Subsequently, the user may use both hands to rotate the housings layers 2410*c* and 2410*b* relative to each other, thereby to activate deployment of the core 2420 out of the innermost housing layer 2410*c* (as illustrated in FIG. 14G, bottom). The rotating piece may be the intermediate housing layer 2410*b*, the innermost housing layer 2410*c*. The core 2420 may translate and rotate during the deployment. One or more of the housing layers 2410*a*, 2410*b*, and 2410*c* may have a plurality of protrusions on the surface to facilitate and improve handgrips.

FIG. 15 shows schematic views of a different 2-piece device 2600 configured to remove and retrieve a covering (e.g., a patch) 3000 from a skin 1009 of a subject. Referring to FIG. 15A, the device 2600 may comprise a housing 2610 and a core 2620, wherein the core comprises one or more adhesive materials 2622 capable of binding the covering 3000. The core may also comprise a cap 2621, which is part of a locking mechanism that seals the core 2620 within the housing 2610, either prior to or subsequent to the use of the device 2600 to retrieve the covering 3000. The housing 2610 and the core 2620 may be configured to rotate and/or translate relative to each other.

Referring to FIG. 15A, the housing 2610 may comprise a plurality of layers, for example, an outer housing layer 2610*a* and an inner housing layer 2610*b*. The housing layers 2610*a* and 2610*b* may be configured to rotate relative to each other. A portion of the outer housing layer 2610*a* may be an opening 2612 to allow visualization of a portion of the inner housing layer 2610*b*. Additionally, the inner housing layer 2610*b* may comprise a first surface that is opaque (not transparent or semi-transparent), and a second surface that is transparent or semi-transparent. The inner housing layer 2610*b* may rotate relative to the outer housing layer to expose the opaque surface and/or the transparent surface through the opening 2612. As shown in FIG. 15A (bottom), prior to the use of the device 2600, the housing layers 2610*a* and 2610*b* may be disposed such that only an empty portion of the opaque surface of the inner housing layer 2610*b* is visualized through the opening 2612 of the outer housing layer 2610*a*.

Referring to FIG. 15B (top), a portion of the core 2620 may be deployed out of the housing 2610. In this example, the core 2620 may be translated out of the housing 2610. Referring to FIG. 15B (bottom), a schematic cross-sectional view of the device 2600 exhibits how the core 2620 is prevented from completely deploying out of the housing 2610. The housing 2610 may comprise one or more rings or tabs (e.g., one or more flex tabs made of rubber materials) 2613, with an effective inner diameter. The bottom portion of the core 2620 may have an effective outer diameter that is greater than the effective inner diameter of the ring(s)/tab(s) 2613. Thus, the ring(s)/tab(s) 2613 may make contact with the bottom portion of the core 2620 and prevent the core 2620 from completely sliding out of the housing 2610. Furthermore, the core 2620 may comprise a cup (e.g., a fluid cup) 2622 configured to hold a neutralizer (e.g., chemical decontaminants, drug antagonists, mechanical encapsulant, etc.) to deactivate residual pharmaceuticals on the retrieved covering 3000. Prior to the use of the device 2600, a surface (e.g., a bottom surface) of the cup 2624 may be sealed (e.g., by a plastic film) to retain the neutralizer within the cup. In some cases, the cup 2624 may be disposed inside the bottom portion of the core 2620. Alternatively or in addition to, such cup for holding the neutralizer may be disposed at a portion of the housing 2610.

Referring to FIG. 15C, subsequent to retrieval of the covering by the core 2620, the core 2620 along with the covering may be retrieved (e.g., translated or pushed) back into the housing 2610. During the retrieval of the core 2620 back into the housing 2610, a neutralization activation mechanism 2615 (e.g., protrusions, rods, blades, etc.) of the housing 2610 may activate the neutralizer cup 2624 disposed at the bottom of the core 2600, thereby inducing a release of the neutralizer of the pharmaceutical to the retrieved covering inside the device 2600. In an example, the neutralization activation mechanism 2615 may be one or more protrusions, and the protrusion(s) may break open the seal of the cup 2624 to release the neutralizer. The device 2600 maybe sealed to prevent leakage of the released neutralizer out of the device 2600. In some examples, on the opposite end of the core 2620, the ring(s)/tab(s) 2613 and one or more stoppers (e.g., rubber O-rings) 2626 of the core 2620 may seal the core 2620 within the housing 2610.

Referring to FIG. 15D, subsequent to the retrieval of the core 2620 into the housing 2610, the outer housing layer 2610*a* may be rotated (e.g., 300 degrees) to a predesignated stopping point relative to the inner housing layer 2610*b* to expose at least a portion of the transparent surface of the inner housing layer 2610*b* through the opening 2612. As such, the user may be able to visualize at least a portion of the retrieved covering on the core 2620 through the transparent surface of the inner housing layer 2610*b* and through the opening 2612. Furthermore, the rotation of the outer housing layer 2610*a* may also expose a portion of the inner housing layer 2610*b* that comprises an identifier 2614. The identifier may comprise a barcode 2614*a* that is specific to the device 2600. The identifier may comprise a signature zone 2612, in which the user (e.g., the practitioner) may write his or her signature to indicate retrieval of the covering.

FIG. 16 shows schematic views of a refillable device 4000 for removing a covering 3000 (e.g., a drug patch) from a skin of a subject. Referring to FIG. 16A, the refillable device 4000 may comprise a core cartridge 4100. Referring to FIG. 16B, the core cartridge 4100 may comprise a removable cartridge cap 4105, an outer layer 4110, and an inner layer 4115 that comprises on its surface a connection mechanism (e.g., one or more adhesive materials) to bind and retrieve the covering 3000 from the skin of the subject. The outer layer 4110 and the inner layer 4115 may be connected by a first quick release coupling mechanism. Referring to FIGS. 16C, the cap 4105 may be removed from the core cartridge 4100, and the core cartridge 4100 may be installed (e.g., inserted) 4105 into a housing 4200. In some cases, the cap 4105 may be intact on the core cartridge 4100 during the installation into the housing 4200, after which the cap 4105 may be removed. Referring to FIG. 16D, an assembled device 4000 is shown, comprising the housing 4200 that houses the core cartridge 4100 that includes the outer layer 4110 and the inner layer 4115. The outer layer 4110 and the housing 4200 may be connected by a second quick release coupling mechanism. The first quick release coupling mechanism between the outer layer 4110 and the inner layer 4115 of the core cartridge 4100 may be configured such that the core cartridge 4100 may need to be installed inside the housing 4200 in order to be able to at least partially eject the inner layer 4115 out of the outer layer 4110. Referring to FIG. 16E, upon activation of the first quick release coupling mechanism core (e.g., by a button on the housing 4200), at least a portion of the inner layer 4115 of the core cartridge 4100 may be deployed 4510 out of the outer layer 4110, while at least a portion of the outer layer 4110 of the core cartridge 4100 remains inside the housing 4200. Referring to FIG. 16F, subsequent to removal of the covering 3000 by the inner layer 4115 of the core cartridge 4100, the inner layer 4115 of the core cartridge 4100 and the covering 3000 may be retrieved 4515 back into the outer layer 4110 of the core cartridge 4100. Referring to FIG. 16G, afterwards, an entire assembly of the core cartridge 4100 including the outer layer 4110, the inner layer 4115, and the retrieved covering 3000 may be released 4520 from the housing 4200. Referring to FIG. 16H, the used core cartridge 4100a may be sealed with the cap 4105, then collected for tracking and disposal of the covering 3000, for example. The cap 4105 may prevent access to and/or tampering with the retrieved covering on the inner layer of the first core cartridge. Subsequently, an additional core cartridge may be installed into the housing 4200 for removal of an additional covering. A connection mechanism between the cap 4105 and the outer layer 4110 and/or the inner layer 4115 of the core cartridge 4100 may include a luer-type fitting.

Referring to the refillable device 4000 shown in FIG. 16, a locking mechanism of the outer layer 4110 of the core cartridge 4100 to cover and lock in the respective inner layer 4115 and the retrieved covering 3000 may be activated by the housing 4200 prior to the release of the core cartridge 4100 from the housing 4200. Alternatively or in addition to, such locking mechanism between the outer layer 4110 and the inner layer 4115 of the core cartridge 4100 may be activated subsequent to the removal of the core cartridge 4100 from the housing 4200.

FIG. 17 is a schematic illustration of different components of the device 3100 to remove a covering (e.g., a patch) from a subject. The device 3100 may comprise a housing 3105 that covers or protects a core 3110 prior to the use of the device 3100. The housing 3105 may comprise at least one sealant 3106 to make the device 3100 airtight and/or watertight. The sealant 3106 may be a gasket or an O-ring (e.g., a rubber O-ring). The housing 3105 may comprise at least 1, 2, 3, 4, 5, or more sealants. The housing 3105 may comprise at most 5, 4, 3, 2, or 1 sealant. In some examples, the housing 3105 may be a tube comprising a sealant 3106 on either or both ends of the housing 3105. The housing 3105 may further comprise or may be coupled to a lock 3120. The lock may need to be opened or broken prior to use of the device 3100. The device 3100 may not be functional with the lock 3120 intact. In some examples, the lock 3120 may be a clip that locks (or hooks) into a portion of the housing, such as, for example, a lid 3122 of the housing 3120. The housing 3105 may further comprise an identifier 3125. The identifier 3125 may be disposed and hidden from view or access prior to use of the device 3100. In some examples, the identifier 3125 may be disposed underneath at least a portion of the lid 3122, thereby hidden from any excess by a user of the device 3100 prior to its use. The identifier 3125 may comprise a signature zone or one or more machine readable codes. Subsequent to the use of the device 3100 to remove a covering, at least a portion of the device 3100 (e.g., the lid 3122) may be moved (e.g., rotated) relative to the device 3100, thereby revealing the identifier 3125 and access to the identifier 3125.

Referring to FIG. 17, the core 3110 of the device 3100 may comprise one or more connection mechanisms to bind the covering. In some cases, the core 3110 may comprise one or more adhesive materials to bind the covering. In some examples, the core 3110 may comprise a round surface 3111 and a flat surface 3112. The adhesive strengths of the round surface 3111 and the flat surface 3112 may be different, e.g., the flat surface 3112 may exhibit a stronger binding strength to a target surface than the round surface 3111 for generating an initial contact between the device 3100 and the covering. The adhesive strength of the round surface 3111 may be sufficient to selectively bind the covering and not the skin adjacent to the covering. In some cases, only a portion 3113 of the flat surface 3112 of the core 3110 may exhibit the stronger binding strength, in comparison to the flat surface 3112. The size of the portion 3113 of the flat surface 3112 may be fixed for a plurality of coverings with different sizes. Alternatively, the size of the portion 3113 of the flat surface 3112 may vary depending on the size of each covering. Prior to use of the device, at least a portion of the connection mechanism (e.g., adhesive material(s)) of the core 3110 may be covered by a protective layer 3115 (e.g., a film, such as a polymeric film).

Referring to FIG. 17, the core 3110 may be operatively coupled to a source 3130 of a neutralizer. The neutralizer (e.g., chemical decontaminants, drug antagonists, mechanical encapsulant, etc.) may be activated upon or subsequent to retrieval of a covering by the core 3110. The activated neutralizer may deactivate or physically seal residual pharmaceuticals on the retrieved covering. The source 3130 of the neutralizer may be a container, cup, capsule, vial, etc. for storing the neutralizer. The source 3130 may be protected by a housing 3134. The housing 3134 may prevent damage and uncontrolled release and/or activation of the neutralizer. At least a portion (e.g., a surface) of the source 3130 may comprise a seal 3132. The seal 3132 may be broken by one or more components of the device 3100 to release and/or activate the neutralizer contained in the source 3130. In an example, the seal 3132 of the source 3130 may be disposed adjacent to a cap 3136 that comprises a mechanism (e.g., a protrusion 3137, such as, for example, a needle) to break or penetrate the seal 3132. Thus, in some examples, upon retrieval of the covering by the core 3110 and loading of the core 3110 back into the housing 3105, the source 3130 may be directed in a direction towards the cap 3136, such that the cap 3136 breaks the seal 3132 of the source 3130 to release and/or activate the neutralizer.

FIG. 18 shows schematic illustrations of systems and methods of using the device 3100 to remove a covering 1000 (e.g., a patch) from a subject. Referring to FIG. 18A, the method may comprise releasing the lock 3120 of the lid 3122 from the lock collar 3124 of the housing 3105 (process 3150). Referring to FIG. 18B, the method may comprise detaching the lock 3120 from the lid 3122 (process 3155). Additionally, the method may comprise drawing (e.g., pulling, extracting, etc.) the core 3110 out of the housing 3105 (process 3160). For example, a user (e.g., a practitioner) may pull on the lid 3122 to pull out the core 3110 out of the housing 3105. In some cases, the core 3110 and the housing 3105 may be operatively coupled such that there is at least one fixed position (e.g., a locking position) to prevent the core 3110 from being completely pulled out of the housing 3105. Referring to FIG. 18C, the method ma comprise removing the protecting layer 3115 (e.g., an adhesive backer) from the core 3110 to reveal/expose the round surface 3111 and the flat surface 3112 of the core 3110, which surfaces may comprise a connection mechanism (e.g., adhesive material(s)) to bind to the patch 1000 (process 3165). Referring to FIG. 18D, the method may comprise holding the device 3100 by the housing 3105 of the device 3100 (process 3170). The method may comprise aligning the initial contact surface 3113 of the flat surface 3112 of the core 3110 to an edge of the patch 1000, to make a connection between the core 3110 and the patch 1000 (process 3172). The method may comprise translating and/or rotating the core 3110 over the patch 1000 to remove the patch 1000 from the subject's skin (process 3174). In some cases, both the core 3110 and the housing 3105 may be rotated and translated over the patch 1000 during the removal of the patch 1000. Alternatively, the core 3110 may rotate relative to the housing 3105 during the removal of the patch 1000. Referring to FIG. 18E, the method may comprise completely removing the patch 1000 onto the core 3110 of the device 3100 (process 3176). Referring to FIG. 18F, the method may comprise depressing (e.g., pressing down) the core 3100 that includes the removed patch 1000 into the housing 3105 (process 3180). The depression may lock the device 3100 and seal the core 3110 into the housing 3105, thus preventing any further access to the retrieved patch 1000. The method may comprise breaking the seal 3132 of the source of neutralizer 3130 upon depression of the core 3110 into the protrusion 3137 of the cap 3136 to release and/or activate the neutralizer that is contained in the source 3130 of the neutralizer (process 3182). The method may comprise moving (e.g., vibrating, shaking, swinging, jiggling, etc.) the device 3100 to neutralize the patch 1000 with the released and/or activated neutralizer within the device 3100 (process 3184). The method may comprise twisting the lock collar 3124 of the housing 3105 to reveal the identifier (process 3186). As shown in FIG. 18D, the device 3100 may be compatible for a right-handed use, wherein the user may hold the device 3100 by the right hand to remove the covering 1000 from the subject. The device 3100 may be designed to be compatible for a left-handed use, wherein the user is holding the device 3100 by the left hand to remove the covering 1000 from the subject. In such a case, the direction of rotation 3174-2 of the core 3110 may be opposite of the direction of rotation 3174 of the core 3110 as provided in FIG. 18D. In another alternative, the device 3100 may be configured to be compatible for both the right-handed use and the left-handed use. In such a case, the core 3110 may be configured to rotate relative to the housing 3105 in both directions, and the direction of rotation of the core 3110 may be determined by a direction of translation of the device 3100 over the covering 1000.

FIG. 19 shows schematic illustrations of systems and methods of using a device 3200 to remove a covering 1000 (e.g., a patch) from a subject. In some cases, the device 3200 may utilize various aspects of the system and method for removing a covering by the device of the present disclosure, e.g., the device 3100. Referring to FIG. 19A, the device 3200 may comprise a core 3110 comprising one or more connection mechanisms (e.g., adhesive(s)) to bind the covering. At least a portion of a flat surface 3112 of the core 3110 may exhibit a stronger binding strength to a target surface (e.g., a covering, such as, for example, a patch) than a round surface 3111 of the core 3110. In this example, a portion 3113 of the flat surface 3112 may exhibit the stronger binding strength, in comparison to the flat surface 3112. The device 3200 may comprise a handle 3210. Prior to use, at least a portion of the round surface 3111 and the flat surface 3112 of the core 3110 may be covered by a protecting layer 3115. Prior to use, at least a portion of the handle 3210 may be inserted (e.g., hidden) inside the core 3110. The device 3200 may comprise a base 3220 (e.g., a ring, tube, sheath, etc.) that is movable relative to the core 3110. Alternatively, the core 3110 may be movable relative to the base 3220. In another alternative, both the core 3110 and the base 3220 may be movable relative to one another. The base 3220 may comprise a neutralization unit 3225 (e.g., a neutralization sleeve). Prior to use, the neutralization unit 3225 may be rolled inside the base 3220

The device may comprise a lock 3215 (e.g., a safety tab) that is disposed relative to the core 3110 and the base 3220, such that the lock 3215 prevents a relative movement of the base 3220 over the core 3110. Additionally, the lock 3125 may prevent rotation of the core 3110 relative to the handle 3210 and/or the base 3220. Referring to FIG. 19A, the method of use of the device 3200 may comprise extracting a portion of the handle 3210 from within the core 3110 of the device 3200 (process 3250). The handle 3210 and/or the core 3110 may comprise a locking mechanism to prevent a complete removal (or extraction) of the handle 3210 from the core 3110. The method may comprise removing the lock 3215 to allow movement of the core 3110 and the base 3220 (process 3255). The method may comprise removing the protecting layer 3260 from the adhesive surfaces of the core 3110 (process 3260).

Referring to FIG. 19B, the method may comprise holding the device 3200 by the handle 3210 of the device 3200 (process 3265). The method may comprise aligning the initial contact surface 3113 of the flat surface 3112 of the core 3110 to an edge of the patch 1000, to make a connection between the core 3110 and the patch 1000 (process 3270). The method may comprise translating and/or rotating the core 3110 over the patch 1000 to remove the patch 1000 from the subject's skin (process 3175). In some cases, both the core 3110 and the handle 3210 may be rotated and translated over the patch 1000 during the removal of the patch 1000. Alternatively, the core 3110 may rotate relative to the handle 3210 during the removal of the patch 1000. As shown in FIG. 19B, the device 3200 may be compatible for a right-handed use, wherein the user may hold the device 3200 by the right hand to remove the covering 1000 from the subject. The device 3200 may be designed to be compatible for a left-handed use, wherein the user is holding the device 3200 by the left hand to remove the covering 1000 from the subject. In such a case, the direction of rotation 3275-2 of the core 3110 may be opposite of the direction of rotation 3275 of the core 3110 as provided in FIG. 19B. In another alternative, the device 3200 may be configured to be compatible for both the right-handed use and the left-handed use. In such a case, the core 3110 may be configured to rotate relative to the handle 3210 in both directions, and the direction of rotation of the core 3110 may be determined by the direction of translation of the device 3200 over the covering 1000.

A portion of the handle 3210 of the device 3200 may be configured to be angled, tilted, twisted, and/or rotated relative to the length of the core 3110. Such relative movement of the portion of the handle 3210 may improve (e.g., make it easier) to direct translation of the core 3110 over the covering 1000 that is disposed on different parts of the subject's body (e.g., non-flat and flat areas, including the chest). The relative movement 3252 of the portion of the handle 3210 relative to the length of the core 3110 may be facilitated by one or more hinges 3212 within the handle

3210. The rotation 3275-3 if the core 3110 may be directed or induced as the core 3110 is being translated over the covering 1000. In some cases, the device 3200 may further comprise a locking mechanism (e.g., a mechanical and/or electrical lock) to secure the relative position of the portion of the handle 3210 after, for example, it is angled with respect to the length of the core 3110.

Referring to FIG. 19C, the method may comprise completely removing the patch 1000 onto the core 3110 of the device 3200 (process 3280). Referring to FIG. 19D, the method may comprise depressing (e.g., pressing down) the handle 3210 into the core 3110 (process 3285). In some cases, once the handle 3210 is inserted back into the core 3110, the handle 3210 may be locked such that it can no longer be withdrawn from the core 3110. Referring to FIG. 19E, the method may comprise depressing (e.g., pressing down) the core 3110 into an opening of the base 3220 (process 3290). Alternatively or in addition to, the base 3220 may be moved over the core 3110. The relative movement of the core 3110 and the base 3220 may initiate unrolling of the neutralization unit 3225 over the core 3110 and over the patch 1000 that is retrieved on the core 3110. Referring to FIG. 19F, a relative movement of the base 3220 from one end of the core 3110 to an opposite end of the core 3110 may completely trap and cover the core 3110 and the retrieved patch 1000 inside the neutralization unit 3225. The method may comprise locking (e.g., automatically or manually) the base 3220 to prevent any further movement of the base 3220 to the core 3110 (process 3295). In this example, an identifier 3225 may be operatively coupled to the neutralization unit 3225, such that the unrolling of the neutralization unit 3225 may reveal the identifier 3225 as well. In some cases, the identifier may be coupled to an outer surface or an inner surface of the neutralization unit 3225. In another case, the identifier may be part of the neutralization unit 3225. Referring to FIG. 19G, in some cases, the method may comprise releasing a neutralization liquid 3226 (e.g., encapsulant or deactivator) upon unrolling of the neutralization unit 3225. In such a case, the neutralization unit 3225 may comprise a sleeve and a neutralizer container. The neutralizer container may release the neutralization liquid 3226 when the core 3110 is enclosed by the sleeve (or as the sleeve is enclosing the core 3110). The neutralization liquid 3226 may fill at least a portion of the enclosed space within the neutralization unit 3225 that is sufficient to cover the retrieved patch 1000.

FIG. 20 shows schematic illustrations of systems and methods of using a device 3300 to remove a covering 1000 (e.g., a patch) from a subject. In some cases, the device 3300 may utilize various aspects of the system and method for removing a covering by the device of the present disclosure, e.g., the device 3100 and/or 3200. Referring to FIG. 20A, the device 3300 may comprise at least three components. The device 3300 may comprise a core 3110 that is contained in a housing 3310. The housing may comprise a lid 3312, which lid 3312 may be opened to remove the core 3110 from the housing 3310. The lid may be sealed with a tag 3314 (e.g., a tamper evident tag or tape) to track whether the lid has been opened (e.g., tampered) prior to its intended use. The housing 3310 may comprise a window 3316 that is transparent or semi-transparent to allow visualization of at least a portion of the core 3110 stored inside the housing 3310. Once the core 3110 is used to retrieve the patch 1000 from the subject and the core 3110 is put back into the housing 3310, the window 3316 may allow visualization of the retrieved patch 1000 on the core 3110. Similar to the core 3110 of the device 3100 or 3200, the core 3110 of the device 3300 may comprise a flat surface 3112 and a round surface 3111 that both comprise an adhesive material. At least a portion of the flat surface 3112 may exhibit a stronger binding strength to the patch 1000 than the round surface 3111. In some cases, the at least the portion of the flat surface 3112 may be an area 3113 of the flat surface 3112 to be utilized to make an initial connection between the flat surface 3112 and the patch 1000. Another component of the device 3300 may be a handle 3320. At least a portion of the handle 3320 may be configured to be coupled to the core 3110 for removal of the patch 1000 from the subject. In an example, a portion of the handle 3320 may be inserted into the core 3110. In another example, a portion of the handle 3320 may adhere to the core 3110. Various coupling mechanisms may be used to couple the handle 3320 to the core 3110. Another component of the device 3300 may be a neutralization unit 3330. The neutralization unit 3330 may comprise a container that contains the drug neutralizer, and an opening 3332 (e.g., a nozzle) to release the neutralizer. The opening 3332 may be configure to be inserted and/or operatively coupled to an opening 3318 (e.g., a one-way opening, such as, for example, a one-way valve) of the housing 3310. In some cases, an activation switch disposed on the neutralization unit 3330 may need to be engaged to direct the neutralization unit 3330 to release the neutralizer through the nozzle 3332 and into the one-way valve 3318 of the housing 3310. Alternatively, the operative coupling of the nozzle 3332 to the one-way valve 3318 may automatically direct the neutralization unit 3330 to release the neutralizer into the housing 3310.

Referring to FIG. 20B, the method may comprise breaking the tag 3314 to open the lid 3312 of the housing 3310 (process 3350). Referring to FIG. 20C, the method may comprise coupling the handle 3320 to the core 3110 while the core 3110 is contained within the housing 3310 (process 3352). In this example, a portion of the handle 3320 may inserted into a hollow portion of the core 3110. The handle 3320 and/or the core 3110 may comprise a lock (e.g., a reversible lock) to stabilize the coupling. Referring to FIG. 20D, the method may comprise, removing the core 3110 from the housing 3310 by pulling on the handle 3320 (process 3354). Referring to FIG. 20E, the method may comprise removing the protecting layer 3114 (e.g., a film) from the core 3110 to expose the adhesive surfaces 3111, 3112, and 3113, as abovementioned (process 3356). Referring to FIG. 20F, the method may comprise using the core 3110 (via holding on to the handle 3320) to remove the patch 1000 from the skin of the subject (process 3360). The process 3360 may utilize various aspects of the methods of removing a covering of the present disclosure, e.g., the process 3170 through 3174 of FIG. 18 or the process 3265-3275 of FIG. 19. Referring to FIG. 20G, the patch 1000 may be completely removed from the subject and retrieved onto the core 3110 of the device 3300.

Referring to FIG. 20H, the method may comprise reinserting the core 3110 back into the housing 3310 (process 3370). Referring to FIG. 20I, the method may comprise releasing and removing the handle 3320 from the core 3110, such that the core 3110 remains inside the housing 3310 (process 3372). In some cases, the handle 3320 may comprise a releasing unit (e.g., a switch) to initiate its release from the core 3110. In some cases, the handle 3320 may be manually released from the core 3110 (e.g., by twisting the handle 3320 relative to the core). In some cases, the core 3110 may be coupled to the housing 3310, and a strength of such coupling may be sufficient for the user to pull out the handle 3320 from the core 3110 without any additional release mechanism. Referring to FIG. 20J, the neutralization unit 3330 may be coupled to the housing 3310 (process 3380). In this example, the nozzle 3332 of the neutralization unit 3330 may be inserted into the one-way valve 3318 of the housing 3310. Upon insertion, the neutralization unit 3330 may release the neutralization liquid 3334 into the housing, and the neutralization liquid 3334 may contact at least the retrieved patch 1000 to deactivate and/or encapsulate any residual drug within the patch 1000. In some cases, the coupling of the neutralization unit 3330 to the housing 3310 may initiate a mechanism (e.g., releasing a mechanical lock) to allow a cover 3342 (e.g., a security strip) of the identifier 3340 to be removed (process 3382). Referring to FIG. 20K, the neutralization unit 3330 may be removed from the housing 3310, and the cover 3342 may be completely detached, thereby exposing the identifier 3340 (process 3386).

Figure 20M:
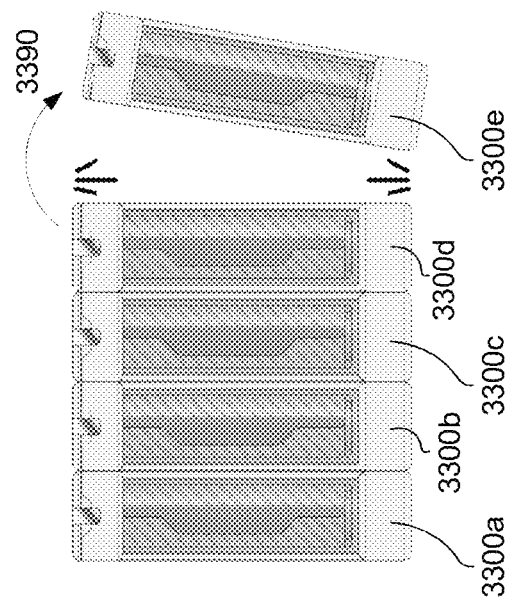
Figure 20L:
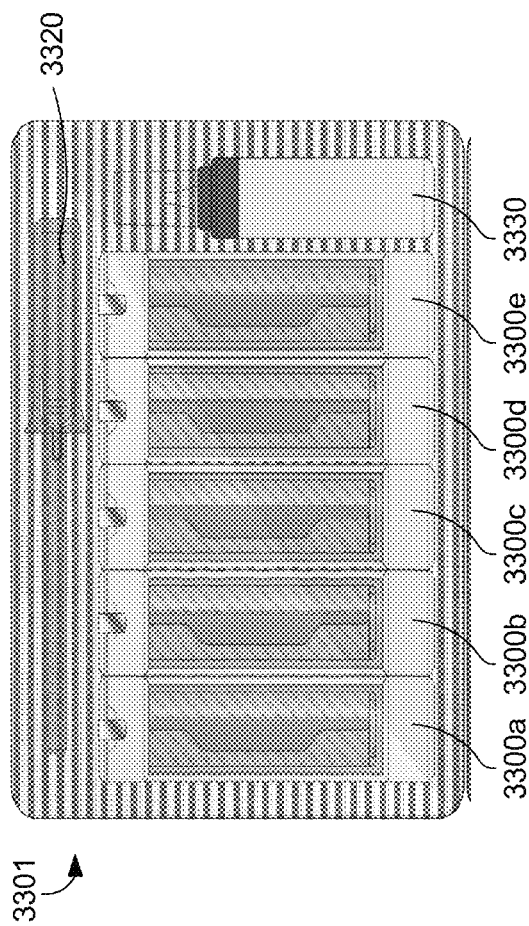

Referring to FIG. 20L, in some cases, the device 3300 may be provided as part of a kit that comprises (1) a plurality of the device 3300, along with (2) the handle 3320, and/or (3) the neutralization unit 3330. The kit may comprise at least 2, 3, 4, 5, 6, 7, 8, 9, 10, or more of the device 3300. The kit may comprise at most 10, 9, 8, 7, 6, 5, 4, 3, or 2 of the device 3300. The plurality of devices in the kit may or may be coupled to one another. When coupled to one another, each device of the plurality of devices may be detachable from the others. Alternatively, the plurality of devices may be irreversibly coupled to another (e.g., the housings of the plurality of devices may be irreversible coupled to another). In this example, the kit may comprise 5 devices 3300*a*, 3300*b*, 3300*c*, 3300*d*, and 3300*e* (i.e., a penta-pak). Referring to FIG. 20M, each device of the 5 devices may be detached from the others when used to remove a covering from a subject (process 3390). In some cases, each device 3300*a*, 3300*b*, 3300*c*, 3300*d*, or 3300*e* may be returned to a collection center (e.g., to a central pharmacy) individually. Alternatively, the plurality of devices in the kit 3300*a*, 3300*b*, 3300*c*, 3300*d*, and 3300*e* may be returned together to the collection center.

FIG. 21 shows schematic illustrations of systems and methods of using a device 3400 to remove a covering 1000 (e.g., a patch) from a subject. In some cases, the device 3300 may utilize various aspects of the system and method for removing a covering by the device of the present disclosure, e.g., the device 3100, 3200, and/or 3300. Referring to FIG. 21A, the device 3400 may comprise at least two components. The device 3400 may comprise a housing 3410 and a core 3420. The housing 3410 may comprise a handle 3416 for the user to grab onto during use of the device 3400. The housing 3410 may be configured to receive the core 3420. In other words, the core 3420 may be loaded onto the housing 3410 for the process of removing the patch 1000 from the subject's skin. In some cases, after use, the core 3420 may be removable from the housing 3410. The housing 3410 may be configured such that the core 3420, once loaded, may be able to rotate relative to the housing 3410. The housing may comprise a cartridge 3412 (e.g., a neutralization cartridge). In an example, the neutralization cartridge 3412 may be loaded with at least one neutralization sheet 3414. During use, the at least one neutralization sheet 3414 from the neutralization cartridge 3412 may be applied to the patch 1000 that is retrieved by the core 3110 to neutralize (e.g., encapsulate and/or deactivate) any access medication in the patch 1000. As abovementioned, the core 3420 of the device 3400 may comprise a connection mechanism (e.g., an adhesive material) to bind (e.g., selectively bind) the patch 1000 and remove the patch 1000 from the skin of the subject.

Referring to FIG. 21A, the method may comprise removing a protecting layer 3422 (e.g., a film) from the core 3420 to expose the adhesive surface of the core 3420 (process 3450). In addition, the method may comprise engaging the neutralization cartridge 3412 to the core 3420 (process 3455). In an example, at least a portion of the neutralization cartridge 3412 may be pressed or pushed to direct the neutralization cartridge 3412 towards the core 3420. Alternatively or in addition to, the engaging may comprise coupling a portion (e.g., a leading edge) of the neutralization sheet 3414 to a surface of the core 3420. The portion of the neutralization sheet 3414 may be coupled to the surface of the core 3420 automatically (e.g., upon the engaging of the neutralization cartridge 3412 to the core 3420) or manually (e.g., user pulls the neutralization sheet 3414 and directs adhesion between the neutralization sheet 3414 and the core 3420). Once the neutralization sheet 3414 and the surface of the core 3420 are coupled, a movement (e.g., rotation) of the core 3420 may induce movement (e.g., pull) the neutralization sheet 3414 from the neutralization cartridge 3412 and onto the adhesive surface of the core 3420.

Referring to FIG. 21B, the method may comprise aligning the device 3400 to an edge of the patch 1000 on the subject, and generating a connection (e.g., adhesion) between at least a portion of the core 3420 to the edge of the patch 1000. The method may further comprise translating the device 3400 across the patch 1000 (process 3460). In this example, the translating of the device 3400 may induce rotation of the core 3420 and the neutralization cartridge 3412, such that the core (i) binds and peels off the patch 1000 from the subject's skin, and simultaneously (ii) is laminated by the neutralization sheet 3414. The lamination of the core 3420 by the neutralization sheet 3414 may completely cover and seal the patch 1000 on the core 3420, thereby preventing any further access and tampering. Depending on how the neutralization sheet 3414 is initially loaded to the core 3420, the core 3420 and the neutralization cartridge 3412 may rotate in the same direction (e.g., clockwise or counterclockwise) or in opposite directions during the removal and retrieval of the patch 1000 by the device 3400. Referring to FIG. 21C, the patch 1000 may be retrieved onto the surface of the core 3420, and the patch 1000 may be sealed by the neutralization sheet 3414. As shown in FIG. 21C, at least a portion of the neutralization sheet 3414 may be transparent or semi-transparent to allow visualization of the retrieved patch 1000 through the neutralization sheet 3414. Additionally, as shown in FIG. 21C, at least another portion of the neutralization sheet 3414 may comprise an identifier 3430, as abovementioned, for tracking and accountability purposes. The identifier 3430 may be disposed on an inner side (e.g., the side being in contact with the core 3420) or its opposite side.

In some cases, the device 3400 may be part of a kit comprising a plurality of the core 3420 that are compatible with the housing 3410. The kit may comprise at least one housing 3410 and at least 2, 3, 4, 5, 6, 7, 8, 9, 10, or more of the core 3420. The kit may comprise at least one housing 3410 and at most 10, 9, 8, 7, 6, 5, 4, 3, or 2 of the core 3420. Once a first core 3420*a* is loaded to the housing 3410 and a first patch is removed by the first core 3420*a*, the first core 3420*a* may be detached from the housing 3410. Subsequently, a second core 3420*b* may be loaded to the housing 3410 to remove a second patch.

FIG. 22 shows schematic illustrations of systems and methods of using a device 3500 to remove a covering 1000 (e.g., a patch) from a subject. In some cases, the device 3500 may utilize various aspects of the system and method for removing a covering by the device of the present disclosure, e.g., the device 3100, 3200, 3300, and/or 3400. The device 3500 may comprise a neutralization cartridge 3510 that comprise one or more neutralization sheet 3520. Referring to FIG. 22A, the method may comprise aligning the device 3500 to an edge of the patch 1000 on the subject, and generating a connection (e.g., adhesion) between at least a portion of the device 3500 (e.g., a contact roller 3512) to the edge of the patch 1000. The method may further comprise translating the device 3500 across the patch 1000 (process 3550). Referring to FIG. 22B, the method may comprise encapsulating (i.e., laminating) the patch 1000 as it is being removed from the subject (process 3555). In this example, the encapsulating may comprise enclosing the removed patch 1000 between two or more layers (e.g., anti-tampering layers with or without drug-deactivating neutralizer(s)). In some cases, the two or more layers may be transparent or semi-transparent for visualization of the retrieved patch 1000. Referring to FIG. 22C, an example of a patch 1000 that is captured between two or more encapsulating layers 3520 is shown. A portion of the two or more encapsulating layers 3520 may comprise an identifier 3522, as abovementioned, for tracking and accountability purposes.

FIG. 23 shows schematic illustrations of systems and methods of using a device 3600 to remove a covering 1000 (e.g., a patch) from a subject. In some cases, the device 3600 may utilize various aspects of the system and method for removing a covering by the device of the present disclosure, e.g., the device 3100, 3200, 3300, 3400, and/or 3500. Referring to FIG. 23A, the device 3600 may comprise an encapsulation unit 3620. A bottom surface of the encapsulation unit 3620 may comprise a connection mechanism (e.g., adhesive materials) to selectively bind and remove the patch 1000 from the subject's skin. Prior to use, the bottom surface of the encapsulation unit 3620 may be protected by a protecting layer 3630 (e.g., a film or an adhesive backing). The device 3600 may comprise a handle 3610 disposed relative to the encapsulation unit 3620 and the protecting layer 3630, such that the protecting layer 3630 cannot be removed from the encapsulation unit 3620 without engaging the handle 3610.

Referring to FIG. 23B, the method may comprise extracting the handle 3610 to allow removal of the protecting layer 3630 from the encapsulation unit 3620 (process 3650). Referring to FIG. 23C, the method may comprise removing the protecting layer 3630 from the encapsulation unit 3620 (process 3655). The protecting layer 3630 may be completely detached from the encapsulation unit 3620. Referring to FIG. 23D, the method may comprise aligning an initial contact surface 3622 of the bottom surface of the encapsulation unit 3620 to an edge of the patch 1000, to make a connection between the encapsulation unit 3620 and the patch 1000 (process 3660). Subsequently, the encapsulation unit 3620 may be pressed against the patch 1000 (and optionally the skin of the subject) to allow adhesion of the encapsulation unit 3620 to the entire exposed surface of the patch 1000. Referring to FIG. 23E, once the encapsulation unit 3620 is adhered to and covers the patch 1000, the method may comprise removing (e.g., peeling off) a top layer 3620a of the encapsulation unit 3620 from a bottom layer 3620b of the encapsulation unit 3620 (process 3665). A newly exposed surface of the top layer 3620a may comprise neutralizer (e.g., encapsulant or chemical deactivators). A newly exposed surface of the bottom layer 3620b may comprise an adhesive to bind to the roller 3615. The bottom layer 3620b may be attached to the roller 3615. Referring to FIG. 23F, the method may comprise translating the roller 3615 over the bottom layer 3620b, such that the bottom layer 3620, along with the patch 1000 attached to a bottom surface of the bottom layer 3620, is retrieved over the surface of the roller 3615, thereby retrieving the patch 1000 from the subject's skin (process 3670). Referring to FIG. 23G, the method may comprise applying the top layer 3620a over the removed patch 1000, the bottom layer 3620b comprising the removed patch 1000, and the roller 3615 (process 3675). In some cases, application of the top layer 3620a over the removed patch 1000 may physically encapsulate the retrieved patch 1000 inside the device 3600. In some cases, application of the top layer 3620a over the removed patch 1000 may apply the neutralizer(s) from the top layer 3620a to the removed patch 1000 to deactivate any excess drugs. Referring to FIG. 23H, once the patch 1000 is encapsulated and/or neutralized by the device 3600, the method may comprise removing an identifier protecting layer to reveal the identifier to be used for tracking and accountability purposes (process 3680).

In some embodiments, a covering removal device may be applied to at least a portion of the covering when it is time to remove the covering from the subject (e.g., subsequent to a prescribed medication period). Alternatively, the covering removal device may be applied to the at least the portion of the covering while the covering is applied to the subject (e.g., during the prescribed medication period). In some cases, the covering removal device may be applied to the at least the portion of the covering during at least 1%, 2%, 3%, 4%, 5%, 10%, 15%, 20%, 25%, 30%, 40%, 50%, 60%, 70%, 80%, 90%, 95%, 99%, or more of the prescribed medication period. In some cases, the covering removal device may be applied to the at least the portion of the covering during at most 100%, 90%, 80%, 70%, 60%, 50%, 40%, 30%, 25%, 20%, 15%, 10%, 5%, 4%, 3%, 2%, 1%, or less of the prescribed medication period.

Covering

In some embodiments, the covering (e.g., bandage, patch) can comprise an attachment zone. An initial contact between the covering and the device can occur at the attachment zone of the covering. In some cases, the area of the attachment zone of the covering may be about 10% to about 100% of the area of the covering. In some cases, the area of the attachment zone of the covering may be at least about 10%, 20%, 30%, 40%, 50%, 60%, 70%, 80%, 90%, or more of the area of the covering. In some cases, the area of the attachment zone of the covering may be at most about 100%, 90%, 80%, 70%, 60%, 50%, 40%, 30%, 20%, 10%, or less of the area of the covering.

In some embodiments, the covering may be a patch that comprises an active side that releases the drug onto the skin. The area of the attachment zone of the patch may be a portion of the patch or an entirety of the nonactive side of the patch. In some cases, the area of the attachment zone of the patch may be about 10% to about 100% of the area of the nonactive side of the patch. In some cases, the area of the attachment zone of the patch may be at least about 10%, 20%, 30%, 40%, 50%, 60%, 70%, 80%, 90%, or more of the area of the nonactive side of the patch. In some cases, the area of the attachment zone of the patch may be at most about 90%, 80%, 70%, 60%, 50%, 40%, 30%, 20%, 10%, or less of the area of the nonactive side of the patch.

In some embodiments, the attachment zone comprising the connection mechanism may be present on one or more corners of the patch, one or more edges of the patch, one or more different areas of the patch, or the entire area of the patch. In some cases, the attachment zone of the patch may have a shape that is circular, triangular, square, rectangular, pentagonal, hexagonal, or any partial shape or combination of shapes thereof. The attachment zone of the device may have a shape that corresponds to the respective attachment zone of the patch. Accordingly, the shape and/or layout of the connection mechanism in the attachment zone of the patch may substantially match to the shape and/or layout of the corresponding connection mechanism in the attachment zone of the device.

In some embodiments, the attachment zones of the patch and the device may be protected by one or more removable (peelable) covers. The cover(s) may be removed (e.g., by a practitioner) when the patch needs to be removed from the subject. A binding strength between each of the attachment zones and the cover(s) may be less (weaker) than a binding strength between the "active" side of the patch (e.g., the adhesive of the patch in contact with the subject's skin) and the subject. As such, removal of the cover(s) from the attachment zone of the patch may not initiate removal of the patch from the subject.

In some embodiments, the attachment zone of the patch may be on an extension of the patch. The patch may include an extension (e.g., a lip or an overhang) that extends beyond the periphery of the patch. The extension may be on one or more sides of the patch. In an example, the extension may be attached to one or more sides of a cover of the patch. In another example, the extension may be attached to a component of the patch that is not the cover of the patch. The attachment zone on the extension of the patch may be used to initiate the connection between the patch and the device.

In some embodiments, during removal of the patch while using the device, a binding strength between the attachment zones of the patch and the device may be greater than the binding strength between the active side of the patch and the subject. As such, the initial contact between the attachment zones of the patch and the device may not be disconnected during removal of the patch from the subject by the device.

The patch disclosed herein can comprise one or more sensors. The sensor(s) may measure one or more parameter(s). The sensor(s) may detect a change in the parameter(s) from a time to one or more different times. The parameter(s) may be a characteristic of the patch, a substrate onto which the patch is applied (e.g., skin of the subject or any other user of the patch), and/or any surrounding medium of the patch (e.g., ambient air, water, etc.). Examples of the parameter(s) measured and/or detected by the sensor(s) can include temperature, thermal conductivity, humidity, pressure, strain, stiffness, pH, electrical impedance, electrical conductivity, and sweat. In some cases, the sensor(s) may detect sweat rate or sweat loss of the subject. In some cases, the sensor(s) may detect a presence and/or amount (e.g., concentration) of one or more components present in the subject's sweat, such as chloride ions, hydronium ions, glucose, lactate, deoxyribonucleic acid, ribonucleic acid, peptide, protein, etc. The sensor(s) may be present on one or more corners of the patch, one or more edges of the patch, one or more different areas of the patch, or the entire area of the patch.

In some cases, the sensor(s) may include a microfluidics device. In some cases, the sensor(s) may include a transistor (e.g., a field effect transistor). In some cases, the sensor(s) may include a piezoelectric sensor. In some cases, the sensor(s) may include a polymer comprising conductive particles (e.g., graphite, graphene, carbon nanotube, fullerene, etc.). In some cases, the sensor(s) may include a film that comprises a salt (e.g., cobalt chloride for detection of water) or a polypeptide (e.g., an enzyme that reacts with lactate, glucose, etc.).

In some cases, the sensor(s) may be a bendable sensor. In such a case, the patch comprising the sensor(s) may be a flexible electronic device, a wearable electronic device, a wearable microfluidics device, etc.

The patch can comprise a memory device (e.g., random access memory) that is operatively in communication with the sensor(s). The memory device can store data comprising the measured and/or detected parameter(s) by the sensor(s). The patch can comprise the communications device (e.g., RFID, NFC, Bluetooth, Wi-Fi, etc.) that is operatively in communication with the memory device and/or the sensor(s). The communications device can transfer (e.g., wirelessly) the data stored in the memory device or a live measurement or detection of the parameter(s) by the sensor(s) to an external device (e.g., a computer or a mobile device).

In some cases, it may be required for the sensor(s) of the patch to be connected to the external device upon application of the patch to the subject. The sensor(s) may measure or detect the parameter(s) periodically during an active period of the patch (e.g., a prescribed duration). For example, upon application of the patch, the sensor(s) of the patch may measure and record the parameter(s) and store the data in the memory device of the patch. If an unexpected variation in the parameter(s) is detected by the sensor(s), the patch may automatically (and wirelessly) send an alert message to the external device. The external device may forward the alert message to a healthcare professional's network and/or a centralized location that monitors distribution and usage of the patch. Such mechanism may help determine if and when the patch is removed prematurely before the prescribed duration (e.g., 72 hours for a fentanyl patch). Such mechanism may help prevent or discourage diversion of the patch to illicitly use or collect the medication in the patch.

In an example, a partial or complete removal of the patch from the skin of the subject may result in a detectable fluctuation of strain within the patch or temperature of the surrounding environment. Subsequently, the sensor may use the communications device to send an alert message of a potential diversion of the patch.

Alternatively or in addition to, once the patch is removed and retrieved in the device, the sensor(s)' data stored in the memory device of the patch may be retrieved by the central location that collects the retrieved patches. The central location may retroactively monitor for any fluctuation in the parameter(s) during the active period of the sensor.

The patch disclosed herein can comprise a first side and a second side. The second side may be opposite the first side. The first side may be a front side, and the second side may be a back side. Accordingly, the front side and back side may be opposite to each other. The front side may be a protective layer of the patch. The back side may be an adhesive layer (e.g., an adhesive film) that is configured to adhere to the subject's skin. The adhesive layer may be positioned at one or more corners, one or more sides, and/or one or more regions of second side. In some cases, the adhesive layer may be peripheral to a center of the second side of the patch or cover the entire area of the second side of the patch. The adhesive layer may comprise of a material that is water resistant (e.g., sweat resistant) to prevent detachment of the patch from the subject's skin without a deliberate effort of removal. In some cases, the adhesive layer may include a pressure-sensitive adhesive. In such, the application of the patch to the skin of the subject may require an application of pressure on the patch for a predetermined length of time (e.g., 1, 2, 3, 4, 5, or 10 minutes).

The patch can comprise a drug carrier layer (e.g., a reservoir, an active layer, a drug matrix, etc.) disposed between the first side and the second side. In some cases, the drug carrier layer may control a rate of drug release from the patch onto the skin of the subject. The drug carrier layer may release the drug through the second side (e.g., the adhesive layer) and onto the skin of the subject. Accordingly, the first side may be a nonactive side of the patch, and the second side may be an active side of the patch. As such, the nonactive side and the active side may be opposite to each other. In some cases, the adhesive material of the active side may comprise a material that is permeable to the drug that is loaded in the patch. In some cases, the drug carrier layer and the adhesive layer may be the same layer. Accordingly, the active side of such patch may be both the drug carrier layer and the adhesive layer.

Prior to application of the patch to the subject's skin, the adhesive layer on the back side of the patch may be protected by one or more removable (peelable) covers. The cover(s) may also overlay the area of the drug carrier layer to protect the drug carrier layer.

The protective layer of the patch and the cover(s) on the active of the patch may comprise of a material that is substantially impermeable to the drug compound, such as polymers, metal foils, etc. Suitable polymers may include, for instance, polyethylene terephthalate, polyvinylchloride, polyethylene, polypropylene, polycarbonate, polyester, and so forth. The selection of a desired material for the protective layer of the patch and the cover(s) on the active of the patch may depend on the solubility and diffusivity of the drug loaded into the patch. The adhesive material for adhering to the skin may include acrylic adhesives, solvent-based rubber adhesives, silicone adhesives, etc.

The drug carrier layer of the patch may be an open volume space, gel, solid structure, etc. The drug carrier layer may comprise porous fiber webs (e.g., woven or nonwoven), apertured films (e.g., with one or more holes), foams, sponges, etc. In some examples, polymeric materials may be used to form the drug carrier layer, such as silicones, acrylic resins, acetate copolymers (e.g., ethylene vinyl acetate), plasticized polyvinyl acetate/polyvinyl chloride resins, plasticized hydrolyzed polyvinyl alcohol, rubber-based adhesives (e.g., polyisobutylenes extended with a solvent such as mineral oil), plasticized polyvinyl chloride, polyethylene glycols and polypropylene glycols of varying molecular weights, cellulose esters, polyolefins, etc.

When the drug carrier layer and the adhesive layer are the same layer, such layer may comprise a selection or a combination of materials abovementioned.

FIG. 24A is a cross-sectional side view of a covering that is adhered on a subject's skin 1009 (e.g., a patient's skin), in accordance with an embodiment. The covering may be a patch 1000 that is pre-medicated. The patch 1000 may generally comprise of two opposite sides: (i) a nonactive side 1001 and (ii) an active side 1002 that is in contact with the subject's skin 1009. The nonactive side 1001 of the patch 1000 may comprise a patch cover 1010. The active side 1002 of the patch 1000 may comprise an adhesive 1030 that is configured to adhere to the subject's skin 1009. The patch 1000 may further comprise a drug matrix 1003 to carry the drug and release the drug onto the subject's skin 1009. The patch cover 1010 may be substantially impermeable to the drug loaded in the drug matrix 1003 to prevent leakage of the drug and/or unintended exposure of the drug to an unintended bodily area.

FIG. 24B is a schematic view of the nonactive side 1001 of the patch 1000, in accordance with an embodiment. The nonactive side 1001 may indicate the name of the drug 1011 (e.g., fentanyl) and/or the drug dosage 1013 (e.g., 100 mcg/h) specific for the patch 1000. FIG. 24C is a schematic view of the active side of the patch 1000, in accordance with an embodiment. In some cases, the drug matrix 1003 and the adhesive 1030 may be separate layers. Accordingly, the active side 1002 may show the adhesive 1030 and at least a portion of the drug matrix 1003. The drug matrix 1003 may be one piece or a combination of multiple pieces that are attached to the active side 1002 of the patch 1000. Each piece in the combination of multiple pieces of the drug matrix 1003 may have different or substantially the same amounts of the drug loaded. The drug matrix 1003 may cover about 10% to about 100% of the area of the active side 1002. The drug matrix 1003 may cover at least about 10%, 20%, 30%, 40%, 50%, 60%, 70%, 80%, 90%, or more of the area of the active side 1002. The drug matrix 1003 may cover at most about 100%, 90%, 80%, 70%, 60%, 50%, 40%, 30%, 20%, 10%, or less of the area of the active side 1002. The adhesive 1030 may cover at least a periphery of the active side 1002 of the patch 1000 to securely attach the patch 1000 to the skin 1009. The adhesive 1030 may cover about 10% to about 100% of the area of the active side 1002. The adhesive 1030 may cover at least about 10%, 20%, 30%, 40%, 50%, 60%, 70%, 80%, 90%, or more of the area of the active side 1002. The adhesive 1030 may cover at most about 100%, 90%, 80%, 70%, 60%, 50%, 40%, 30%, 20%, 10%, or less of the area of the active side 1002. In some cases, the adhesive 1030 may overlay the drug matrix 1003. In some cases, the adhesive 1030 and the drug matrix may not overlap.

In some cases, the drug matrix 1003 and the adhesive 1030 may be the same layer. Accordingly, the drug matrix may comprise an adhesive material configured to adhere to the skin 1009. The adhesive material of the drug matrix may be incorporated into at least a portion of the drug matrix. In an example, the adhesive material may be incorporated into the periphery of the drug matrix. In another example, the adhesive material may be incorporated into the entirety of the drug matrix.

FIG. 24D is a cross-sectional side view of a patch 1000 that is adhered on a subject's skin 1009 (e.g., a patient's skin), in accordance with an embodiment. The patch 1000 may generally comprise of two opposite sides: (i) a nonactive side 1001 and (ii) an active side 1002 that is in contact with the subject's skin 1009. The nonactive side 1001 of the patch 1000 may comprise a patch cover 1010. The active side 1002 of the patch 1000 may comprise a drug in adhesive (DIA) layer 1035 that is configured to (i) store the drug, (ii) adhere to the subject's skin 1009, and (iii) release the drug into the subject's skin 1009. The patch cover 1010 may be substantially impermeable to the drug loaded in the drug matrix 1003 to prevent leakage of the drug and/or unintended exposure of the drug to an unintended bodily area.

FIG. 24E is a schematic view of the nonactive side 1001 of the patch 1000 containing the DIA layer 1035, in accordance with an embodiment. The nonactive side 1001 may indicate the name of the drug 1011 (e.g., fentanyl) and/or the drug dosage 1013 (e.g., 100 mcg/h) specific for the patch 1000. FIG. 24F is a schematic view of the active side of the patch 1000 containing the DIA layer 1035, in accordance with an embodiment. The active side 1002 may be covered by the DIA layer 1035.

FIG. 25A is a schematic illustration of a patch 1000 with one or more patch identifiers 1020 on the patch 1000, in accordance with an embodiment. For example, the identifier(s) 1020 may be on the patch cover 1010 of the nonactive side 1001 of the patch 1000. The identifier(s) 1020 may be an addition to the drug name 1011 and/or the drug dosage 1013 on the patch cover 1010. In some cases, the identifier(s) 1020 may be in place of the drug name 1011 and/or the drug dosage 1013 on the patch cover 1010. The identifier(s) 1020 may be for the practitioner to scan and electronically record receipt and/or application of the correct patch 1000 in a database. In some cases, the date, time and/or location of scanning the identifier(s) 1020 may be automatically updated to the database. In some cases, the practitioner may need to log in (e.g., with the practitioner's user identification (ID) and password) to the computer that is operatively coupled to the scanner that scans the identifier(s) 1020. Thus, the electronic information about the practitioner may be automatically updated to the database when scanning the identifier(s) 1020 of the patch 1000. This may initiate tracking of the patch 1000, as well as the practitioner who is responsible for applying the patch. Scanning the identifier(s) 1020 may initiate the a digital loop on tracking the patch 1000, thereby electronically linking the patient, the specific patch 1000, and the practitioner with a date, time and/or location of the patch application. In an example, the identifier(s) 1020 may be scanned subsequent to removing the patch 1000 from its packaging and prior to applying it to the subject's skin. The drug name 1011, drug dosage 1013, and/or the identifier(s) 1020 may be provided in a permanent, non-erasable ink to prevent accidental or intentional manipulation of them.

In some embodiments, the identifier(s) 1020 may be one or more MRC. The MRC may include a linear MRC 1021, as shown in FIG. 25B, or a matrix (or two-dimensional) MRC 1022, as shown in FIG. 25C. Examples of the linear MRC 1021 include Australia Post barcode, Codabar, Code 25 (interleaved or non-interleaved), Code 11, Code 32 (or Farmacode), Code 39, Code 49, Code 93, Code 128, Digital indeX (DX), European Article Numbers (EAN), Facing Identification Mark, Intelligent Mail barcode, Interleaved 2 of 5 (ITF), Modified Plessey, Pharmacode, Postal Alpha Numeric Encoding Technique (PLANET), PostBar, Postal Numeric Encoding Technique, Universal Product Code (e.g., UPC-A and UPC-E), etc. Examples of the matrix MRC 1022 include Aztec, ColorCode, Color Construct Code, CrontoSign, CyberCode, d-touch, DataGlyphs, Data Matrix, Datastrip Code, Digimarc Barcode, DotCode, DWCode, EZcode, High Capacity Color Barcode, Han Xin Barcode, HueCode, InterCode, MaxiCode, Mobile Multi-Colored Composite (MMCC), NexCode, PDF417, Qode, Quick Response (QR) code, ShotCode, Snapcode, SPARQCode, VOICEYE, etc.

In some embodiments, the identifier(s) 1020 may include a communications device 1023, as shown in FIG. 25D. Examples of the communications device 1023 include a RFID system and a NFC system.

For removal of the patch 1000 from the subject's skin 1009, a person responsible for removing the patch 1000 (e.g., the practitioner) may scan the identifier(s) 1020 (e.g., the linear MRC 1021, the matrix MRC 1022, or the communications device 1023) on the patch cover 1010. Scanning the identifier(s) 1020 prior to removal of the patch 1000 may help the practitioner to confirm that: (i) the subject (e.g., the patient) is correct; (ii) the time of removal is correct; and (iii) the patch to be removed and retrieved is correct. In an example, the patient may have two or more patches that have different removal times, and the extra step of scanning the identifier(s) 1020 prior to removal of the patch may help identify the correct patch that need be removed by the practitioner.

FIG. 26A is a cross-sectional side view of a variation of the patch 1000 that includes a patch removal mechanism, in accordance with an embodiment. The patch 1000 may include one or more adhesive strip(s) 1040 on the nonactive side 1001 of the patch cover 1010. The adhesive strip(s) 1040 may be the connection mechanism for the patch 1000 to initiate contact with the device 100. The adhesive strip(s) 1040 may cover a portion of the area of the patch cover 1010. The adhesive strip(s) 1040 may be protected by one or more adhesive liner(s) 1041 when (i) the patch 1000 is stored in a packaging prior to use and (ii) the patch 1000 is in use on the subject's skin 1009. During removal of the patch 1000, the adhesive liner(s) 1041 may be removed to expose the adhesive strip(s) 1040. The adhesive strip(s) 1040 may bind to a portion of the patch removal device 100 to generate a connection between the patch 1000 and the device 100. Subsequently, the device 100 may be moved (e.g., rolled or translated over the patch 1000) to initiate removal of the patch 1000.

FIGS. 26B and 26C are schematic views of the nonactive side 1001 of the patch 1000, in accordance with an embodiment. Referring to FIG. 26B, the adhesive liner(s) 1041 is completely covering and protecting the adhesive strip(s) 1040. Referring to FIG. 26C, the adhesive strip(s) 1040 is exposed once the adhesive liner(s) 1041 is removed.

FIG. 27A is a cross-sectional side view of a variation of the patch 1000 that includes a patch removal mechanism, in accordance with an embodiment. The patch 1000 may include, in an order (or direction) away from the subject's skin 1009: the patch adhesive 1030 to adhere to the subject's skin 1009; the drug matrix 1003; a protective layer 1005; an adhesive 1045 for patch removal; and the patch cover 1010. The protective layer 1005 may cover an entire area of the drug matrix 1003. The protective layer 1005 may comprise of a material that is substantially impermeable to the drug compound in the drug matrix 1003. The adhesive 1045 may be the connection mechanism for the patch 1000 to initiate contact with the device 100. Prior to removal of the patch 1000 from the subject's skin 1009, the patch cover 1010 may overlay and protect the adhesive 1045. For removal of the patch 1000, the patch cover 1010 may be removed (e.g., peeled off) by the practitioner to expose the adhesive 1045. The device 100 may come in contact with the adhesive 1045, and the adhesive 1045 may bind to a portion of the device 100 to generate a connection between the patch 1000 and the device 100. Subsequently, the device 100 may be moved (e.g., rolled or translated over the patch 1000) to initiate removal of the patch 1000.

FIGS. 27B and 27C are schematic views of the nonactive side 1001 of the patch 1000 after the patch cover 1010 is removed, in accordance with an embodiment. Referring to FIG. 27B, the patch 1000 has a planar adhesive 1046. In some cases, the planar adhesive 1046 may include the drug name 1012, the drug dosage 1014, and/or the identifier(s) 1020 that is specific for the patch 1000. Referring to FIG. 27C, the patch 1000 has a peripheral adhesive 1047. The peripheral adhesive 1047 may be positioned near the edges of the patch 1000. In some cases, a non-adhesive surface 1048 of the protective layer 1005 that is not covered by the peripheral adhesive 1047 may include the drug name 1012, the drug dosage 1014, and/or the identifier(s) 1020 specific for the patch 1000.

The patch described herein can include one or more indicators. After the patch has been applied and adhered to the subject, the indicator(s) may indicate if the patch has been removed, at least partially or entirely, from the subject. Thus, such indicator(s) may be one or more patch removal indicator(s). In some cases, the indicator(s) may change from a first state to a second state when the patch is removed from the subject at least partially or entirely. The first state and the second state may be different. In some cases, the indicator(s) may be operatively in communication with the adhesive of the patch that adheres to the subject. As such, a detachment of at least a portion of the adhesive from the subject may trigger the indicator(s) to change from the first state to the second state. In an example, a disruption of a polymeric network within the adhesive may trigger the state change of the indicator(s). Such state change of the indicator(s) may be irreversible. In an example, if at least a portion of the patch has been (i) removed from the subject (thus, causing the indicator(s) to transition from the first state to the second state) and (ii) subsequently re-applied to the subject, the indicator(s) may still be in its second state. In some cases, the indicator(s) may be useful in preventing an illicit use (e.g., a diversion) of the drug in the patch.

The indicator may be "on" in its first state, and the indicator may be "off" in its second state.

In some embodiments, the indicator(s) may be present on one or more corners of the patch, one or more edges of the patch, one or more different areas of the patch, or the entire area of the patch. In some cases, the indicator(s) have a shape that is circular, triangular, square, rectangular, pentagonal, hexagonal, or any partial shape or combination of shapes thereof. The indicator(s), may be a part of one or more components of the patch. In some cases, the indicator(s) may be a part of the patch cover, and such indicator(s) may or may not be visible on the active side of the patch. In some cases, the indicator(s) may be a part of an extension (e.g., a lip or an overhang) that of the patch cover. In some cases, the indicator(s) may be a part of the adhesive, and such indicator(s) may or may not be visible on the nonactive side of the patch.

In some embodiments, the indicator(s) may change from a first color to a second color that is different than the first color. Examples of the colors include red, orange, yellow, green, blue, purple, black, white, variations thereof, or combinations thereof. Alternatively or in addition to, the indicator(s) may change from an invisible marker (e.g., a number, letter, symbol, etc.) to a visible marker.

In some embodiments, the indicator(s) may be a physical change of the patch. In some cases, the patch may be designed such that a portion of the patch may be torn (but without causing accidental release of the drug from the patch) upon removal of the same or a different portion of the patch from the subject. The portion of the patch may be torn but not removed from the patch. If the patch has a connection mechanism to generate a connection with the device, such tearing mechanism described herein may not hinder the connection mechanism.

FIG. 28A is a schematic view of the patch 1000 that includes one or more indicators 1100, in accordance with an embodiment. The indicator(s) 1100 may be a part of the patch cover 1010, patch adhesive 1030, or any other parts of the patch 1000. The indicator(s) 1100 may be in its "off" state 1105 when (i) applied to the subject's skin 1009 and (ii) prior to detachment 1101 from the subject's skin 1009. Referring to FIG. 28B, once at least a portion of the patch 1000 has been detached 1101 from the subject's skin 1009, the indicator(s) 1100 may switch from its "off" state 1105 to its "on" state 1106. Such activated indicator(s) 1100 in the "on" state 1106 may be irreversible.

FIG. 29A is a cross-sectional side view of a variation of the patch 1000 that includes a patch removal mechanism, in accordance with an embodiment. The patch 1000 may include, in an order away from the subject's skin 1009: the patch adhesive 1030 to adhere to the subject's skin 1009; the drug matrix 1003; the patch cover 1010; and a Velcro™ hook 1050. The Velcro™ hook 1050 may be the connection mechanism for the patch 1000 to initiate contact with the device 100. Accordingly, the device 100 may include a corresponding Velcro™ loop to bind to the Velcro™ hook 1050 of the patch 1000. The Velcro™ hook 1050 may cover a portion of the patch cover 1010. In some cases, a protective cover may overlay the Velcro™ hook 1050 to prevent it from attaching to an unintended target. The protective cover may need to be removed from the Velcro™ hook 1050 prior to removing the patch 1000 by the device 100. In some cases, the Velcro™ hook 1050 may cover the entire patch cover 1010, and the protective cover that overlays the Velcro™ hook 1050 may include the drug name 1012, the drug dosage 1014, and/or the identifier(s) 1020 that is specific for the patch 1000.

FIG. 29B is a schematic view of a pairing between the patch 1000 that includes the Velcro™ hook 1050 on its nonactive side 1001 and the device 100 that includes a Velcro™ loop 1051 on its patch removal area, in accordance with an embodiment. In an example, the Velcro™ loop 1051 may be on the core 110 of the device 100. For removal of the patch 1000 from the skin 1009, the Velcro™ loop 1051 of the device 100 may come in contact with the exposed Velcro™ hook 1050 of the patch 100, and the Velcro™ loop 1051 and the Velcro™ hook 1050 may interact (e.g., interlock or entangle) to generate a connection between the device 100 and the patch 1000. Subsequently, the device 100 may be moved (e.g., rolled or translated over the patch 1000) to initiate removal of the patch 1000.

FIG. 29C is a cross-sectional side view of a variation of the patch 1000 that includes a patch removal mechanism, in accordance with an embodiment. The patch 1000 may include, in an order away from the subject's skin 1009: the patch adhesive 1030 to adhere to the subject's skin 1009; the drug matrix 1003; the patch cover 1010; and a Velcro™ loop 1052. The Velcro™ loop 1052 may be the connection mechanism for the patch 1000 to initiate contact with the device 100. Accordingly, the device 100 may include a corresponding Velcro™ hook to bind to the Velcro™ loop 1052 of the patch 1000. The Velcro™ loop 1052 may cover a portion of the patch cover 1010. In some cases, a protective cover may overlay the Velcro™ loop 1052 to prevent it from attaching to an unintended target. The protective cover may need to be removed from the Velcro™ loop 1052 prior to removing the patch 1000 by the device 100. In some cases, the Velcro™ loop 1052 may cover the entire patch cover 1010, and the protective cover that overlays the Velcro™ loop 1052 may show the drug name 1012, the drug dosage 1014, and/or the MRC that is specific for the patch 1000.

FIG. 29D is a schematic view of a pairing between the patch 1000 that includes the Velcro™ loop 1052 on its nonactive side 1001 and the device 100 that includes a Velcro™ hook 1053 on its patch removal area, in accordance with an embodiment. In an example, the Velcro™ hook 1053 may be on the core 110 of the device 100. For removal of the patch 1000 from the skin 1009, the Velcro™ hook 1053 of the device 100 may come in contact with the exposed Velcro™ loop 1052 of the patch 1000, and the Velcro™ hook 1053 and the Velcro™ loop 1052 may interact (e.g., interlock or entangle) to generate a connection between the device 100 and the patch 1000. Subsequently, the device 100 may be moved (e.g., rolled or translated over the patch 1000) to initiate removal of the patch 1000.

Although inventions abovementioned in FIGS. 29A-29D show the patch 1000 and the device 100 comprising the Velcro™ hook and the Velcro™ loop, respectively (or vice versa), any other hook-and-loop fasteners can be used to generate the connection between the device 100 and the patch 1000 for removing the patch 1000.

FIG. 30A is a cross-sectional side view of a variation of the patch 1000 that includes a patch removal mechanism, in accordance with an embodiment. The patch 1000 may include, in an order away from the subject's skin 1009: the patch adhesive 1030 to adhere to the subject's skin 1009; the drug matrix 1003; and the patch cover 1010. The patch cover 1010 may include one or more holes 1061. In some cases, the patch 1000 may include an additional layer that overlays at least a portion of the patch cover 1010, and the additional layer may include the hole(s) 1061. The hole(s) 1061 may be the connection mechanism for the patch 1000 to initiate contact with the device 100. Accordingly, the device 100 may include one or more hooks configured to couple with the hole(s) 1061. In some cases, the hole(s) 1061 may be near one or more edges of the patch 1000. In some cases, a protective cover may overlay the hole(s) 1061 to prevent it from coupling to an unintended target. In some cases, the protective cover may need to be removed from the hole(s) 1061 prior to removing the patch 1000 by the device 100.

FIG. 30B is a schematic view of a pairing between the patch 1000 that includes the hole(s) 1061 on its nonactive side 1001 and the device 100 that includes one or more hooks 1062 on its patch removal area, in accordance with an embodiment. In an example, the hook(s) 1062 may be on the core 110 of the device 100. For removal of the patch 1000 from the skin 1009, the hook(s) 1062 of the device 100 may come in contact with the exposed hole(s) 1061 of the patch 1000, and the hook(s) 1062 and the hole(s) 1061 may couple (e.g., interlock) to generate a connection between the device 100 and the patch 1000. Subsequently, the device 100 may be moved (e.g., rolled or translated over the patch 1000) to initiate removal of the patch 1000.

FIG. 30C is a cross-sectional side view of a variation of the patch 1000 that includes a patch removal mechanism, in accordance with an embodiment. The patch 1000 may include, in an order away from the subject's skin 1009: the patch adhesive 1030 to adhere to the subject's skin 1009; the drug matrix 1003; and the patch cover 1010. The patch cover 1010 may include one or more hooks 1063. In some cases, the patch 1000 may include an additional layer that overlays at least a portion of the patch cover 1010, and the additional layer may include the hook(s) 1063. The hook(s) 1063 may be the connection mechanism for the patch 1000 to initiate contact with the device 100. Accordingly, the device 100 may include one or more holes configured to couple with the hook(s) 1063. In some cases, the hook(s) 1063 may be near one or more edges of the patch 1000. In some cases, prior to removal of the patch 1000 from the subject's skin 1009, a protective cover may overlay the hook(s) 1063 to prevent it from coupling to an unintended target. In some cases, the protective cover may prevent any harmful damage to the subject by the hook(s) 1063 of the patch 1000. The protective cover may need to be removed from the hook(s) 1063 prior to removing the patch 1000 by the device 100.

FIG. 30D is a schematic view of a pairing between the patch 1000 that includes the hook(s) 1063 on its nonactive side 1001 and the device 100 that includes one or more holes 1064 on its patch removal area, in accordance with an embodiment. In an example, the hole(s) 1064 may be on the core 110 of the device 100. For removal of the patch 1000 from the skin 1009, the hole(s) 1064 of the device 100 may come in contact with the exposed hook(s) 1063 of the patch 1000, and the hole(s) 1064 and the hook(s) 1063 may couple (e.g., interlock) to generate a connection between the device 100 and the patch 1000. Subsequently, the device 100 may be moved (e.g., rolled or translated over the patch 1000) to initiate removal of the patch 1000.

Although inventions abovementioned in FIGS. 30A-30D show the patch 1000 and the device 100 comprising the hole(s) and loop(s), respectively (or vice versa), any other latch systems (e.g., hook and eye) can be used to generate the connection between the device 100 and the patch 1000 for removing the patch 1000. The latch systems may be reversible or irreversible.

FIG. 31A is a cross-sectional side view of a variation of the patch 1000 that includes a patch removal mechanism, in accordance with an embodiment. The patch 1000 may include, in an order away from the subject's skin 1009: the patch adhesive 1030 to adhere to the subject's skin 1009; the drug matrix 1003; and the patch cover 1010. The patch cover 1010 may include one or more snap studs 1071. In some cases, the patch 1000 may include an additional layer that overlays at least a portion of the patch cover 1010, and the additional layer may include the snap stud(s) 1071. The snap stud(s) 1071 may be the connection mechanism for the patch 1000 to initiate contact with the device 100. Accordingly, the device 100 may include one or more snap posts configured to couple with the snap stud(s) 1071. In some cases, the snap stud(s) 1071 may be near one or more edges of the patch 1000. In some cases, a protective cover may overlay the snap stud(s) 1071 to prevent it from coupling to an unintended target. In some cases, the protective cover may need to be removed from the snap stud(s) 1071 prior to removing the patch 1000 by the device 100.

FIG. 31B is a schematic view of a pairing between the patch 1000 that includes the snap stud(s) 1071 on its nonactive side 1001 and the device 100 that includes one or more snap posts 1072 on its patch removal area, in accordance with an embodiment. In an example, the snap post(s) 1072 may be on the core 110 of the device 100. For removal of the patch 1000 from the skin 1009, the snap post(s) 1072 of the device 100 may come in contact with the snap stud(s) 1071 of the patch 1000, and the snap post(s) 1072 and the snap stud(s) 1071 may couple (e.g., interlock) to generate a connection between the device 100 and the patch 1000. Subsequently, the device 100 may be moved (e.g., rolled or translated over the patch 1000) to initiate removal of the patch 1000.

FIG. 31C is a cross-sectional side view of a variation of the patch 1000 that includes a patch removal mechanism, in accordance with an embodiment. The patch 1000 may include, in an order away from the subject's skin 1009: the patch adhesive 1030 to adhere to the subject's skin 1009; the drug matrix 1003; and the patch cover 1010. The patch cover 1010 may include one or more snap posts 1073. In some cases, the patch 1000 may include an additional layer that overlays at least a portion of the patch cover 1010, and the additional layer may include the snap post(s) 1073. The snap post(s) 1073 may be the connection mechanism for the patch 1000 to initiate contact with the device 100. Accordingly, the device may include one or more snap studs configured to couple with the snap post(s) 1073. In some cases, the snap post(s) 1073 may be near one or more edges of the patch 1000. In some cases, a protective cover may overlay the snap post(s) 1073 to prevent it from coupling to an unintended target. The protective cover may need to be removed from the snap post(s) 1073 prior to removing the patch 1000 by the device 100.

FIG. 31D is a schematic view of a pairing between the patch 1000 that includes the snap post(s) 1073 on its nonactive side 1001 and the device 100 that includes one or more snap studs 1074 on its patch removal area, in accordance with an embodiment. In an example, the snap stud(s) 1074 may be on the core 110 of the device 100. For removal of the patch 1000 from the skin 1009, the snap stud(s) 1074 of the device 100 may come in contact with the snap post(s) 1073 of the patch 1000, and the snap stud(s) 1074 and the snap post(s) 1073 may couple (e.g., interlock) to generate a connection between the device 100 and the patch 1000. Subsequently, the device 100 may be moved (e.g., rolled or translated over the patch 1000) to initiate removal of the patch 1000.

Although inventions abovementioned in FIGS. 31A-31D show the patch 1000 and the device 100 comprising the snap stud(s) and snap post(s), respectively (or vice versa), any other male-to-female fastener systems (e.g., cap(s) and socket(s), eyelet(s) and stud(s), or dimple snap(s)) can be used to generate the connection between the device 100 and the patch 1000 for removing the patch 1000. The male-to-female fastener systems may be reversible or irreversible.

Figure 32A:
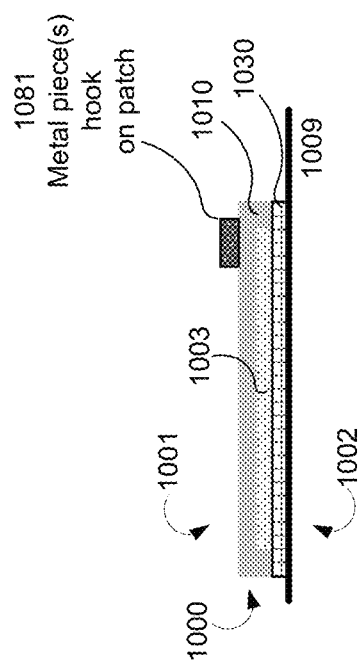
FIGS. 32A and 32B are schematic illustrations of a patch and a patch removal device with magnet(s) as a as a patch removal mechanism, in accordance with some embodiments.

FIG. 32A is a cross-sectional side view of a variation of the patch 1000 that includes a patch removal mechanism, in accordance with an embodiment. The patch 1000 may include, in an order away from the subject's skin 1009: the patch adhesive 1030 to adhere to the subject's skin 1009; the drug matrix 1003; and the patch cover 1010. The patch cover 1010 may include one or metal pieces 1081. In some cases, the patch 1000 may include an additional layer that overlays at least a portion of the patch cover 1010, and the additional layer may include the metal piece(s) 1081. The metal piece(s) 1081 may be the connection mechanism for the patch 1000 to initiate contact with the device 100. Accordingly, the device 100 may include one or more magnets configured to couple with the metal piece(s) 1081. In some cases, the metal piece(s) 1081 may be near one or more edges of the patch 1000. In some cases, a protective cover may overlay the metal piece(s) 1081. The protective cover may need to be removed from the metal piece(s) 1081 prior to removing the patch 1000 by the device 100.

Figure 32B:
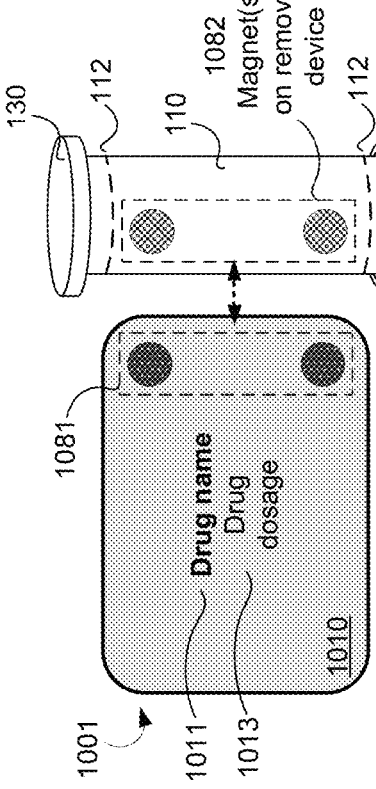

FIG. 32B is a schematic view of a pairing between the patch 1000 that includes the metal piece(s) 1081 on its nonactive side 1001 and the device 100 that includes one or more magnets 1082 on its patch removal area, in accordance with an embodiment. In an example, the magnet(s) 1082 may be on the core 110 of the device 100. For removal of the patch 1000 from the skin 1009, the magnet(s) 1082 of the device 100 may come in contact with the metal piece(s) 1081 of the patch 1000, and the magnet(s) 1082 and the metal piece(s) 1081 may couple to generate a connection between the device 100 and the patch 1000. Subsequently, the device 100 may be moved (e.g., rolled or translated over the patch 1000) to initiate removal of the patch 1000.

In some embodiments, the patch 1000 may include one or more magnets in place of the metal piece(s) 1081, and the device may include one or more metal pieces in place of the magnet(s) 1082. In some cases, both the patch 1000 and the device 100 may have one or more magnets to generate the connection between the patch 1000 and the device 100. In some cases, the patch and/or the device may have a combination of the magnet(s) and the metal piece(s) to generate the connection between the patch 1000 and the device 100.

The magnet(s) of the patch 1000 or the device 1000 may be of any type that provides a substantial magnetic field that can be used in the present invention. Suitable types of permanent magnets include metallic magnets (e.g., alnico magnets, ceramic magnets, and rare earth magnets), plastic magnets, and combinations thereof. Examples of alnico magnets include mixtures of materials including iron, cobalt, nickel, aluminum, and copper. Examples of ceramic magnets include strontium carbonate and iron oxide. Examples of rare earth magnets include neodymium and samarium-cobalt magnets. Examples of plastic magnets include magnetic polymers, such as a mixture of polyaniline and tetracyanoquinodimethane. In some cases, the magnet(s) may be electromagnetic magnet(s). In some cases, the magnet(s) may be temporary magnet(s) that become magnetic upon an exposure to an external magnetic field.

Figure 33:
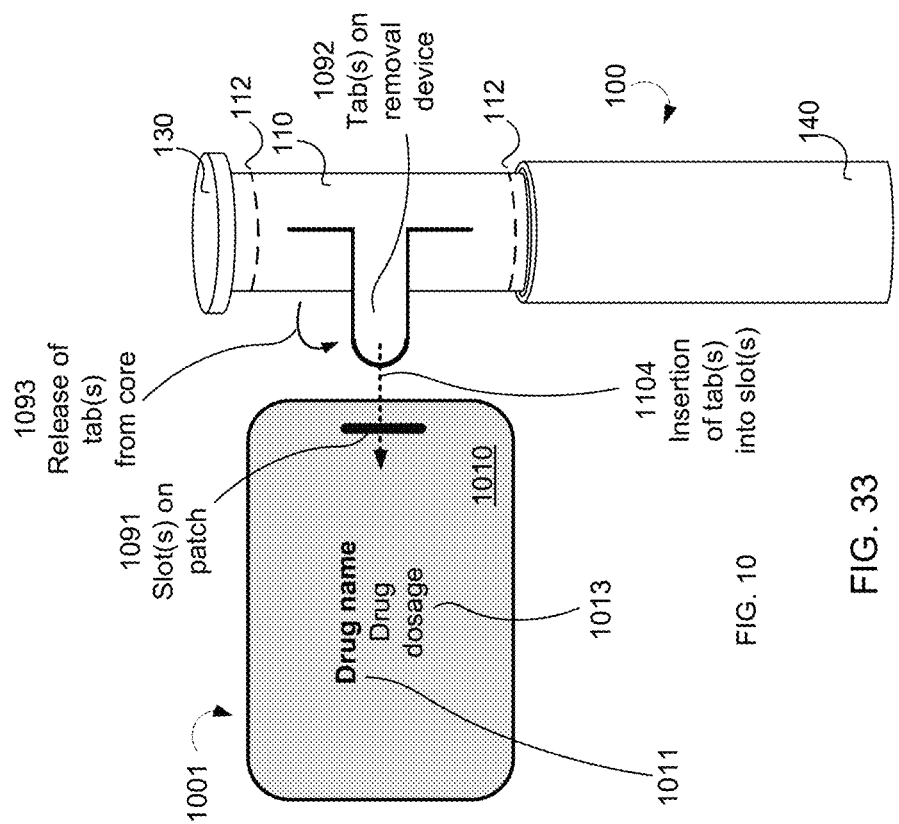
FIG. 33 is a schematic illustration of a pairing between a patch that includes slot(s) and a patch removal device that includes tab(s) as a patch removal mechanism, in accordance with an embodiment.

FIG. 33 is a schematic view of a pairing between the patch 1000 that includes one or more slots 1091 on the patch cover 1010 and the device 100 that includes one or more tabs 1092 on its patch removal area, in accordance with an embodiment. A combination of the slot(s) 1091 and the tab(s) 1092 may be the connection mechanism between the patch 1000 and the device 100. In some cases, the slot(s) 1091 may be near one or more edges of the patch 1000. In some cases, a protective cover may overlay the slot(s) 1091. The protective cover may need to be removed from the slot(s) 1091 prior to removing the patch 1000 by the device 100. In some cases, the tab(s) 1092 may be on the core 110 of the device 100. In some cases, the tab(s) 1092 may need to be released 1093 from the core 110 of the device 100 prior to generating the connection between the tab(s) 1092 and the slot(s) 1091.

For removal of the patch 1000 from the subject's skin 1009, the tab(s) 1092 of the device 100 may be inserted into the slot(s) 1091 of the patch 1000 to generate a connection between the device 100 and the patch 1000. Subsequently, the device 100 may be moved (e.g., rolled or translated over the patch 1000) to initiate removal of the patch 1000. In some cases, the insertion of the tab(s) 1092 into the slot(s) 1091 may be irreversible.

One or more surfaces of the tab(s) 1092 may be partially or entirely smooth, knurled, or serrated to adjust contact surface area and/or frictional force between the tab(s) 1092 and the slot(s) 1091. A surface of the patch cover 1010 that is adjacent to the slot(s) 1091 may be partially or entirely smooth, knurled, or serrated to adjust contact surface area and/or frictional force between the tab(s) 1092 and the slot(s) 1091.

Blockchain

The database of the present disclosure to store information (e.g., time, date, location, and/or identity of a practitioner responsible for retrieving a used patch from a subject) for closed loop tracking of medications (e.g., prescription medications, non-prescription medications) can comprise or utilize a block chain (or "blockchain") database. The term "blockchain," as used herein, can refer to a suite of distributed ledger technologies that can be programmed to record and track anything of value (e.g., financial transactions, land titles, medical records, etc.). The blockchain can be a peer-to-peer (P2P) decentralized open ledger (or computer architecture thereof) that relies on a distributed network shared among its users. Each of the users can hold a public ledger of every transaction carried out using the architecture, and each public ledger can be checked against one another to ensure accuracy and accountability. Thus, a blockchain-based database (or blockchain database) can be used in place of a physical, centralized database, to record and handle one or more transactions of digital objects (e.g., data). Maintenance of the blockchain can be performed by a P2P network of communicating nodes (or computer systems) that are running a software. The software can be programmed with a specific application (e.g., cryptocurrency software, financial services software, supply chain software, smart contracts software, etc.). Transactions such as "party X transfers an object (e.g., a digital object, such as, for example, cryptocurrency, prescriptions, etc.) Y to party Z" can be broadcasted to the P2P network (e.g., by using one or more software applications). The network nodes can validate the transactions, add them to their copy of the ledger, and then broadcast these ledger additions to other nodes. Thus, the blockchain can be a distributed database, wherein, in order to independently verify the chain of ownership or validity of any and every transferred object, each network node stores its own copy of the blockchain. In some cases, a new group of transactions (i.e., a block) is created (e.g., at a predetermined frequency, such as, for example, 6 times per hour), added to the blockchain, and quickly published to all nodes in the P2P network. Thus, each block can contain a cryptographic hash of the previous block to keep the previous block "accountable."

Tampering with transactions on the blockchain can become exponentially harder as time progresses, and can require extreme quantities of computing power to attempt, let alone succeed. In some cases, data stored in the blockchain can be included in integrity checks, in which transactions are assembled into a transaction merkle tree and hashed to produce a block header. Any alterations to transactions in a blockchain database can become apparent as the block would be invalid when indexed. As such, the blockchain's consensus mechanism can allow a data's hash to be published to the blockchain as irrefutable proof that the data existed at a given time in the past. Both the timestamp and the hash may be unalterable.

The covering (e.g., the patch), the packaging of the covering, the covering removal device, or the packaging of such device, as provided herein, can have an identifier (e.g., an identification device or a MRC). Scanning of such identifier may be updated to the blockchain database for closed loop tracking of medications, e.g., to track (i) production, supply, use, and retrieval of the covering (i.e., patch tracking), (ii) personal linking (e.g., recording identification of practitioner(s) responsible for application and/or removal of the covering), (iii) user or patient linking, (iv) covering removal device tracking, (v) pharmacy tracking (e.g., distributing the covering, receiving the device containing the covering, and/or (vi) destroying the device containing the covering), etc. In an example, the blockchain database may provide a record (e.g., a permanent or irrefutable record) of each transaction as the medication (e.g., in the patch) is moved along the supply chain, to a hospital (e.g., in an ADM), to a user (e.g., a patient), a medication removal device (e.g., a patch removal device), and back to a collection chain for discarding any unused medication. The blockchain database, as provided herein, can be an alterable and secured P2P network among patients, prescribers, pharmacy, government agencies (e.g., FDA, DEA, etc.), medication manufacturer, etc., to record and transfer data (e.g., medical history, prescription history, date of prescription, date of retrieval of the covering, etc.).

Computer System

Figure 34:
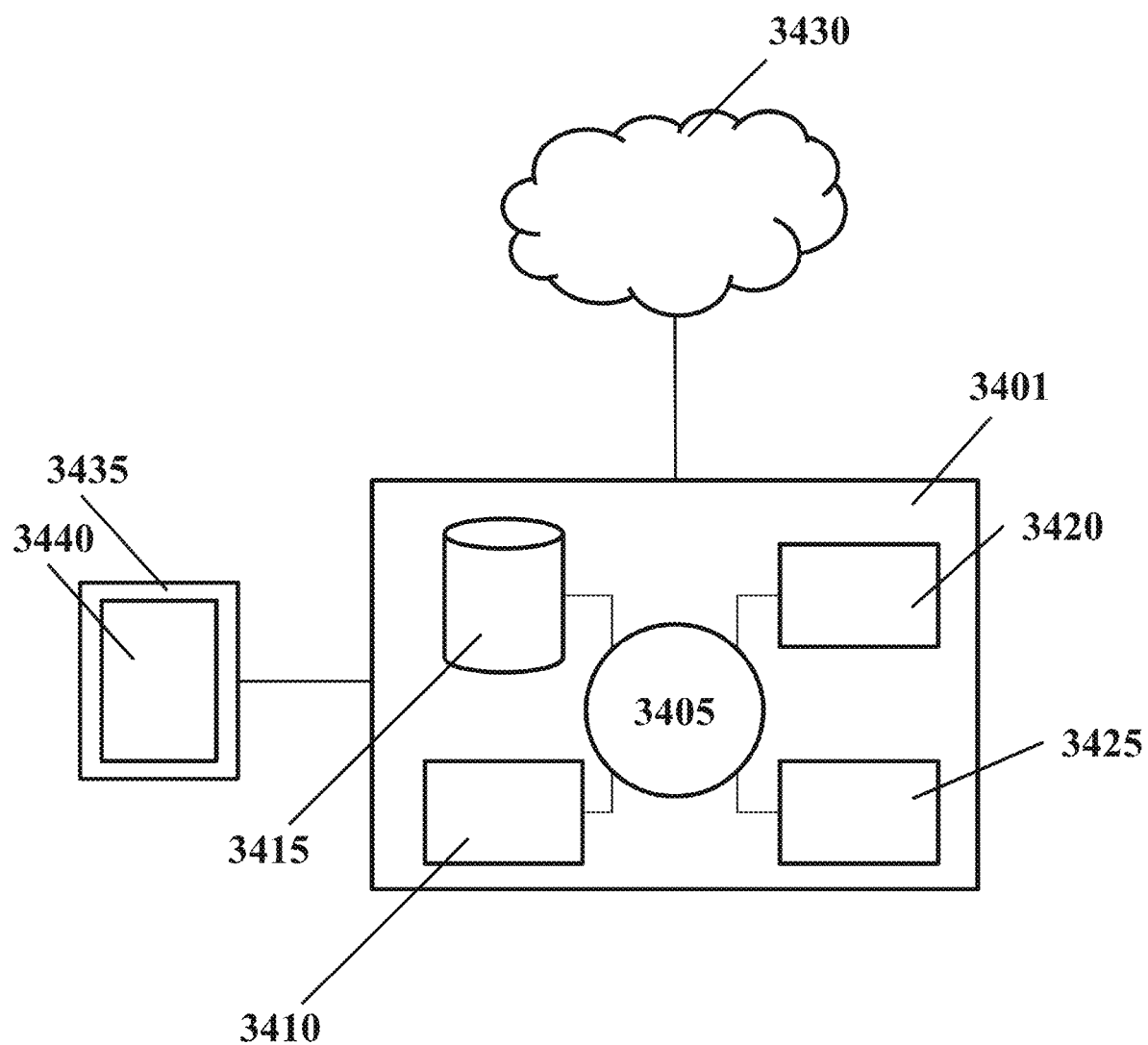
FIG. 34 shows a computer system that is programmed or otherwise configured to implement methods provided herein.

FIG. 34 shows a computer system 3401 that is programmed or otherwise configured to communicate with and regulate various aspects of tracking transfer, usage (e.g., application and/or removal), collection, and/or disposal of one or more coverings (e.g., one or more transdermal patches). The one or more coverings may or may not be pre-medicated. The computer system 3401 can communicate with, for example, one or more identifiers of a medical practitioner (e.g., a doctor, a nurse, etc.), one or more identifiers of the covering(s), one or more identifiers of a subject (e.g., a patient to whom the covering(s) may be applied to), one or more removal/collection device for the covering(s), one or more storage units of the covering(s) prior to their usage, one or more pharmacies, and/or one or more scanners of any of the subject identifiers. The computer system 3401 can be an electronic device of a user or a computer system that is remotely located with respect to the electronic device. The electronic device can be a mobile electronic device.

The computer system 3401 includes a central processing unit (CPU, also "processor" and "computer processor" herein) 3405, which can be a single core or multi core processor, or a plurality of processors for parallel processing. The computer system 3401 also includes memory or memory location 3410 (e.g., random-access memory, read-only memory, flash memory), electronic storage unit 3415 (e.g., hard disk), communication interface 3420 (e.g., network adapter) for communicating with one or more other systems, and peripheral devices 3425, such as cache, other memory, data storage and/or electronic display adapters. The memory 3410, storage unit 3415, interface 3420 and peripheral devices 3425 are in communication with the CPU 3405 through a communication bus (solid lines), such as a motherboard. The storage unit 3415 can be a data storage unit (or data repository) for storing data. The computer system 3401 can be operatively coupled to a computer network ("network") 3430 with the aid of the communication interface 3420. The network 3430 can be the Internet, an internet and/or extranet, or an intranet and/or extranet that is in communication with the Internet. The network 3430 in some cases is a telecommunication and/or data network. The network 3430 can include one or more computer servers, which can enable distributed computing, such as cloud computing. The network 3430, in some cases with the aid of the computer system 3401, can implement a peer-to-peer network, which may enable devices coupled to the computer system 3401 to behave as a client or a server.

The CPU 3405 can execute a sequence of machine-readable instructions, which can be embodied in a program or software. The instructions may be stored in a memory location, such as the memory 3410. The instructions can be directed to the CPU 3405, which can subsequently program or otherwise configure the CPU 3405 to implement methods of the present disclosure. Examples of operations performed by the CPU 3405 can include fetch, decode, execute, and writeback.

The CPU 3405 can be part of a circuit, such as an integrated circuit. One or more other components of the system 3401 can be included in the circuit. In some cases, the circuit is an application specific integrated circuit (ASIC).

The storage unit 3415 can store files, such as drivers, libraries and saved programs. The storage unit 3415 can store user data, e.g., user preferences and user programs. The computer system 3401 in some cases can include one or more additional data storage units that are external to the computer system 3401, such as located on a remote server that is in communication with the computer system 3401 through an intranet or the Internet.

The computer system 3401 can communicate with one or more remote computer systems through the network 3430. For instance, the computer system 3401 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 3401 via the network 3430.

Methods as described herein can be implemented by way of machine (e.g., computer processor) executable code stored on an electronic storage location of the computer system 3401, such as, for example, on the memory 3410 or electronic storage unit 3415. The machine executable or machine readable code can be provided in the form of software. During use, the code can be executed by the processor 3405. In some cases, the code can be retrieved from the storage unit 3415 and stored on the memory 3410 for ready access by the processor 3405. In some situations, the electronic storage unit 3415 can be precluded, and machine-executable instructions are stored on memory 3410.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 3401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 3401 can include or be in communication with an electronic display 3435 that comprises a user interface (UI) 3440 for providing, for example, an instruction to apply the covering(s) to the subject, an instruction to remove the covering(s) from the subject, and/or an instruction to keep the covering(s) on the subject for a certain duration of time. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 3405. The algorithm can, for example, track the covering(s) pre-administration to the subject, during administration to the subject, and/or post-administration to the subject In another example, the algorithm can track the covering(s) prior to usage of the transdermal patch, post-usage of the transdermal patch, prior to disposal of the used transdermal patch, during disposal of the used transdermal patch, and/or post-disposal of the used transdermal patch.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A covering removal device for selectively removing a covering from a bodily surface of a subject, the covering removal device comprising:
   a base structure; and
   an adhesive material coupled to the base structure, wherein the adhesive material aids in generating a connection between the covering removal device and the covering disposed on the bodily surface of the subject, wherein the covering removal device is configured to be moved across the bodily surface of the subject in order to selectively remove the covering from the bodily surface and capture the covering onto the covering removal device, without the covering removal device affecting or interfering with the bodily surface of the subject.

2. The device of claim 1, wherein a first binding strength between the adhesive material and the covering is greater than a second binding strength between the covering and the bodily surface underneath the covering.

3. The device of claim 1, wherein a first binding strength between the adhesive material and the covering is greater than a second binding strength between the adhesive material and an additional bodily surface of the subject adjacent to the covering.

4. The device of claim 1, wherein the adhesive material does not generate a connection with the bodily surface of the subject.

5. The device of claim 1, wherein the adhesive material is a solid, semi-solid, or gel.

6. The device of claim 1, wherein the base structure is a movable base structure.

7. The device of claim 6, wherein the movable base structure comprises a roller, and wherein an outwardly facing surface of the roller comprises the adhesive material.

8. The device of claim 1, wherein the covering is pre-medicated with a drug.

9. The device of claim 1, wherein the covering is not pre-medicated.

10. The device of claim 1, wherein the covering further comprises an additional covering, wherein the covering is disposed over an additional covering adjacent to the bodily surface of the subject.

11. The device of claim 1, further comprising a housing coupled to the base structure, wherein the base structure is configured to be released from the housing.

12. The device of claim 11, wherein the housing is configured to release the base structure and couple to an additional removable base structure.

13. The device of claim 1, wherein at least a portion of the base structure is flat.

14. The device of claim 1, wherein the covering removal device is operatively coupled to a source of a neutralizer, wherein the neutralizer is configured to neutralize any excess drug in the covering or an additional covering coupled to the covering.

15. The device of claim 14, wherein the source of the neutralizer is a part of the covering removal device.

16. The device of claim 14, wherein the source of the neutralizer is detachable from the covering removal device.

17. The device of claim 14, wherein the neutralizer is configured to (i) encapsulate the controlled substance and/or (ii) deactivate the controlled substance.

18. The device of claim 14, wherein the source of the neutralizer is a container configured to hold the neutralizer.

19. The device of claim 14, wherein the source of the neutralizer is a film configured to cover at least a portion of the covering.

20. The device of claim 1, further comprising a removable handle configured to be coupled to the base structure.

\* \* \* \* \*